(12) United States Patent
Nel et al.

(10) Patent No.: US 11,918,686 B2
(45) Date of Patent: *Mar. 5, 2024

(54) LIPID BILAYER COATED MESOPOROUS SILICA NANOPARTICLES WITH A HIGH LOADING CAPACITY FOR ONE OR MORE ANTICANCER AGENTS

(71) Applicant: The Regents of the University of California, Oakland, CA (US)

(72) Inventors: Andre E. Nel, Sherman Oaks, CA (US); Jeffrey I. Zink, Sherman Oaks, CA (US); Huan Meng, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 805 days.

This patent is subject to a terminal disclaimer.

(21) Appl. No.: 16/948,498

(22) Filed: Sep. 21, 2020

(65) Prior Publication Data

US 2021/0077397 A1    Mar. 18, 2021

Related U.S. Application Data

(63) Continuation of application No. 14/772,740, filed as application No. PCT/US2014/020857 on Mar. 5, 2014, now Pat. No. 10,828,255.

(60) Provisional application No. 61/858,388, filed on Jul. 25, 2013, provisional application No. 61/773,013, filed on Mar. 5, 2013.

(51) Int. Cl.

| | | |
|---|---|---|
| *A61K 9/127* | (2006.01) | |
| *A61K 9/00* | (2006.01) | |
| *A61K 9/51* | (2006.01) | |
| *A61K 31/337* | (2006.01) | |
| *A61K 31/4709* | (2006.01) | |
| *A61K 31/7068* | (2006.01) | |
| *A61K 31/7105* | (2006.01) | |
| *A61K 31/713* | (2006.01) | |
| *A61K 45/06* | (2006.01) | |
| *A61K 47/02* | (2006.01) | |
| *A61P 35/00* | (2006.01) | |

(52) U.S. Cl.
CPC .......... *A61K 9/127* (2013.01); *A61K 9/5115* (2013.01); *A61K 31/337* (2013.01); *A61K 31/4709* (2013.01); *A61K 31/7068* (2013.01); *A61K 31/7105* (2013.01); *A61K 31/713* (2013.01); *A61K 45/06* (2013.01); *A61K 47/02* (2013.01)

(58) Field of Classification Search
CPC .......... A61P 35/00; A61P 31/04; A61K 45/06; A61K 47/6929; A61K 9/127; A61K 47/6923; A61K 2039/55555; A61K 47/544; A61K 47/543; A61K 9/0019; A61K 8/14; A61K 8/553
See application file for complete search history.

(56) References Cited

U.S. PATENT DOCUMENTS

| | | |
|---|---|---|
| 4,737,323 A | 4/1988 | Martin et al. |
| 5,670,631 A | 9/1997 | Bayerl et al. |
| 6,296,870 B1 | 10/2001 | Needham et al. |
| 6,868,343 B1 | 3/2005 | Bayerl et al. |
| 8,734,816 B2 | 5/2014 | Liu et al. |
| 8,758,811 B2 | 6/2014 | Ho et al. |
| 8,992,984 B1 | 3/2015 | Brinker et al. |
| 9,532,949 B2 | 1/2017 | Zeineldin et al. |
| 9,579,283 B2 | 2/2017 | Brinker et al. |
| 10,143,660 B2 | 12/2018 | Nel et al. |
| 10,343,903 B2 | 7/2019 | Zink et al. |
| 10,765,636 B2 | 9/2020 | Nel et al. |
| 10,828,255 B2 | 11/2020 | Nel et al. |
| 11,096,900 B2 | 8/2021 | Nel et al. |
| 2003/0035842 A1 | 2/2003 | Kazakov et al. |
| 2004/0005352 A1 | 1/2004 | Lopez et al. |
| 2005/0249795 A1 | 11/2005 | Zhang et al. |
| 2006/0154069 A1 | 7/2006 | Lin et al. |
| 2007/0116753 A1 | 5/2007 | Hong et al. |
| 2008/0175992 A1 | 7/2008 | Plieth et al. |
| 2010/0255103 A1 | 10/2010 | Liong et al. |
| 2010/0284924 A1 | 11/2010 | Zink et al. |
| 2010/0310465 A1 | 12/2010 | Zink et al. |
| 2011/0104073 A1 | 5/2011 | Zeng et al. |
| 2011/0123601 A1 | 5/2011 | Ho et al. |
| 2011/0268791 A1 | 11/2011 | Liu et al. |
| 2012/0021034 A1 | 1/2012 | Zink et al. |
| 2012/0207795 A1 | 8/2012 | Zink et al. |

(Continued)

FOREIGN PATENT DOCUMENTS

| | | |
|---|---|---|
| AU | 2017206077 B2 | 11/2021 |
| EP | 2964201 A1 | 1/2016 |

(Continued)

OTHER PUBLICATIONS

U.S. Office Action (Restriction Requirement), dated Feb. 3, 2017, issued in U.S. Appl. No. 14/772,740.

(Continued)

*Primary Examiner* — Tracy Liu
(74) *Attorney, Agent, or Firm* — Tom Hunter; Weaver Austin Villeneuve & Sampson LLP

(57) ABSTRACT

A submicron structure comprising a silica body defining a plurality of pores that are suitable to receive molecules therein, and having a surface, and a phospholipid bilayer coating the surface, wherein said submicron structure has a maximum dimension of less than one micron, and wherein the phospholipid bilayer stably seals the plurality of pores; and wherein the submicron structure is a member of a monodisperse population of submicron structures.

20 Claims, 26 Drawing Sheets

(56) References Cited

U.S. PATENT DOCUMENTS

| | | | |
|---|---|---|---|
| 2013/0046274 A1 | 2/2013 | Zink et al. |
| 2013/0195963 A1 | 8/2013 | Serda et al. |
| 2014/0079774 A1 | 3/2014 | Brinker et al. |
| 2014/0138278 A1 | 5/2014 | Kennedy |
| 2014/0301951 A1 | 10/2014 | Liu et al. |
| 2015/0272885 A1 | 10/2015 | Ashley et al. |
| 2016/0008283 A1 | 1/2016 | Nel et al. |
| 2017/0095418 A1 | 4/2017 | Zink et al. |
| 2017/0173169 A1 | 6/2017 | Yantasee et al. |
| 2018/0098945 A1 | 4/2018 | Nel et al. |
| 2019/0160015 A1 | 5/2019 | Nel et al. |
| 2019/0216736 A1 | 7/2019 | Nel et al. |
| 2020/0383929 A1 | 12/2020 | Nel et al. |
| 2022/0160644 A1 | 5/2022 | Nel et al. |

FOREIGN PATENT DOCUMENTS

| | | |
|---|---|---|
| WO | WO 2006/015757 A1 | 2/2006 |
| WO | WO 2006/032136 A1 | 3/2006 |
| WO | WO 2010/078569 A2 | 7/2010 |
| WO | WO 2012/009448 A2 | 1/2012 |
| WO | WO 2012/149376 A2 | 11/2012 |
| WO | WO 2013/012891 A1 | 1/2013 |
| WO | WO 2014/138278 A1 | 9/2014 |
| WO | WO 2017/013250 A1 | 1/2017 |
| WO | WO 2017/120537 A1 | 7/2017 |
| WO | WO 2019/133884 A1 | 7/2019 |

OTHER PUBLICATIONS

U.S. Office Action dated Jun. 2, 2017, issued in U.S. Appl. No. 14/772,740.
U.S. Final Office Action dated Feb. 20, 2018, issued in U.S. Appl. No. 14/772,740.
U.S. Advisory Action dated Jun. 1, 2018, issued in U.S. Appl. No. 14/772,740.
U.S. Office Action dated Aug. 7, 2018, issued in U.S. Appl. No. 14/772,740.
U.S. Final Office Action dated Apr. 1, 2019, issued in U.S. Appl. No. 14/772,740.
U.S. Office Action dated Nov. 27, 2019, issued in U.S. Appl. No. 14/772,740.
U.S. Notice of Allowance dated Jun. 22, 2020, issued in U.S. Appl. No. 14/772,740.
U.S. Office Action dated Jan. 31, 2018 issued in U.S. Appl. No. 15/798,287.
U.S. Office Action dated May 29, 2018 issued in U.S. Appl. No. 15/798,287.
U.S. Notice of Allowance dated Jul. 19, 2018 issued in U.S. Appl. No. 15/798,287.
U.S. Office Action dated Sep. 4, 2019 issued in U.S. Appl. No. 16/164,030.
U.S. Miscellaneous Communication dated Apr. 22, 2020 issued in U.S. Appl. No. 16/164,030.
U.S. Examiner Initiated Interview Summary dated Apr. 23, 2020 issued in U.S. Appl. No. 16/164,030.
U.S. Notice of Allowance dated May 6, 2020 issued in U.S. Appl. No. 16/164,030.
U.S. Office Action dated Sep. 9, 2020 issued in U.S. Appl. No. 16/947,539.
U.S. Office Action dated Jul. 9, 2020 issued in U.S. Appl. No. 16/235,950.
U.S. Appl. No. 14/253,030 Office Action dated Dec. 9, 2016.
U.S. Appl. No. 14/253,030 Response as filed on May 9, 2017.
PCT International Search Report and Written Opinion dated Jun. 24, 2014 issued in PCT/US2014/020857.
PCT International Report on Patentability and Written Opinion dated Sep. 17, 2015 issued in PCT/US2014/020857.
European Extended Search Report dated Jul. 27, 2016 issued in Application No. EP 14 760 467.2.
European Office Action dated Aug. 23, 2018 issued in Application No. EP 14 760 467.2.
European 2nd Office Action dated May 26, 2020 issued in Application No. EP 14 760 467.2.
PCT International Search Report and Written Opinion dated Apr. 18, 2017 issued in PCT/US2017/012625.
PCT International Preliminary Report on Patentability and Written Opinion dated Jul. 10, 2018 issued in PCT/US2017/012625.
Chinese Office Action dated Aug. 14, 2020 issued in CN 201780010248.8.
European Extended Search Report dated Aug. 7, 2019 issued in Application No. EP 17736481.7.
Japanese Office Action dated Oct. 5, 2020 issued in JP 2018-535362.
PCT International Search Report and Written Opinion dated Mar. 27, 2019 issued in PCT/US18/67970.
PCT International Preliminary Report on Patentability and Written Opinion dated Jul. 7, 2020 issued in PCT/US18/67970.
Abigerges et al. (1995) "Phase I and pharmacologic studies of the camptothecin analog irinotecan administered every 3 weeks in cancer patients." *Clin Oncol* 13:210-221.
Al Shamsi et al. (2010) "Biocompatibility of calcined mesoporous silica particles with cellular bioenergetics in murine tissues." *Chem Res Toxicol* 23(11):1796-1805.
Angelos et al. (2007) "Mesostructured silica supports for functional materials and molecular machines." *Adv Funct Mater* 17:2261-2271.
Argyo, et al. (2013) "Multifunctional Mesoporous Silica Nanoparticles as a Universal Platform for Drug Delivery." *Chem. Mater.*, 26(1): 435-451.
Arruebo et al. (2006) "Development of Magnetic Nanostructured Silica-Based Materials as Potential Vectors for Drug-Delivery Applications." *Chem Mater* 18:1911-1919.
Arruebo et al. (Published Jul. 18, 2006) "Sustained release of doxorubicin from zeolite-magnetite nanocomposited prepared by mechanical activation." *Nanotechnology* 17:4057-4064.
Aryal, et al. (2011) "Polymeric Nanoparticles with Precise Ratiometric Control over Drug Loading for Combination Therapy." *Mol. Pharmaceutics* 8:1401-1407.
Ashley et al. (2011) "The targeted delivery of multicomponent cargos to cancer cells by nanoporous particle-supported lipid bilayers." *Nature Materials* 10(5):389-397.
Ashley et al. (2012) "Delivery of Small Interfering RNA by Peptide-Targeted Mesoporous Silica Nanoparticle-Supported Lipid Bilayers." *ACS Nano* 6:2174-2188.
Awasthi et al. (2013) "Comparative Benefits of Nab-Paclitaxel over Gemcitabine or Polysor-bate-Based Docetaxel in Experimental Pancreatic Cancer." *Carcinogenesis* 34: 2361-2369.
Bagwe et al. (Apr. 25, 2006) "Surface Modification of Silica Nanoparticles to Reduce Aggregation and Nonspecific Binding." *Langmuir* 22:4357-4362.
Baker et al. (2008) "Irinophore C, a Novel Nanoformulation of Irinotecan, Alters Tumor Vascular Function and Enhances the Distribution of 5-Fluorouracil and Doxorubicin." *Clin. Cancer Res.* 14:7260-7271.
Barbe et al. (2004) "Silica particles: A novel drug-delivery system." *Adv Mater* 16:1959-1966.
Bardelle (1993) "Membrane binding kinetics of factor VIII indicate a complex binding process." *J Biol Chem.* 268(12): 8815-24.
Bayerl, et al. (1990) "Physical Properties of Single Phospholipid Bilayers Adsorbed to Micro Glass Beads. A New Vesicular Model System Studied by 2H-Nuclear Magnetic Resonance." *Biophys. J.*, 58: 357-362.
Bourzac, K. (2012) "Nanotechnology: Carrying Drugs." *Nature*, 491: S58-S60.
Brigger et al. (2002) "Nanoparticles in cancer therapy and diagnosis." *Advanced Drug Delivery Reviews* 54:631-651.
Brumm et al. (1996) "The effect of increasing membrane curvature on the phase transition and mixing behavior of a dimyristoyl-sn-glycero-3-phosphatidylcholine/distearoyl-sn-glycero-3-phosphatidylcholine lipid mixture as studied by Fourier transform infrared spectroscopy and differential scanning calorimetry." *Biophys J.* 70: 1373-1379.

(56) References Cited

OTHER PUBLICATIONS

Buck et al. (2004) "Engineering Lipobeads: Properties of the Hydrogel Core and the Lipid Bilayer Shell" *Biomacromolecules*, 5: 2230-2237.

Buranda et al. (2003) "Biomimetic Molecular Assemblies on Glass and Mesoporous Silica Microbeads for Biotechnology" *Langmuir*, 19: 1654-1663.

Carmona-Ribeiro (2003) "Bilayer-forming synthetic lipids: drugs or carriers?" *Curr. Med. Chem.* 10: 2425-2446.

Cauda et al. (2010) "Colchicine-Loaded Lipid Bilayer-Coated 50 nm Mesoporous Nanoparticles Efficiently Induce Microtubule Depolymerization upon Cell Uptake" *Nano Letters* 10(7): 2484-2492.

Celano et al. (2004) "Cytotoxic effects of Gemcitabine-loaded liposomes in human anaplastic thyroid carcinoma cells," *BMC Cancer* 4(63):5 pages.

"CHEBI:53581—cetyttrimethylammonium chloride", Retrieved from the Internet: URL https://www.ebi.ac.uk/chebi/searchId.do?chebiId=CHEBI:53581, Sep. 11, 2013 (Sep. 11, 2013), Section "Synonyms" (2 Pages).

Chemburu et al. (2010) "Biomimetic Silica Microspheres in Biosensing" *Molecules*, 15: 1932-1957.

Chen et al. (2009) "Co-delivery of Doxorubicin and Bcl-2 siRNA by Mesoporous Silica Nanoparticles Enhances the Efficacy of Chemotherapy in Multidrug Resistant Cancer Cells." *Small* 5(23):2673-2677.

Chen, et al. (2014) "Antitumor efficacy of irinotecan-loaded galactosyl modified lipid bilayer-coated mesoporous silica nanoparticles against hepatocellular carcinoma cells." *Acta Pharmaceutica Sinica*, 49(5): 718-725. [English Translation of Chinese Article—30 Pages].

Cho et al. (2008) "Therapeutic nanoparticles for drug delivery in cancer." *Clin. Cancer Res.* 14(5): 1310-1316.

Chou et al. (2003) "Effect of Composition on the stability of liposomal irinotecan prepared by a pH gradient method." *J Biosci Bioeng* 95(4):405-408.

Cosco et al. (2009) "In vivo activity of gemcitabine-loaded PEGylated small unilamellar liposomes against pancreatic cancer" *Cancer Chemother Pharmacol*, 64(5):1009-1020.

Davis et al. (2008) "Nanoparticle therapeutics: an emerging treatment modality for cancer." *Nature Reviews Discovery* 7:771-782.

Davis, M. E., (2009) "The first targeted delivery of siRNA in humans via a self-assembling, cyclodextrin polymer-based nanoparticle: from concept to clinic." *Molecular Pharmacuetics* 6(3):659-668.

Dengler et al. (2013) "Mesoporous Silica-Supported Lipid Bilayers (Protocells) for DNA Cargo Delivery to the Spinal Cord." *J.Controlled Release* 168: 209-224.

Dolainsky et al. (1993) "Transverse relaxation in supported and nonsupported phospholipid model membranes and the influence of ultraslow motions: A 31P-NMR study" *J. Chem. Phys.* 98: 1712-1720.

Drummond et al. (2006) "Development of a highly active nanoliposomal irinotecan using a novel intraliposomal stabilization strategy." *Cancer Research* 66(6):3271-3277.

Duncan et al. (2005) "Polymer-drug conjugates: towards a novel approach for the treatment of endrocine-related cancer." *Endocrine-Related Cancer* 12: S189-S199.

Eschwege et al. (1996) "Detection of bilayer phospholipid-binding antibodies using flow cytometry" *Clin. Exp. Immunol.* 103: 171-175.

Federico et al. (2012) "Gemcitabine-Loaded Liposomes: Rationale, Potentialities and Future Perspectives." *Int. J. Nanomed.* 7: 5423-5436.

Ferrari, M. (2005) "Cancer Nanotechnology: Opportunities and Challenges." *Nat. Rev. Cancer* 5: 161-171.

Frese et al. (2012) "Nab-Paclitaxel Potentiates Gemcitabine Activity by Reducing Cytidine Deaminase Levels in a Mouse Model of Pancreatic Cancer." *Cancer Discovery* 2: 260-269.

Fritze et al. (2006) "Remote loading of doxorubicin into liposomes driven by transmembrane phosphate gradient," *Biochimica Et Biophysica Acta (BBA)—Biomembranes*, Elsevier, Amsterdam, NL, 1758(10):1633-1640.

Fuchs et al. (2006) "Irinotecan in the treatment of colorectal cancer." *Cancer Treat. Rev.* 32:491-503.

Gahlyan et al. (2014) "Oral Controlled Release Drug Delivery System—A Review" *PharmaTutor* 2(8): 170-178.

Gilbert et al. (1992) "Specificity of phosphatidylserine-containing membrane binding sites for factor VIII. Studies with model membranes supported by glass microspheres (lipospheres)." *J. Biol. Chem.* 267: 15861-15868.

Gorelikov et al. (2008) "Single-step coating of mesoporous silica on cetyltrimethyl ammonium bromide-capped nanoparticles." *Nano Letters* 8(1):369-373.

Grün et al. (1997) "The Synthesis of Micrometer- and Submicrometer-Size Spheres of Ordered Mesoporous Oxide MCM-41." *Adv. Mater.* 9(3):254-257.

Guiotto et al. (2004) "Synthesis, Characterization, and Preliminary in Vivo Tests of New Poly(ethylene glycol) Conjugates of the Antitumor Agent 10-Amino-7-ethylcamptothecin." *J. Med. Chem.* 47(5):1280-1289 [Abstract—2pages].

Haran et al. (1993) "Transmembrane ammonium sulfate gradients in liposomes produce efficient and stable entrapment of amphipathic weak bases." *Biochim Biophys Acta Biomembr* 1151:201-215.

He et al. (2011) "In vivo biodistribution and urinary excretion of mesoporous silica nanoparticles: effects of particle size and PEGylation." *Small* 7:271-280.

Hetzer et al. (1998) "Asymmetric Molecular Friction in Supported Phospholipid Bilayers Revealed by NMR Measurements of Lipid Diffusion" *Langmuir*, 14: 982-984.

Jabr-Milane et al. (2008) "Multi-functional nanocarriers to overcome tumor drug resistance." *Cancer Treat. Rev.* 34:592-602.

Jin et al. (1996) "Lipobeads: a hydrogen anchored lipid vesicle system" *FEBS Lett.* 397: 70-74.

Junglas et al. (2003) "Molecular Order Parameter Profiles and Diffusion Coefficients of Cationic Lipid Bilayers on a Solid Support" *Langmuir*, 19: 1914-1917.

Kasbauer et al. (1999) "Effect of cationic lipids in the formation of asymmetries in supported bilayers." *Biophys. J.* 76: 2600-2605.

Katiyar et al. (2006) "Synthesis of ordered large pore SBA-15 spherical particles for adsorption of biomolecules." *J Chromatog* 1122(1-2):13-20.

Kiser et al. (1998) "A synthetic mimic of the secretory granule for drug delivery" *Nature*, 394: 459-62.

Kiser et al. (2000) "Lipid-coated microgels for the triggered release of doxorubicin" J. Control Release, 68: 9-22.

Kneuer et al. (2000) "A nonviral DNA delivery system based on surface modified silica-nanoparticles can efficiently transfect cells in vitro." *Bioconjugate Chem.* 11:926-932.

Kochy & Bayerl (1993) "Lateral diffusion coefficients of phospholipids in spherical bilayers on a solid support measured by resonance relaxation" *Phys. Rev. E.* 47: 2109-16.

Lammers et al. (2010) "Nanomedicine Formulations for Combination Therapies." *Nano Rev.*, 1: 5705 (4 pages) DOI: 10.3402/nano.v1i0.5705.

Lee et al. (2008) "Synthesis and characterization of positive-charge functionalized mesoporous silica nanoparticles for oral drug delivery of an anti-inflammatory drug." *Advanced Functional Materials* 18:3283-3292.

Li et al. (2012) "Mesoporous silica nanoparticles in biomedical applications." *Chem Soc Rev* 41(7):2590-2605.

Li et al. (2013) "Preliminary study on pH-sensitive lipid bilayer-coated mesoporous silica nanoparticles as a novel drug carrier for antitumor drug." *Acta Pharmaceutica Sinica*, 48(2): 291-297. [English Translation of Chinese Article—27 Pages].

Li et al. (2015) "Multiple Layer-by-Layer Lipid-Polymer Hybrid Nanoparticles for Improved FOLFIRINOX Chemotherapy in Pancreatic Tumor Models." *Adv Func Mat* 25(5):788-798.

Lin et al. (2009) "Synthesis and Characterization of Biocompatible and Size-Tunable Multifunctional Porous Silica Nanoparticles." *Chem. Mater.* 21:3979-3986.

(56) References Cited

OTHER PUBLICATIONS

Linseisen et al. (1996) "2H-NMR and DSC study of DPPC-DODAB mixtures" *Chem. Phys. Lipids*, 83: 9-23.
Linseisen et al. (1997) "Differences in the Physical Properties of Lipid Monolayers and Bilayers on a Spherical Solid Support." *Biophys. J.* 72: 1659-1667.
Liong et al. (2008) "Multifunctional inorganic nanoparticles for imaging, targeting and drug delivery." *ACS Nano* 2(5):889-896 [and supporting information attached].
Liong et al. (2009) "Mesostructured Multifunctional Nanoparticles for Imaging and Drug Delivery." *J. Mater. Chem.* 19(35):6251-6257 15 pages.
Liu et al. (2009) "Electrostatically Mediated Liposome Fusion and Lipid Exchange with a Nanoparticle-Supported Bilayer for Control of Surface Charge, Drug Containment, and Delivery." *J. Am. Chem. Soc.* 131: 7567-7569.
Liu et al. (2009) "Porous Nanoparticle Supported Lipid Bilayers (Protocells) as Delivery Vehicles," *Journal of the American Chemical Society* 131(4):1354-1355.
Liu et al. (2012) "Delivering hydrophilic and hydrophobic chemotherapeutics simultaneously by magnetic mesoporous silica nanoparticles to inhibit cancer cells" *International Journal of Nanomedicine* 7: 999-1013.
Liu et al. (2016) "Irinotecan delivery by lipid-coated mesoporous silica nanoparticles shows improved efficacy and safety over liposomes for pancreatic cancer." *ACS Nano* 10:2702-2715 [24 pages—with Supplementary Materials].
Liu et al. (2016) "Irinotecan delivery by lipid-coated mesoporous silica nanoparticles shows improved efficacy and safety over liposomes for pancreatic cancer." *ACS Nano* 10:2702-2715.
Loidl-Stahlhofen et al. (2001) "Multilamellar liposomes and solid-supported lipid membranes (TRANSIL): screening of lipid-water partitioning toward a high-throughput scale" *Pharm. Res.* 18: 1782-1788.
Loidl-Stahlhofen et al. (2001) "Solid-Supported Biomolecules on Modified Silica Surfaces—A Tool for Fast Physicochemical Characterization and High-Throughput Screening" *Advanced Materials* 13: 1829-1834.
Loidl-Stahlhofen et al. (2001) "Solid-supported lipid membranes as a tool for determination of membrane affinity: High-throughput screening of a physicochemical parameter." *J. Pharm. Sci.* 90: 599-606.
Loidl-Stahlhofen et al. (1996) "The thermodynamic control of protein binding to lipid bilayers for protein chromatography" *Nat. Biotechnol.* 14: 999-1002.
Lu et al. (2007) "Mesoporous silica nanoparticles as a delivery system for hydrophobic anticancer drugs." *Small* 3:1341-1346.
Ma et al. (2013) "Nanoparticles for Combination Drug Therapy." *ACS Nano* 7: 9518-9525.
Mackowiak et al. (2013) "Targeted Drug Delivery in Cancer Cells with Red-Light Photoactivated Mesoporous Silica Nanoparticles." *Nano Lett.* 13: 2576-2583.
Mai et al. (2013) "Mesoporous Silica Nanoparticles: A Multifunctional Nano Therapeutic System." *Integr. Biol.* 5: 19-28.
Mayer et al. (2007) "Optimizing Combination Chemotherapy by Controlling Drug Ratios." *Mol. Interventions* 7: 216-223.
Meng et al. (2006) "A Family of Highly Ordered Mesoporous Polymer Resin and Carbon Structures from Organic-Organic Self-Assembly." *Chem Mat* 6(18):4447-4464.
Meng et al. (2010) "Autonomous in Vitro Anticancer Drug Release from Mesoporous Silica Nanoparticles by pH-Sensitive Nanovalves." *J. Am. Chem. Soc.* 132:12690-12697.
Meng et al. (2010) "Engineered Design of Mesoporous Silica Nanoparticles to Deliver Doxorubicin and P-Glycoprotein siRNA to Overcome Drug Resistance in a Cancer Cell Line," *ACS Nano* 4(8):4539-4550.
Meng et al. (2010) "Potent Angiogenesis Inhibition by the Particulate Form of Fullerene Derivatives." *American Chemical Society* 4(5):2773-2783.
Meng et al. (2011) "Aspect Ratio Determines the Quantity of Mesoporous Silica Nanoparticle Uptake by a Small GTPase-Dependent Macropinocytosis Mechanism," *ACS Nano*, 5(6):4434-4447.
Meng et al. (2011) "Use of Size and a Copolymer Design Feature to Improve the Biodistribution and the Enhanced Permeability and Retention Effect of Doxorubicin Loaded Mesoporous Silica Nanoparticles in a Murine Xenograft Tumor Model," *ACS Nano* 5(5):4131-4144.
Meng et al. (2012) "Development of Pharmaceutically Adapted Mesoporous Silica Nanoparticles Platform." *J. Phys. Chem. Lett.* 3: 358-359.
Meng et al. (2013) "Codelivery of an Optimal Drug/siRNA Combination Using Mesoporous Silica Nano-particles to Overcome Drug Resistance in Breast Cancer in Vitro and in Vivo." *ACS Nano* 7: 994-1005.
Meng et al. (2013) "Two-Wave Nanotherapy to Target the Stroma and Optimize Gemcitabine Delivery to a Human Pancreatic Cancer Model in Mice," *ACS Nano* 7(11):10048-10065.
Meng et al. (2015) "Use of a Lipid-Coated Mesoporous Silica Nanoparticle Platform for Synergistic Gemcitabine and Paclitaxel Delivery to Human Pancreatic Cancer in Mice" *ACS Nano* 9(4): 3540-3557.
Messerer et al. (2004) "Liposomal Irinotecan: Formulation Development and Therapeutic Assessment in Murine Xenograft Models of Colorectal Cancer." *Clin Cancer Res* 10(19):6638-6649.
Miao et al. (2014) "Nanoparticles with Precise Ratiometric Co-loading and Co-delivery of Gemcitabine Monophosphate and Cisplatin for Treatment of Bladder Cancer." *Adv. Funct. Mater.* 24(42): 6601-6611. [NIH Public Access; Author Manuscript—24 pages].
Moore et al. (2007) "Erlotinib Plus Gemcitabine Compared with Gemcitabine Alone in Patients with Advanced Pancreatic Cancer: A Phase III Trial of the National Cancer Institute of Canada Clinical Trials Group." *J. Clin. Oncol.* 25(15): 1960-1966.
Mornet, et al. (2005) "The Formation of Supported Lipid Bilayers on Silica Nanoparticles Revealed by Cryoelectron Microscopy." *Nano Lett.*, 5(2): 281-285.
Moura & Carmona-Ribeiro (2003) "Cationic Bilayer Fragments on Silica at Low Ionic Strength: Competitive Adsorption and Colloid Stability" *Langmuir* 19: 6664-6667.
Moura & Carmona-Ribeiro (2005) "Biomimetic Particles: Optimization of Phospholipid Bilayer Coverage on Silica and Colloid Stabilization" *Langmuir* 21: 10160-10164.
Naumann et al. (1992) "Phase transition behavior of single phosphatidylcholine bilayers on a solid spherical support studied by DSC, NMR and FT-IR" *Biophys J.* 63: 1314-1319.
Ng et al. (2001) "One-Step Synthesis of a Fluorescent Phospholipid-Hydrogel Conjugate for Driving Self-Assembly of Supported Lipid Membranes" *Macromolecules* 34: 5759-5765.
Ng et al. (2004) "Properties of a Self-Assembled Phospholipid Membrane Supported on Lipobeads" *Biophys J.* 87: 323-331.
Nordlund et al. (2009) "Formation of supported lipid bilayers on silica particles studied using flow cytometry." *Langmuir* 25, 4601-4606.
Obringer et al. (1995) Antiphospholipid antibody binding to bilayer-coated glass microspheres"" *J Immunol Meth.* 185: 81-93.
Onishi et al. (2003) "Antitumor Properties of Irinotecan-Containing Nanoparticles Prepared Using Poly(DL-lactic acid) and Poly(ethylene glycol)-block-poly(propylene glycol)-block-poly(ethylene glycol)." *Biol. Pharmaceut Bull.* 26(1):116-119.
Onivyde (irinotecan liposome injection)—Highlights of Prescribing Information—Reference ID: 3836766; 18 pages [accessed Oct. 23, 2015]. Retrieved from the Internet: URL: https://www.accessdata.fda.gov/drugsatfda_docs/label/2015/207793lbl.pdf.
Park et al. (2004) "Characterization of radioligand binding to a transmembrane receptor reconstituted into Lipobeads" *FEBS Lett* 567: 344-348.
Pasqua et al. (Published online Feb. 3, 2007) "Preparation of bifunctional hybrid mesoporous silica potentially useful for drug targeting." *Microporous and Mesoporous Materials* 103:166-173.
Patil et al. (2010) "Use of nanoparticle mediated gene silencing and drug delivery to overcome tumor drug resistance." *Biomaterials* 31:358-365.

(56) References Cited

OTHER PUBLICATIONS

Pearse et al. (1987) "Structure and assembly of coated vesicles." *Annu. Rev. Biophys. Biophys. Chem.* 16:49-68.
Peer, et al. (2007) "Nanocarriers as an Emerging Platform for Cancer Therapy." *Nat. Nanotechnol.*, 2: 751-760.
Piyasena et al. (2008) "Biosensors based on release of compounds upon disruption of lipid bilayers supported on porous microspheres." *Biointerphases* 3: 38-49.
Ramsay et al. (2008) "A novel liposomal irinotecan formulation with significant anti-tumour activity: Use of the divalent cation ionophore A23187 and copper-containing liposomes to improve drug retention." *Eur J Pharm Biopharm* 68(3):607-617.
Rapuano & Carmona-Ribeiro (1997) "Physical Adsorption of Bilayer Membranes on Silica" *J. Colloid Interface Sci.* 193: 104-111.
Rapuano & Carmona-Ribeiro (2000) "Supported Bilayers on Silica" *J. Colloid Interface Sci.* 226: 299-307.
Reinl & Bayerl (1993) "Interaction of myelin basic protein with single bilayers on a solid support: an NMR, DSC and polarized infrared ATR study" *Biochim Biophys Acta.* 1151: 127-136.
Reinl & Bayerl (1994) "Lipid Transfer between Small Unilamellar Vesicles and Single Bilayers on a Solid Support: Self-Assembly of Supported Bilayers with Asymmetric Lipid Distribution" *Biochemistry* 33: 14091-14099.
Roggers et al. (2012) "Chemically Reducible Lipid Bilayer Coated Mesoporous Silica Nano-particles Demonstrating Controlled Release and HeLa and Normal Mouse Liver Cell Biocompatibility and Cellular Internalization." *Mol. Pharmaceutics* 9: 2770-2777.
Roiter et al. (2008) "Interaction of Nanoparticles with Liquid Membrane." *Nano Lett.* 8:941-944.
Saad et al. (2008) "Co-delivery of siRNA and an anticancer drug for treatment of multi-drug resistant cancer." *Nanomedicine* 3:761-776.
Sachae et al. (2017) "Surfactant-Templating of Zeolites: From Design to Application" *Chem. Mater.*, 29(9): 3827-3853, [Abstract only—2 pages].
Sackmann, E. (1996) "Supported Membranes: Scientific and Practical Applications." *Science*, 271(5245): 43-48.
Sadzuka et al. (1998) "Effect of liposomalization on the antitumor activity, side-effects and tissue distribution of CPT-11." *Cancer Lett.* 127(1):99-106.
Santos et al. (2009) "The Power of Ultrasound", *Ultrasound in Chemistry: Analytical Applications*, 16 pages.
Schmitt et al. (2001) "Polymer Cushions in Supported Phospholipid Bilayers Reduce Significantly the Frictional Drag between Bilayer and Solid Surface" *Langmuir* 17: 244-246.
Schmitz et al. (1999) "Interactions of Myristoylated Alanine-Rich C Kinase Substrate (MARCKS)-Related Protein with a Novel Solid-Supported Lipid Membrane System (TRANSIL)"*Anal. Biochem.* 268: 343-353.
Schuhmacher et al. (2004) "High-throughput determination of the free fraction of drugs strongly bound to plasma proteins." *J. Pharm. Sci.* 93: 816-830.
Sharma et al. (2004) "Bacteriorhodopsin conjugates as anchors for supported membranes." *Bioconjug. Chem.* 15: 942-947.
Shidhaye et al. (2008) "Nanogel Engineered Polymeric Micelles for Drug Delivery." *Current Drug Therapy* 3(3):209-217.
Singh et al. (2008) "Nanoengineering artificial lipid envelopes around adenovirus by self-assembly." *ACS Nano* 2: 1040-1050.
Slowing et al. (2008) "Mesoporous silica nanoparticles as controlled release drug delivery and gene transfection carriers." *Adv. Drug Deliv. Rev.* 60:1278-1288.
Sommerwerk et al. (2011) "Lipid Coated Chitosan Micro-particles as Protein Carriers." *Pulm. Pharmacol. Ther.* 8: 1978-1984.
Sugahara et al. (2010) "Coadministration of a tumor-penetrating peptiden enhances the efficacy fo cancer drugs." *Science* 328:1031-1035.
Szakacs et al. (2006) "Targeting multidrug resistance in cancer." *Nat. Rev. Drug Discov.* 5:219-234.
Tamanoi "Nanodelivery: Towards controlled release of anti-cancer drugs." Oral Presentation on Dec. 6, 2006 (see NanoBio-Tokyo 2006 Program), 7 pages. Abstract provided in Proceedings of UT Symposium on NanoBio Integration Program and Abstract provided.
Tang et al. (2012) "Mesoporous Silica Nanoparticles: Synthesis, Biocompatibility and Drug Delivery." *Adv Mat* 24(12):1504-1534.
Tardi et al. (2009) "In Vivo Maintenance of Synergistic Cytarabine: Daunorubicin Ratios Greatly Enhances Therapeutic Efficacy." *Leuk. Res.* 33: 129-139.
Tarn et al. (2013) "Mesoporous Silica Nanoparticle Nanocarriers: Biofunctionality and Biocompatibility."*Accounts of Chemical Research* 46(3):792-801.
Thorolfsson et al. (2002) "The binding of tyrosine hydroxylase to negatively charged lipid bilayers involves the N-terminal region of the enzyme." *FEBS Lett.* 519: 221-226.
Torney et al. (2007) "Mesoporous silica nanoparticles deliver DNA and chemicals into plants." *Nat. Nanotechnol.* 2:295-300.
Troutier & Ladaviere (2007) "An overview of lipid membrane supported by colloidal particles." *Adv. Colloid Interface Sci.* 133: 1-21.
Valencia et al. (2013) "Synergistic cytotoxicity of irinotecan and cisplatin in dual-drug targeted polymeric nanoparticles." *Nanomed* 8(5):687-698 [NIH Public Access—Author Manuscript—17pages].
Van Schooneveld et al. (2008) "Improved Biocompatibility and Pharmacokinetics of Silica Nanoparticles by Means of a Lipid Coating: A Multimodality Investigation." *Nano Lett.* 8(8): 2517-2525.
Van Vlerken et al. (2007) "Modulation of intracellular ceramide using polymeric nanoparticles to overcome multidrug resistance in cancer." *Cancer Res.* 67:4843-4850.
Von HOff et al. (2011) "Gemcitabine Plus Nab-Paclitaxel Is an Active Regimen in Patients with Advanced Pancreatic Cancer: A Phase I/II Trial." *J. Clin. Oncol.* 29(34): 4548-4554.
Von HOff et al. (2013) "Increased Survival in Pancreatic Cancer with Nab-Paclitaxel Plus Gemcitabine." *N. Engl. J. Med.* 369(18): 1691-1703.
Wu et al. (2007) "Reversal of multidrug resistance by transferrin-conjugated liposomes co-encapsulating doxorubicin and verapamil." *J Pharm. Pharmaceut. Sci.* 10:350-357.
Xia et al. (2009) "Polyethyleneimine Coating Enhances the Cellular Uptake of Mesoporous Silica Nanoparticles and Allows Safe Delivery of siRNA and DNA Constructs." *ACS Nano* 3(10):3273-3286.
Xu et al. (2013) "Biodistribution and Pharmacokinetics of EGFR-Targeted Thiolated Gelatin Nanoparticles Following Systemic Administration in Pancreatic Tumor-Bearing Mice." *Mol Pharmaceutics* 10:2031-2044.
Yang et al. (2010) "Lipid Coated Mesoporous Silica Nanoparticles as Photosensitive Drug Carriers." *Phys. Chem. Chem. Phys.* 12: 4418-4422.
Yezhelyev et al. (2008) "Proton-sponge coated quantum dots for siRNA delivery and intracellular imaging." *J. Am. Chem. Soc.* 130(28):9006-9012.
Zhang et al. (2011) "Synergistic Antitumor Activity of Gemcitabine and ABT-737 in Vitro and in Vivo through Disrupting the Interaction of USP9X and Mcl-1." *Mol. Cancer Ther.* 10: 1264-1275.
Zhang et al. (2013) "Facile Large-Scale Synthesis of Monodisperse Mesoporous Silica Nanospheres with Tunable Pore Structure" *J. Am. Chem. Soc.*, 135(7): 2427-2430.
Zhang et al. (2014) "Biofunctionalized polymer-lipid supported mesoporous silica nanoparticles for release of chemotherapeutics in multidrug resistant cancer cells." *Biomaterials* 35:3650-3665.
Zhu et al. (2004) "Poly(L-lysine)-modified silican nanoparticles for the delivery of anitsense oligonucleotides." *Biotechnol. Appl. Biochem.* 39:179-187.
Zucker et al. (2009) "Liposome drugs' loading efficiency: A working model based on loading conditions and drug's physicochemical properties." *J Control Release* 139(1):73-80.
AU Office action dated May 22, 2023, in AU Application No. AU2022200881.
Australian Office Action dated Dec. 17, 2020 issued in AU 2017206077.
CA Office Action dated Feb. 3, 2023, in Application No. CA3010711.
CA Office Action dated Oct. 24, 2023, in Application No. CA3010711.
Chinese 2nd Office Action dated May 17, 2021 issued in CN 201780010248.8.

(56) References Cited

OTHER PUBLICATIONS

CN Office Action dated Jan. 30, 2022, in Application No. CN201780010248.8 with English translation.
Daqing Li., et al., "Critical Micelle Concentrations of Cetyltrimethylammonium Chloride and Their Influence on the Periodic Structure of Mesoporous Silica", Colloid Journal of the Russian Academy of Science—Kolloidnyyie Zhurnal, vol. 70, No. 6, Nov. 2008, pp. 747-752, XP0055244840.
EP Extended European Search Report dated Jul. 11, 2023, in Application No. 23158990.4.
EP Partial Supplemental Search Report dated Nov. 11, 2021 in EP Application No. 18897783.9.
European 3rd Office Action dated Sep. 2, 2021 issued in Application No. EP 14 760 467.2.
Extended European Search Report dated Mar. 15, 2022, in Application No. 18897783.9.
Japanese 2nd Office Action dated Aug. 2, 2021 issued in JP 2018-535362.
JP Office Action dated Apr. 17, 2023 in Application No. JP2022-72344 with English translation.
JP Office Action dated Oct. 16, 2023 in Application No. JP2022-72344 with English translation.
Korean Office Action dated May 18, 2021 issued in KR 10-2018-7022622.
KR Office Action dated Mar. 22, 2023 in Application No. KR10-2022-7019372 with English translation.
KR Office Action dated Sep. 25, 2023 in Application No. KR10-2022-7019372 with English translation.
U.S. Advisory Action dated Feb. 7, 2023 in U.S. Appl. No. 16/235,950.
U.S. Final Office Action dated Dec. 16, 2020 issued in U.S. Appl. No. 16/235,950.
U.S. Final Office Action dated Oct. 26, 2023 in U.S. Appl. No. 16/235,950.
U.S. Final office Action dated Sep. 28, 2022 in U.S. Appl. No. 16/235,950.
U.S. Non-Final Office Action dated Apr. 13, 2023 in U.S. Appl. No. 16/235,950.
U.S. Non-Final Office Action dated Jul. 24, 2023, in U.S. Appl. No. 17/384,214.
U.S. Notice of Allowance dated Apr. 21, 2021 issued in U.S. Appl. No. 16/947,539.
U.S. Office Action dated Nov. 19, 2021 issued in U.S. Appl. No. 16/235,950.

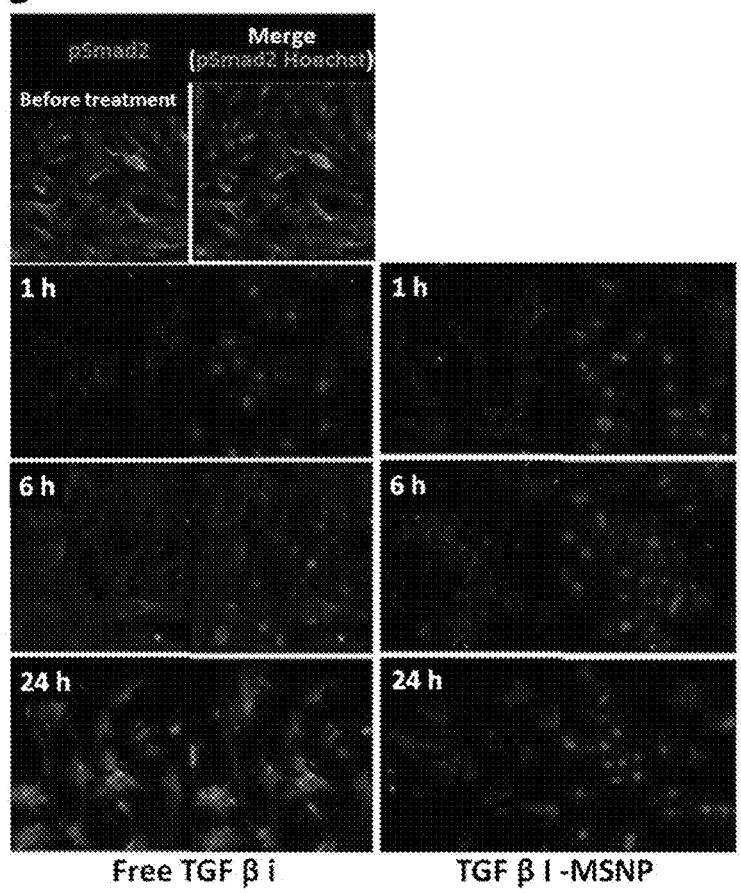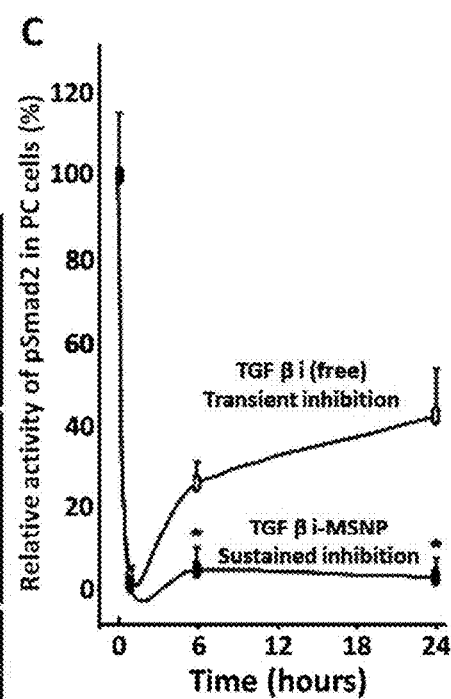
Fig. 2, cont'd.

A

B
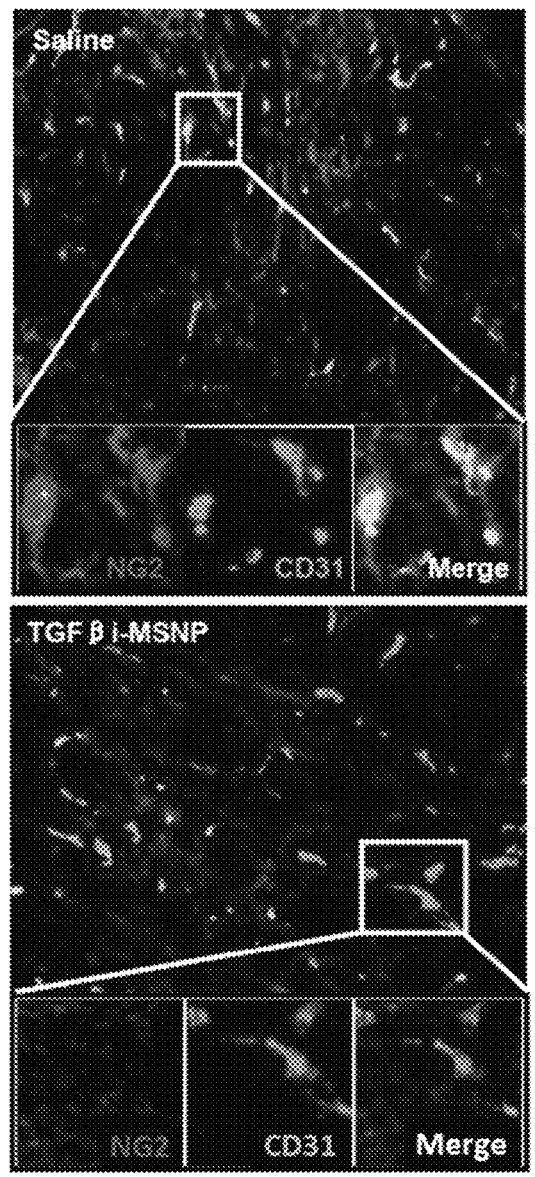
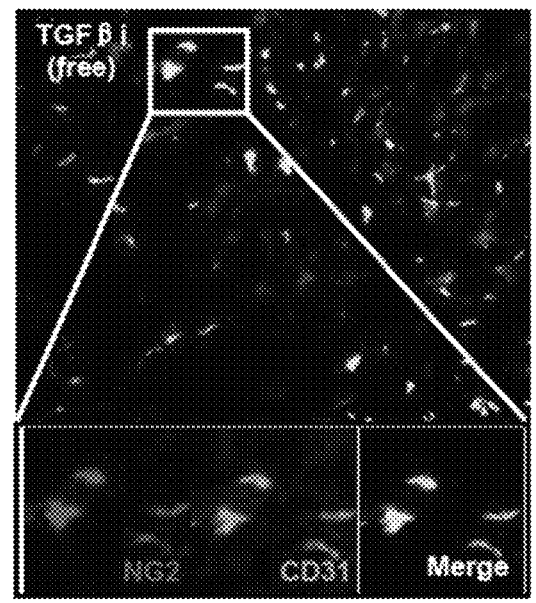
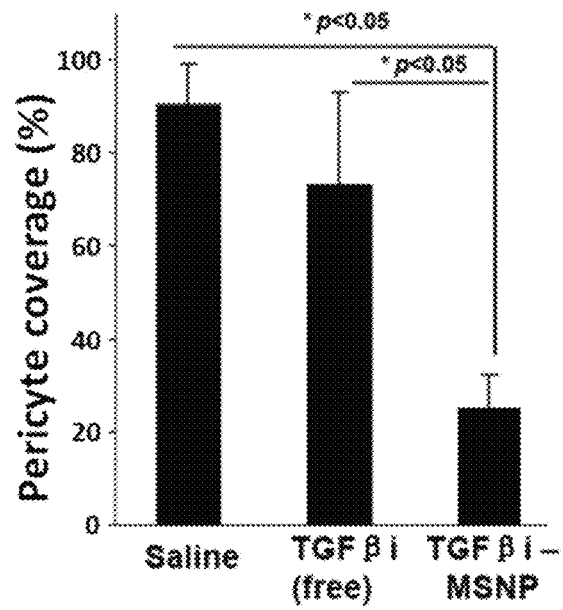
Fig. 3, cont'd.

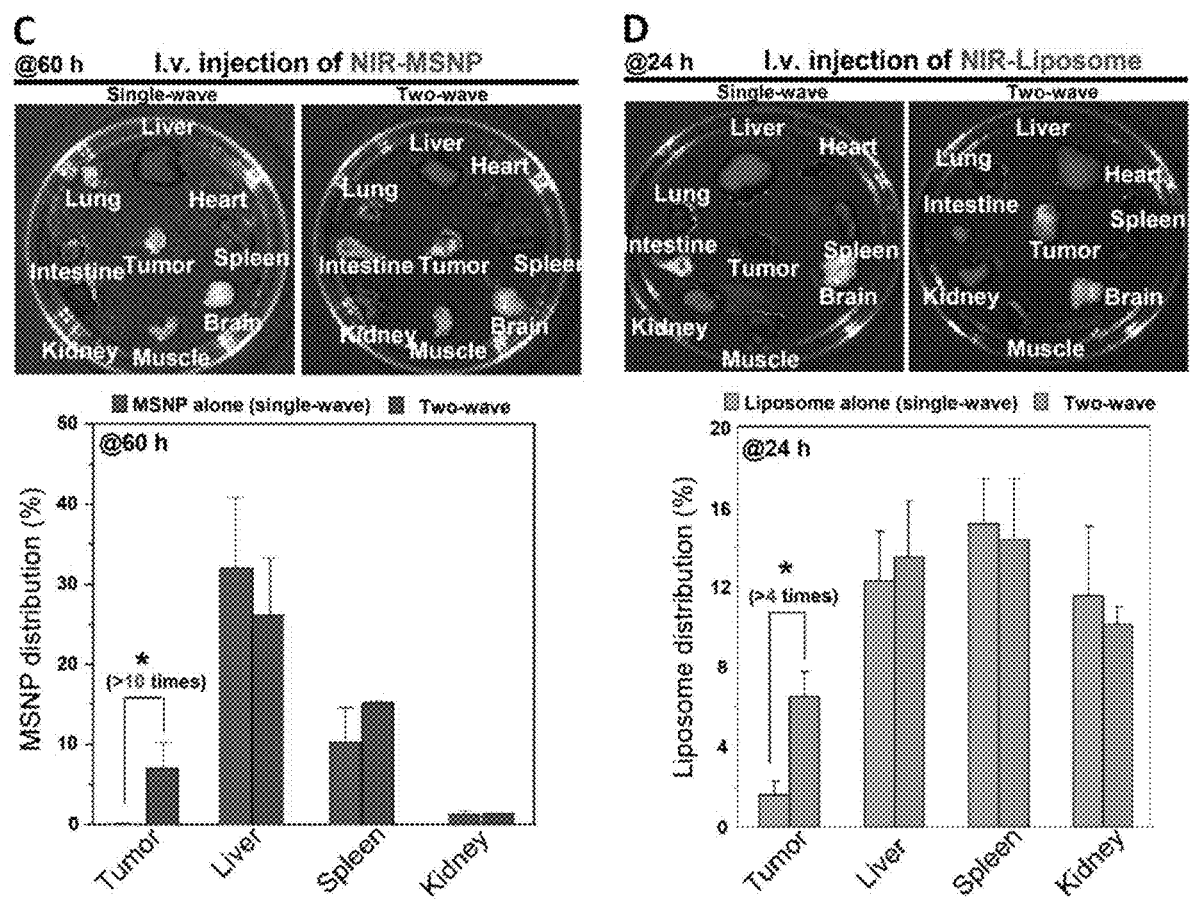
Fig. 5, cont'd.

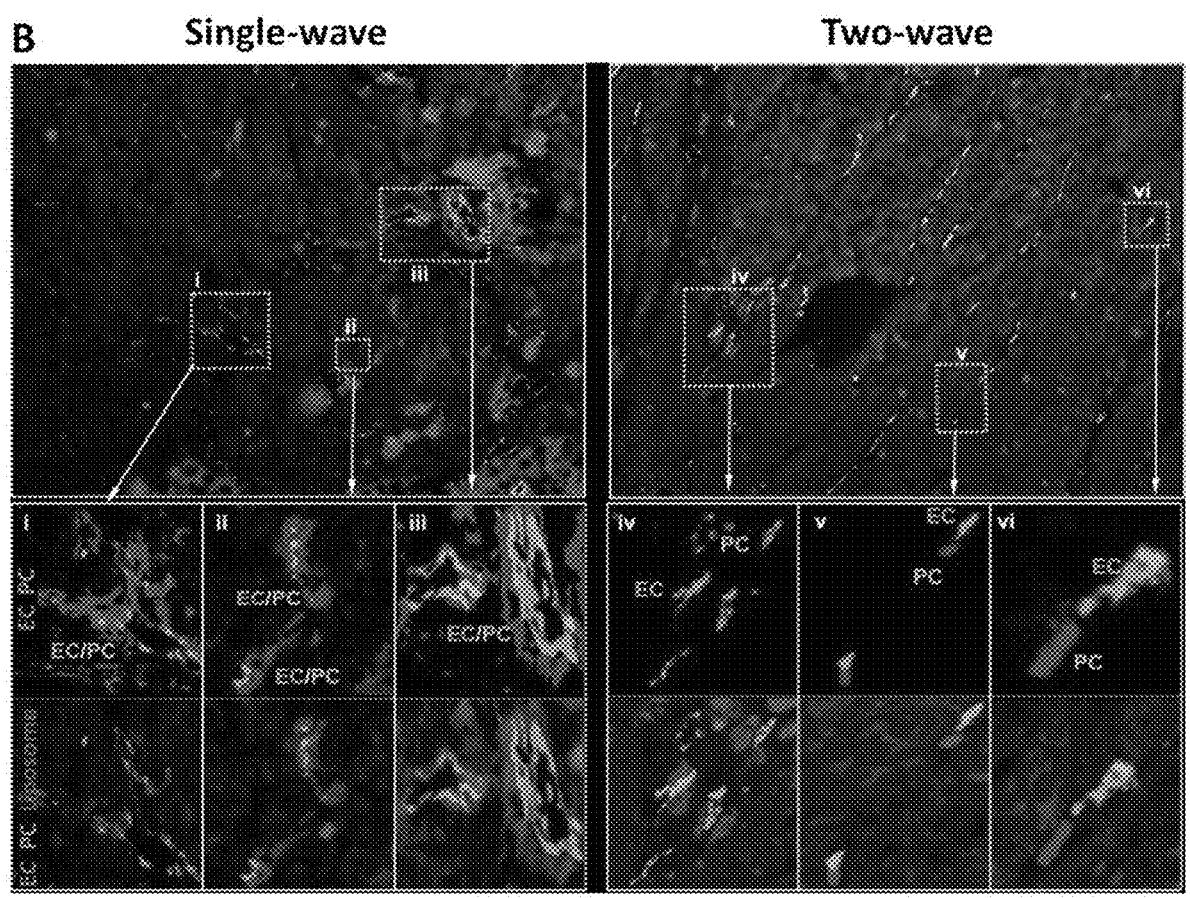
Fig. 6, cont'd.

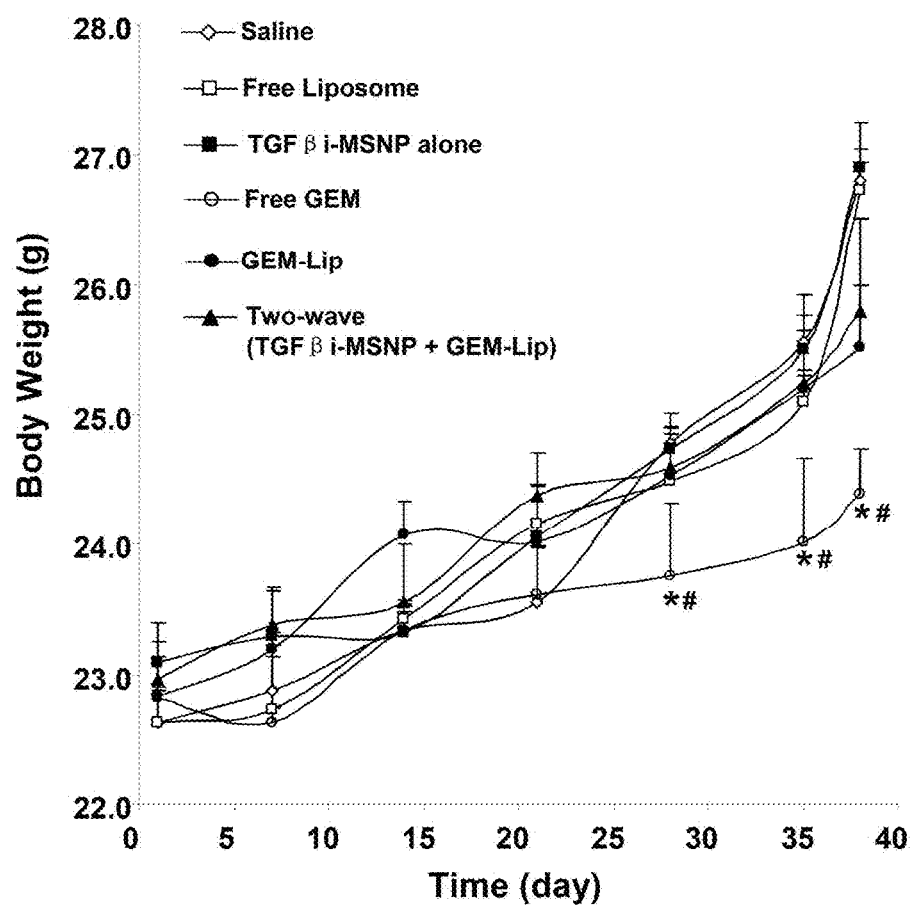
Fig. 7, cont'd.

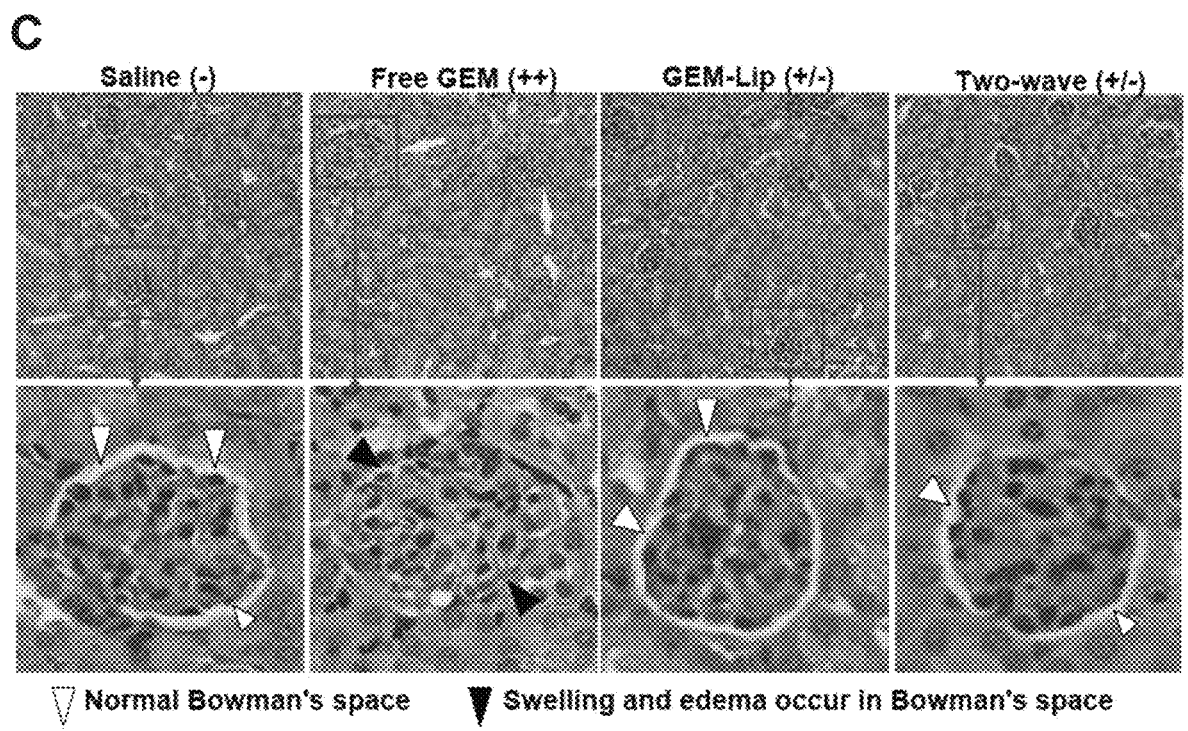
Fig. 7, cont'd.

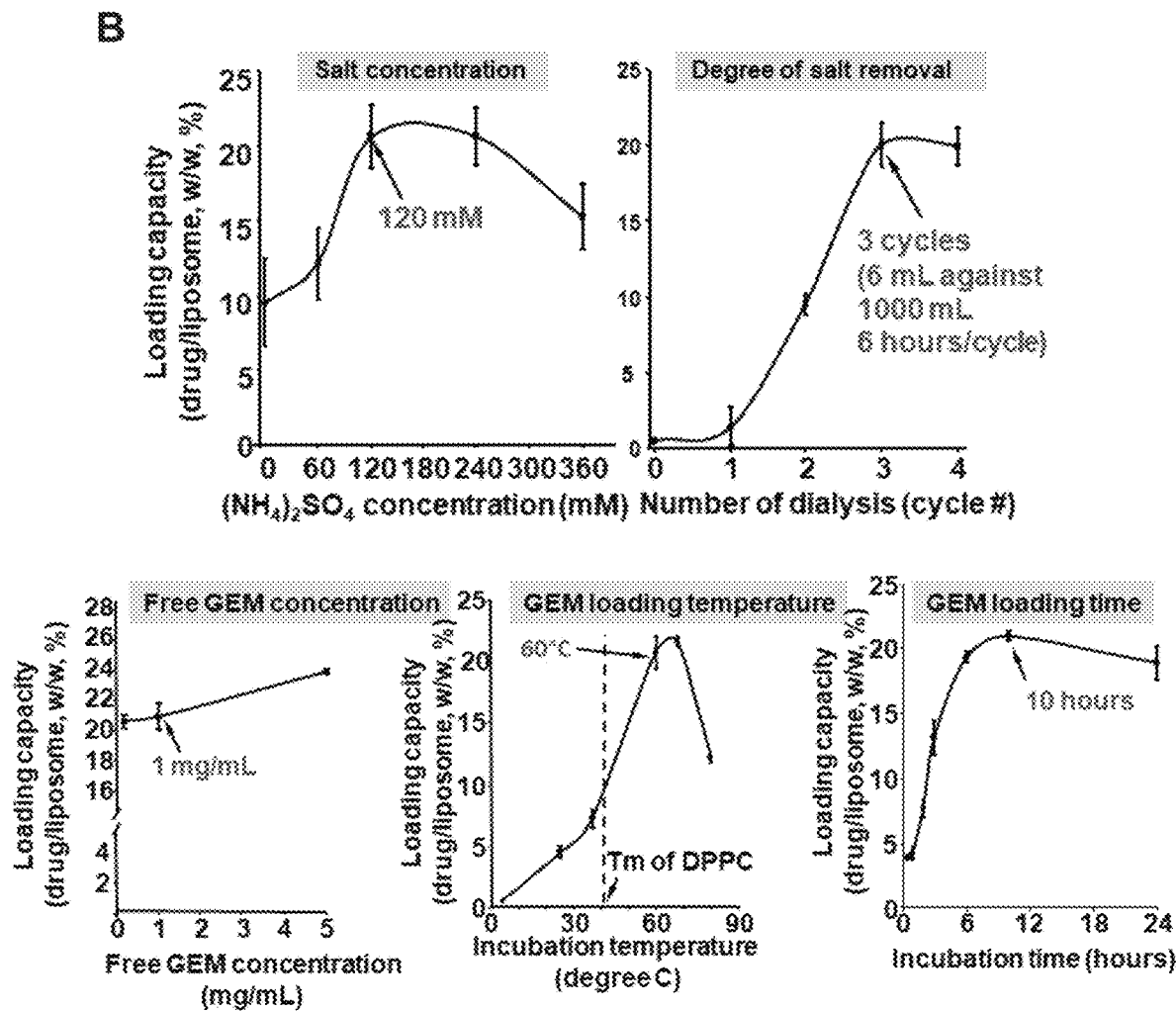
Fig. 10, cont'd.

C
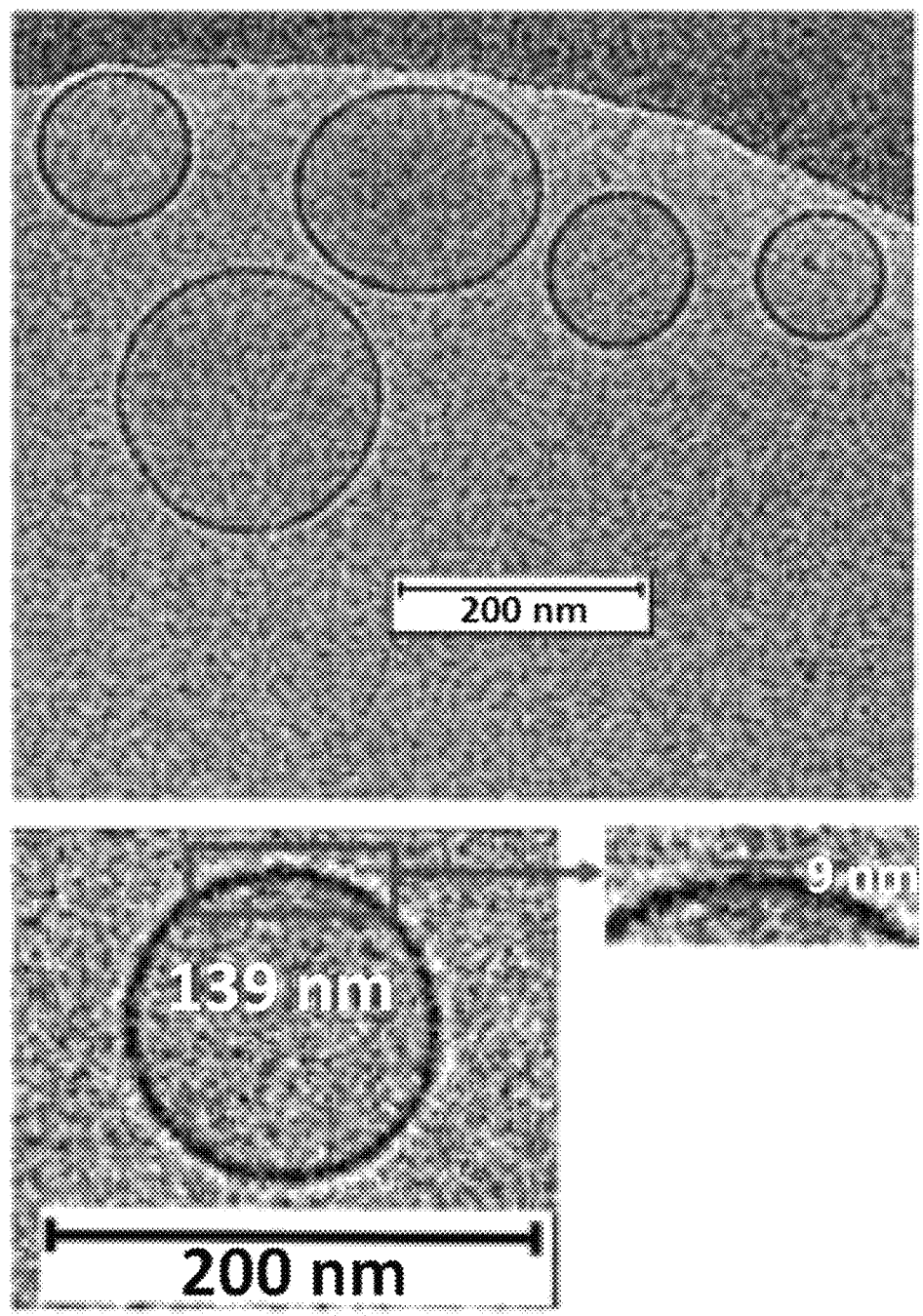
Fig. 10, cont'd.

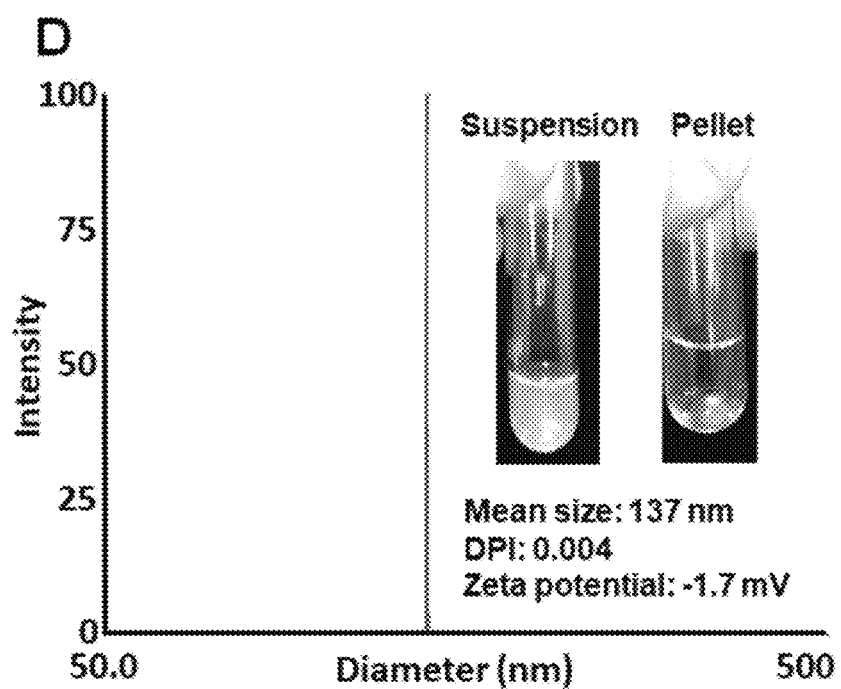
Fig. 10, cont'd.

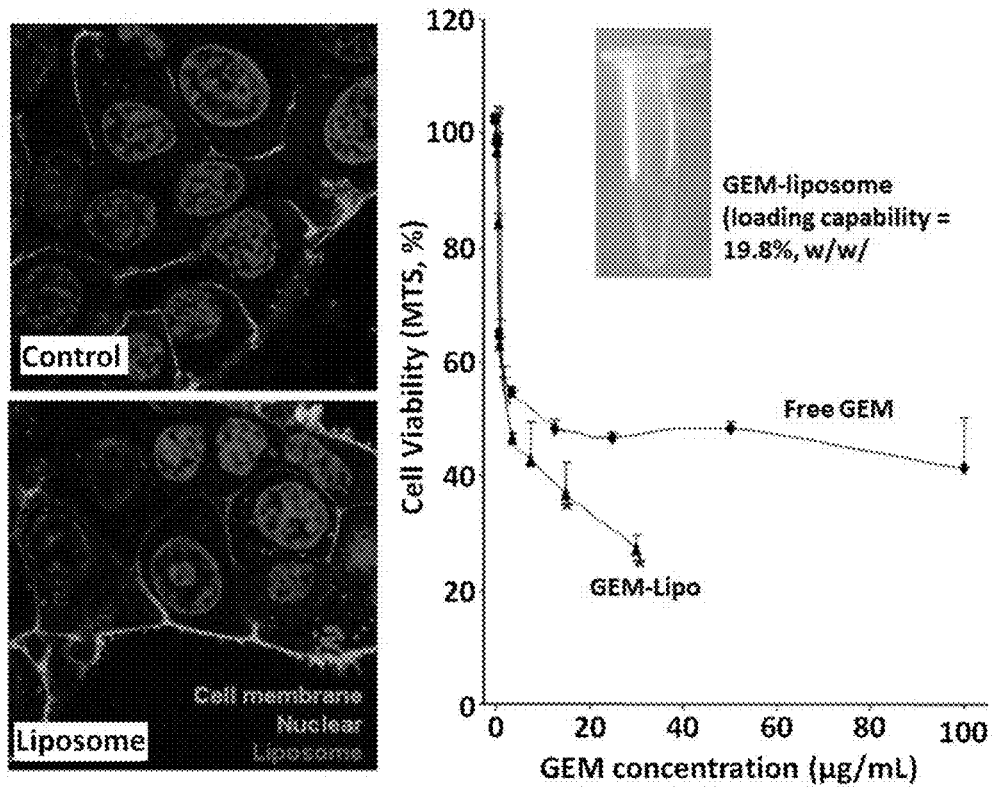
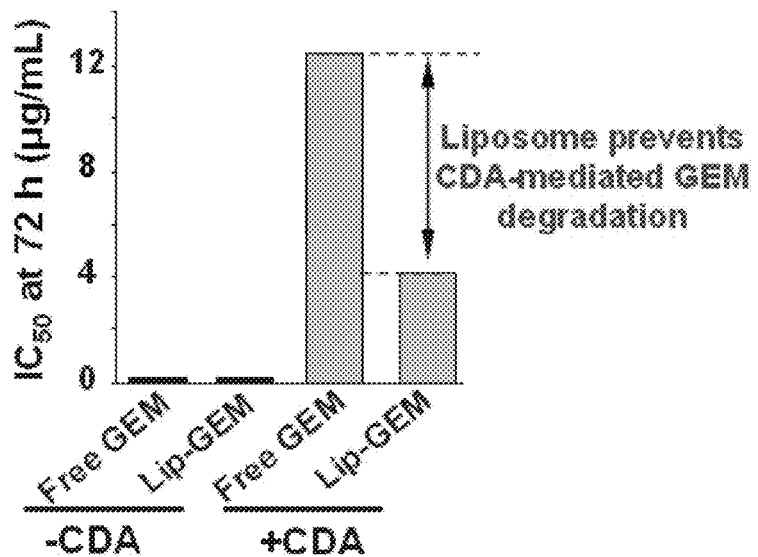
Fig. 10, cont'd.

LIPID BILAYER COATED MESOPOROUS SILICA NANOPARTICLES WITH A HIGH LOADING CAPACITY FOR ONE OR MORE ANTICANCER AGENTS

This application is a continuation of U.S. non-provisional application Ser. No. 14/772,740, filed Sep. 3, 2015, U.S. Pat. No. 10,828,255, which is a U.S. 371 National Phase of PCT/US2014/020857, filed Mar. 5, 2014, which claims priority to and the benefit of the filing date of U.S. provisional application Ser. No. 61/773,013, filed Mar. 5, 2013 and Ser. No. 61/858,388, filed Jul. 25, 2013, all of which are incorporated by reference herein in their entireties.

This invention was made with Government support under Grant No. CA133697 awarded by the National Institutes of Health. The Government has certain rights in the invention.

From the description herein, one skilled in the art can easily ascertain the essential characteristics of this invention, and without departing from the spirit and scope thereof, can make changes and modifications of the invention to adapt it to various usage and conditions and to utilize the present invention to its fullest extent. The following embodiments are to be construed as merely illustrative, and not limiting of the scope of the invention in any way whatsoever. The entire disclosure of all applications, patents, and publications cited herein are hereby incorporated by reference in their entirety, particularly with regard to the subject matter for which they are cited.

BACKGROUND INFORMATION

Human pancreatic ductal adenocarcinoma (PDAC) is the fourth leading cause of cancer-related death in the United States, with a median survival period in PDAC patients of <6 months. While most cultured PDAC cells are relatively sensitive to existing chemotherapeutic agents (e.g. Taxol, 5-FU, and gemcitabine), clinical treatments using free drug or delivery by other means usually fails upon systemic administration.

While the availability of nanocarrier drug delivery systems is promising for cancer treatment due to protected drug encapsulation and targeted delivery, this technology is still at an early stage from the translational medical perspective. One important obstacle is the low or limited loading capacity that is often below the pharmaceutical expectation of a drug delivery carrier. This problem is exemplified in the use of gemcitabine (GEM) that is widely used for treatment of human pancreatic ductal adenocarcinoma (PDAC). GEM has a short half-life in blood stream and therefore its efficacy could be improved by the development of an improved carrier system. Current carriers, such as liposomes and certain submicron structures do not exhibit a sufficient loading capacity to deliver an adequately a cytotoxic dose of GEM at cancer site. For example, a GEM encapsulating liposome has been made by a procedure in which the free drug is added in the step of lipid film rehydration. This conventional protocol usually leads to relatively low drug loading capacity (a yield of <8% (drug/liposome (w/w) drug loading).

There is a need for a carrier system with an improved loading capacity for GEM or other agents that are useful for cancer treatment. Furthermore, there is a need for a carrier system into which can be loaded more than one such agent, particularly one agent that is hydrophobic and one which is hydrophilic.

DESCRIPTION OF THE DRAWINGS

FIG. 11 shows a full panel of NIR mages to cover all the time points in mice injected with 2nd wave NIR-MSNP as shown in FIG. 5A.

DESCRIPTION

Figure 1:
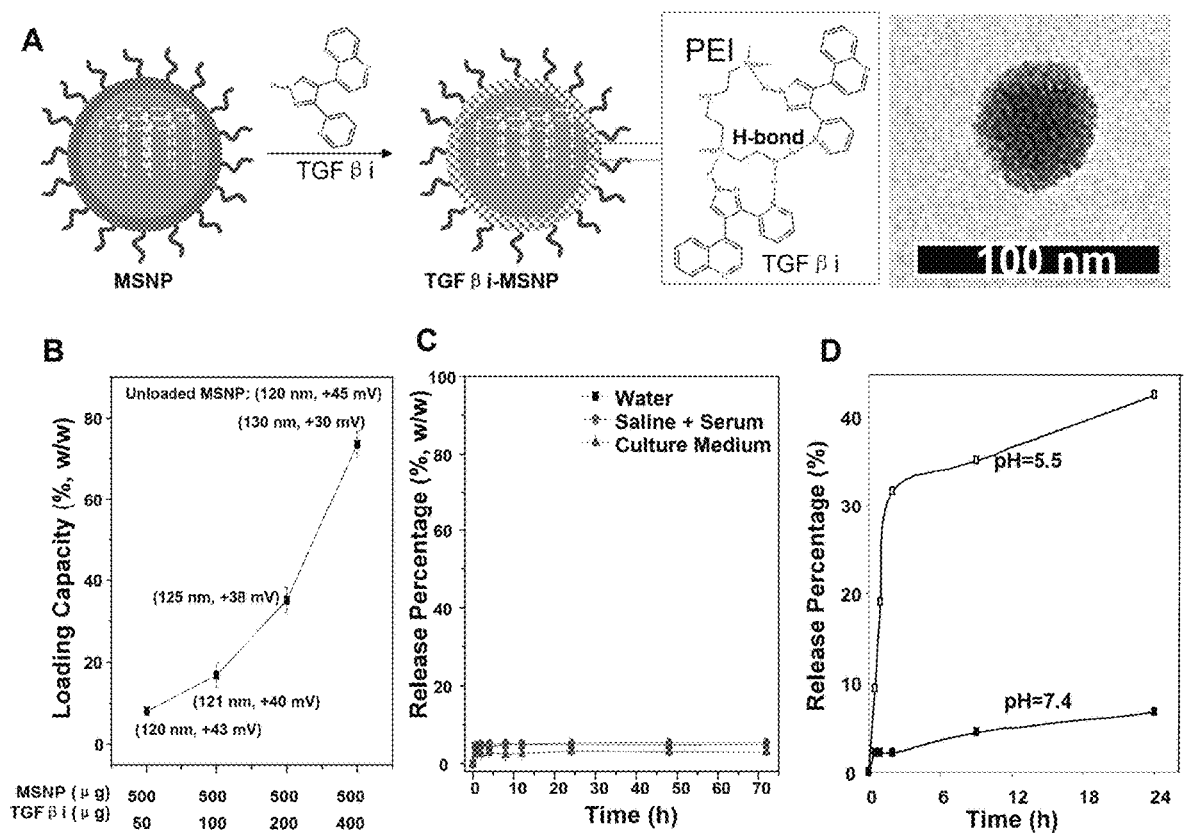
FIG. 1 shows development of an efficient TGFβi carrier by supramolecular attachment to PEI-PEG coated MSNP. (A) A graphical representation of the PEI-PEG copolymer coated MSNP for supramolecular attachment of TGFβi, LY364947, via an H-bond mediated mechanism (see the insert box). TEM image of TGFβi-MSNP was provided. (B) Measurement of the maximum loading capacity of LY364947 in PEI-PEG coated MSNP. Fixed amount of particle (i.e. 500 μg) was used for incubation with incremental amounts (50 to 400 μg) of LY364947 at 25° C. over a 24 h time period. After thoroughly washing in distilled water, the supernatants were separated by centrifugation at 15,000 rpm for 30 min. The loading capacity was quantitatively determined by using the LY364947 OD value of 269 nm (M5e, Molecular Device). Loading capacity (%, w/w)= [(Total minus non-encapsulated weight of LY364947)/ (weight of MSNP)]×100%. Particle size and zeta potential in solution were measured by ZetaSizer Nano (Malvern Instruments Ltd., Worcestershire, UK) and provided in the brackets. (C) Stability of TGFβi attachment in different solutions. TGFβi release was studied in deionized water, saline with 2% serum and DMEM supplemented with 10% FCS at different time points at 37° C. Release percentages were calculated by the following equation: Release percentage (%)=[(the weight of LY364947 in the supernatants)/(the total weight of attached LY364947 at the starting point)]× 100%. (D) TGFβi release was studied in pH=5.5 aqueous solution for 24 h and compared with the release profile in PBS (pH=7.4).

The present invention relates, e.g., to a submicron structure which exhibits a surprisingly large loading capacity for a variety of substances, including small molecules, siRNAs and miRNAs. The submicron structure comprise a silica body defining a plurality of pores that are suitable to receive molecules therein, and having a surface, and a phospholipid bilayer coating the surface, wherein said submicron structure has a maximum dimension of less than one micron (e.g. between about 20 nm and about 300 nm, or between about 50 nm and about 200 nm). This submicron structure is sometimes referred to herein as a "submicron structure of the invention" or as a "mesoporous silica nanoparticle (MSNP)."

The submicron structure can include a silica body defining a plurality of pores that are suitable to receive molecules therein, and having a surface; and a phospholipid bilayer coating the surface; where the submicron structure has a maximum dimension of less than one micron, and where the phospholipid bilayer stably seals the plurality of pores; and wherein the submicron structure is a member of a monodisperse population (of submicron structures).

In embodiments of the invention, the submicron structure further comprises, loaded therein (bound to, encapsulated in, loaded with, into or onto, laden with) an effective amount of at least one of the following categories of therapeutic agents: a) a drug; b) an agent which stabilizes the drug of a) against metabolic degradation; c) an agent which facilitates the delivery of the drug of a) to a target cell, tissue or organ; d) an agent which acts synergistically with the drug of a); or e) one or more additional therapeutic agents, including, for example. nucleic acids (e.g., siRNA or miRNA). In embodiments of the invention, two or more of these categories of therapeutic agents are loaded together into the submicron structure.

For example, the submicron structure can be laden with both the anticancer drug Gemcytabine (GEM) and an agent which leads to inhibition of its degradation, paclitaxel. The two agents act synergistically. One advantage of the submicron particles of the present invention is that they can be loaded, as in this case, with both a hydrophilic molecule (GEM) and a hydrophobic molecule (paclitaxel).

In other embodiments of the invention, the submicron structures are used in a multiwave (e.g. a two wave) method to treat a disease or condition, such as a cancer. For example, in some cancers, such as human pancreatic ductal adenocarcinoma (PDAC), the tumor elicits a dense stromal barrier which includes effective pericyte coverage of tumor blood vessel fenestrations and blocks vascular access of cancer drug laden nanoparticles at the tumor site. In order to combat this blockage, in a first wave, a submicron structure is attached to an inhibitory agent that inhibits blockage or coverage of some or all of the tumor vascular fenestra and removes this pericyte coating. A submicron structure of the invention is administered to a subject to be treated. For example, the agent can be an inhibitor of TGF-β kinase, which is part of the pathway responsible for pericyte adherence to the tumor vascular cells. One typical such inhibitor is LY-3649747 (which not only is a potent inhibitor of the type 1 TGF-β receptor, but whose nitrogen display can, in embodiments of the invention, be used to attach polyethyleneimine/polyethylene glycol (PEI/PEG) copolymer coated MSNP through H-bonding). Other suitable inhibitors of the TGF-β signal pathway include, e.g., SB505124, LY580276, LY550410, and LY364947. In a second wave, an antitumor agent, such as a conventional chemotherapeutic drug, siRNA, or miRNA is administered to the subject, either in a free form, or in a liposome (such as the liposome described herein which has a surprisingly high loading capacity) or in a nanoparticle (such as the submicron structure described herein which is coated with PEI-PEG, or the submicron structure described herein which is coated with a phospholipid bilayer).

In embodiments of the invention, liposomes which are used in the second wave of administration exhibit one or more of the following properties: mono-dispersed unilamellar colloidal vesicles of 100 nm; DPPC:Cholesterol:PEI-PEG=7:2:1; liposomes capable of forming homogenous ~100 nm carriers; ammonium sulphate mediated GEM loading; GEM loading capacity of about 20%; optimal loading by 120 nM $(NH_4)_2SO_4$, 3 cycles of dialysis (6 mL against 1000 mL, 6 hours/cycle), use of 1 mg/mL free GEM, and incubation for 10 hours at 68° C.; stable storage for weeks.

In one embodiment of the invention, the agents for the first and second wave are packaged together in the same submicron structure, which is coated with a phospholipid bilayer. In embodiments of the invention, a third or further waves with additional chemotherapeutic agents, is administered, in which each wave addresses sequential barriers to cancer treatment, so as to achieve an outcome that cannot be achieved by conventional chemotherapy or nanocarriers. The agents for each wave can be delivered independently, or two or more of them can be packaged in a single submicron structure of the invention.

Other advantages of the submicron structures coated with a phospholipid bilayer include monodisperse particle size distribution, which can facilitate uniform cellular uptake of the particles; and control over the dose(s) and ratio(s) of agents delivered together in the submicron structure.

One aspect of the invention is a submicron structure including a silica body defining a plurality of pores that are suitable to receive molecules therein, and having a surface, and a phospholipid bilayer coating the surface, wherein said submicron structure has a maximum dimension of less than one micron, and wherein the phospholipid bilayer stably seals the plurality of pores; and wherein the submicron structure is a member of a monodisperse population.

The term 'monodisperse population' refers to a plurality of particles (e.g., submicron structures) in a colloidal system in which the suspended plurality of particles have substantially identical size and shape. For the purposes of the present invention, a monodisperse population can exhibit a deviation in diameter of 10% rms or less, or 5% rms or less.

The phospholipid bilayer can stably seal the plurality of pores. In other words, submicron structures can retain molecules within the pores for extended periods of time without substantial losses. In some embodiments, molecules can be retained within the submicron structures for 1, 2, 3, 4, 5, 6, or 7 days or more without substantial losses; or for 1 week, 2 weeks, 3 weeks, or 4 weeks or more without substantial losses; or for 1 month, 2 months, 3 months, 4 months, 5 months, or 6 months or more without substantial losses. "Without substantial losses" can refer to a loss of 10% or less; 5% or less; or 2% or less of molecules retained within the pores.

A submicron particle can include about 5% w/w or greater of molecules (for example, therapeutic agents) within the pores; about 10% w/w or greater; about 20% w/w or greater; about 30% w/w or greater; or about 40% w/w or greater. The weight percent of molecules retained within the pores can be referred to as the loading capacity of submicron structures.

Silica Body

The submicron structure includes a silica body that defines a plurality of pores therein. For example, the silica body can be a mesoporous silica nanoparticle. The fact that we refer to the body as a silica body does not preclude materials other than silica from also being incorporated within the silica body. In some embodiments, the silica body may be substantially spherical with a plurality of pore openings through the surface providing access to the pores. However, the silica body can have shapes other than substantially spherical shapes in other embodiments of the current invention. Generally, the silica body defines an outer surface between the pore openings, as well as side walls within the pores. The pores can extend through the silica body to another pore opening, or can extend only partially through the silica body such that it has a bottom surface of the pore defined by the silica body.

In some embodiments, the silica body is mesoporous. In other embodiments, the silica body is microporous. As used herein, "mesoporous" means having pores with a diameter between 2 nm and 50 nm, while "microporous" means having pores with a diameter smaller than 2 nm. In general, the pores may be of any size, but in some embodiments are large enough to contain one or more therapeutic compounds therein. In such embodiments, the pores allow small molecules, for example, therapeutic compound such as anticancer compounds to adhere or bind to the inside surface of the pores, and to be released from the silica body when used for therapeutic purposes. In some embodiments, the pores are substantially cylindrical.

Some embodiments of the invention include nanoparticles having pore diameters between about 1 nm and about 10 nm in diameter. Other embodiments include nanoparticles having pore diameters between about 1 nm and about 5 nm. Other embodiments include particles having pore diameters less than 2.5 nm. In other embodiments, the pore diameters are between 1.5 and 2.5 nm. Silica nanoparticles having other pore sizes may be prepared, for example, by using different surfactants or swelling agents during the preparation of the silica nanoparticles.

The submicron structures according to some embodiments of the current invention may be referred to as nanoparticles. The term nanoparticles as used herein is intended the include particles as large as about 1000 nm. In general, particles larger than 300 nm may be less effective in entering living cells. In some embodiments, colloidal suspensions may be formed using a plurality of submicron structures according to some embodiments of the invention. In that case, larger particles can tend to settle rather than remaining suspended in Brownian motion. As used herein, size of the submicron structure refers to the size of the primary particles, as measured by transmission electron microscopy (TEM) or similar visualization technique. Particle size does not refer to agglomerates in solution or suspension. Some embodiments include nanoparticles having an average maximum dimension between about 50 nm and about 1000 m. Other embodiments include nanoparticles having an average maximum dimension between about 50 nm and about 500 nm. Other embodiments include nanoparticles having an average maximum dimension between about 50 nm and about 200 nm. In some embodiments, the average maximum dimension is greater than about 20 nm, greater than about 30 nm, greater than about 40 nm, or greater than about 50 nm. Other embodiments include nanoparticles having an average maximum dimension less than about 500 nm, less than about 300 nm, less than about 200 nm, less than about 100 nm or less than about 75 nm.

In some embodiments, the surface of the submicron structure or nanoparticle is unmodified. As used herein, an "unmodified" nanoparticle has had no other functional groups added to the surface after formation of the nanoparticle. Unmodified nanoparticles have an anionic charge due to free silyl hydroxide moieties present on the surface.

In embodiments of the invention, the submicron structure further comprises at least one of a valve assembly, a removable stopper assembly or an impeller attached to the submicron structure's proximate or more pores. The submicron structure may comprise at least one of gold or superparamagnetic core. A variety of submicron structures, and methods of making them, are described in, for example, U.S. Patent Application Nos. 2010-0255103, 2010-0284924, 2010-0310465, 2012-0021034, 2013-0046274, and 2012-0207795, each of which is incorporated by reference in its entirety.

Another aspect of the invention is a composition comprising a plurality of submicron structures of the invention, wherein the submicron structures are monodisperse with regard to size and uniformity.

Another aspect of the invention is a method of making a submicron structure of the invention. In a method, a silica body is prepared according to a sol-gel process (see, for example, Xia et al., *ACS Nano*, vol. 3, pp. 3273-3286, 2009; Jie et al., *Small*, vol. 3, pp. 1341-1346, 2007; each of which is incorporated by reference in its entirety). Subsequently, the pores of the silica body are loaded with molecules (e.g., a therapeutic agent). A phospholipid bilayer is then formed on the surface of the silica body, thereby coating the surface. The phospholipid bilayer can stably seal the molecules within the pores of the silica body. Because the molecules are stably sealed within the pores, the submicron structures can have a high loading capacity for the molecules, and the high loading can be stably maintained prior to delivery (e.g., administration to a subject).

Forming the phospholipid bilayer can include contacting a suspension of silica bodies (e.g., pre-loaded silica bodies) with a solution of phospholipids in a suitable solvent. The combined mixture can be supplied with energy (e.g., via sonication) to facilitate coating of the silica body surface with a phospholipid bilayer. Numerous phospholipids suitable for forming bilayers are known, including, but not limited to, 1,2-dioleoyl-3-trimethylammonium-propane (DOTAP), 1,2-dioleoyl-sn-glycero-3-phospho-L-serine (DOPS) and 1,2-dioleoyl-sn-glycero-3-phosphocholine (DOPC). The composition of the lipid bilayer can be adjusted as desired.

In the method, it is not required to pre-form phospholipid liposomes that are contacted with the silica bodies; rather, a preformed film of phospholipids is contacted with the silica bodies. This can avoid the need to carry out a lipid phase exchange, which can complicate the process of forming the submicron structures.

Additional molecules (e.g., therapeutic agents) can be included in the lipid mixture used to form the lipid bilayer coating the silica body. In one embodiment, paclitaxel can be included in the lipid mixture. Thus in some embodiments, the submicron structure can include two or more different molecules, at least one of which is within the pores of the silica body, and at least one of which is associated with the phospholipid bilayer.

In another aspect of the invention, the submicron structure further comprises one or more therapeutic agents. As used herein, a "therapeutic agent" is an agent that, by itself or in conjunction with one or more other therapeutic agents, elicits a measurable amount of a therapeutic effect (e.g., amelioration of a symptom) when administered to a subject.

One category of therapeutic agents that can be administered is a conventional drug, or anticancer agent, such as, e.g., GEM, taxol, doxorubicin, camptothecin, 5-FU, cisplatin, carboplatin or an siRNA or miRNA designed and made by conventional methods to target a nucleic acid which encodes a protein that mediates a cancer.

Another category of therapeutic agents is an agent which stabilizes the drug as noted above, e.g, against metabolic degradation. In addition to administering paclitaxel in order to stabilize GEM, one can administer, e.g., agents which modulate oxidative stress, such a redox cycling chemicals. Other small molecules or siRNAs or miRNAs that target a drug degradation enzyme, such as CDA, can also be used.

Another category of therapeutic agents is an agent which facilitates the delivery of the drug to a target cell, tissue, organ or tumor. For example, as discussed above, in order to remove or reduce stromal or pericyte blockage of tumor vasculature, an inhibitor of the TGF-β pathway, such as inhibitors of the type 1 or type 2 TGF-β receptors and kinases involved in those pathways can be administered. Alternatively or in addition, any of a variety of well-known inhibitors of the TGF-β receptors or post receptor signaling pathways or transcription factors can be used.

Another category of therapeutic agents is an agent that acts synergistically with a drug. In addition to the combination of paclitaxel and GEM, other pairs of synergistic agents can be administered. These include, e.g., siRNA and chemodrugs, (e.g. doxorubicin and Pgp siRNA); paclitaxel and Bcl-2-targeted siRNA; paclitaxel and VEGF siRNA; doxorubicin and Bcl2 siRNA; folfurinox (4drug combination); irinotecan and floxouridine; irinotecan and cisplatin; cytarabine and daunorubicin; doxorubicin and docetaxel; 6-mercaptopurine and daunorubicin; quercetin and vincristine; doxorubicin and phosphatidylinositol-3 kinase inhibitor; gemcitabine and doxorubicin; doxorubicin and a Pgp inhibitor, such as verapamil; cysplatinin or carboplatin plus an aromatase inhibitor; methotrexate and all-trans retinoic acid; and others that will be evident to a skilled worker.

Other therapeutic agents that can be administered by a method of the present invention will be evident to a skilled worker.

A submicron structure (particle) of the invention can be "loaded" with one or more therapeutic agents in a variety of ways. For example, substances such as hydrophilic substances can be incorporated into the pores, e.g. the substance can be introduced into the silica body during the process of forming the silica body, or the substance can be introduced after the silica body has formed. A substance such as a hydrophobic substance can be attached to the phospholipid bilayer which coats the silica particle. The pores can also be loaded by phase exchange with one or a combination of hydrophobic drugs (e.g. paclitaxel), allowing additional hydrophobic drugs to be added to the lipid bilayer.

The "subject" can be any of a variety of animals, including mammals such as domestic animals (pets), laboratory animals, farm animals and humans. In one embodiment, the subject is a human having a cancer. In some embodiments, the subject has a cancer with a heavy stroma and pericyte coverage such as, e.g., PDAC, prostate cancer or a glioblastoma. In embodiments in which an inhibitor of the TFG-β pathway is delivered with a submicron structure of the invention, the subject can have a condition in which TFG-β plays an important role in disease pathogenesis, such as, e.g., neocartilage formation, organ fibrosis and aberrant immune response.

An "effective" amount of a therapeutic agent is an amount that can elicit a measurable amount of a therapeutic effect, such as reduction of a symptom of a disease or condition.

Generally, a submicron structure of the invention is administered to a subject systemically. Suitable routes of administration include, for example, intravenous, intra-arterial, intraperitoneal, intramuscular, or subcutaneous administration.

EXAMPLES

Example IA. Method for Developing a Liposome that Contains a High Loading Capacity for Gemcitabine; Use of a Two-Wave Nanotherapeutics Approach to Overcome Stromal Resistance and Enhance Gemcitabine Delivery in a Human Pancreatic Cancer Xenograft Model While the availability of nanocarrier drug delivery systems is promising for cancer treatment due to protected drug encapsulation and targeted delivery, this technology is still at an early stage from the translational medical perspective. One important obstacle is the low or limited loading capacity that is often below the pharmaceutical expectation of a drug delivery carrier. This problem is exemplified in the use of gemcitabine (GEM) that is widely used for treatment of human pancreatic ductal adenocarcinoma (PDAC). GEM has a short half-life in blood stream and therefore its efficacy could be improved by a nanocarrier such as liposome, provided that the liposome of a sufficient loading capacity could deliver an adequately a cytotoxic dose of GEM at cancer site. A GEM encapsulating liposome has been made by a procedure in which the free drug is added in the step of lipid film rehydration. This conventional protocol usually leads to relatively low drug loading capacity (a yield of <8% (drug/liposome (w/w) drug loading).

The present inventors have found that by creating an ammonium sulfate (($NH_4$)$_2SO_4$) gradient inside the liposome, under optimal conditions, by an active exchange reaction, it is possible to develop an improved drug loading protocol capable of highly efficient GEM encapsulation that generally results in about 20% loading capacity (drug/liposome, w/w). The salt gradient inside the liposome improves GEM loading and leads to a gel-like precipitate of GEM inside the liposome. Without wishing to be bound by any particular mechanism, it is suggested that this high loading occurs because the amphipathic GEM molecule can easily diffuse through the liposome bilayer as un-protonated species, and is subsequently trapped inside the liposome due to a protonation reaction that converts the amphipathic into hydrophilic molecules. The protonated products of less diffusion ability can be stabilized as gel-like drug precipitate (i.e. (GEM-$NH_3$)$_2SO_4$) inside the liposomes.

One method of the invention comprises a rehydration procedure using ammonium sulfate containing solution for loading for GEM. Shown herein are analyses of each parameter during the synthesis and GEM loading, including liposome formulation, ammonium sulfate concentration, extent of salt removal, drug loading time, temperature, amount of free GEM, etc. Advantageously, the loading approach also leads to improved drug stability inside the liposome. Other agents that are structurally similar to GEM can also be efficiently encapsulated into liposomes by a method of the present invention.

Due to the high loading ability including the potential of liposome modification (i.e. PEG, active ligand, fluorescent labeling, etc), this liposomal GEM delivery platform exhibits its good cancer killing ability both in vitro and in vivo. Moreover, the GEM-laden liposome will be an ideal "second wave" particle that can be used in the multi-wave PDAC therapy, as described elsewhere herein.

Aspects of this embodiment include the following:
1. A liposome comprising at least about 20% gemcitabine (GEM)/lipid (wt/wt), wherein the GEM is in the form of a gel-like precipitate (e.g. (GEM-$NH_3$)$_2SO_4$). In embodiments of the invention, the liposome is further modified (e.g. with PEG, an active ligand, fluorescent label, etc.).
2. A method for making a liposome comprising about at least about 20% gemcitabine (GEM)/lipid (wt/wt), wherein the GEM is in the form a gel-like precipitate (e.g. (GEM-$NH_3$)$_2SO_4$), the method comprising (a) hydrating a thin lipid film (e.g., using the formulation DPPC:Cholesterol:DSPE-PEG2K=7:2:1) in the presence of about 120 nM ($NH_4$)$_2SO_4$ to form a liposome comprising an ammonium sulfate gradient, then (b) loading GEM into the liposome (e.g. by an equilibration method).

This method can comprise
preparing a lipid film,
hydrating the lipid film in a buffer comprising about 120 nM ($NH_4$)$_2$SO4 to form a liposome comprising an ammonium sulfate gradient,
removing non-encapsulated salts from the liposome (e.g., by about 3 dialysis cycles against about 1000 mL, for about 6 h/cycle), then
incubating the liposomes with free GEM (e.g. at a concentration of about 1 mg/mL at about 60° C., for about 10 h), and
removing non-encapsulated GEM.
3. A method for introducing GEM into a cell (in vitro or in vivo, e.g. from or in a subject having a cancer, such as pancreatic cancer), comprising contacting the cell with a liposome of claim 1, under conditions that are effective for efficient delivery of the liposome into the cell. In one embodiment of the invention, the method is for treating a tumor in pancreatic cancer, such as human pancreatic ductal adenocarcinoma (PDAC), wherein the method further comprises (a) in a first wave, inhibiting the tumor TGF-β signaling pathway by contacting the tumor with a TGF-β inhibitor laden mesoporous silica nanoparticle (MSNP) capable of manipulating the human pancreatic ductal adenocarcinoma (PDAC) tumor microenvironment by releasing a small molecule inhibitor, such as LY-364947 ($C_{17}H_{12}N_4$), thereby removing pericyte coverage from the tumor, then (b) in a second wave, contacting the tumor with the liposome comprising GEM.

Abstract

Pancreatic cancer elicits a dense stromal response in which pericyte coverage of tumor vasculature presents a barrier that interferes with liposomal delivery of gemcitabine. In order to improve liposomal delivery, we used a mesoporous silica nanoparticle to deliver a small molecule inhibitor of the TGF-β pathway to decrease pericyte coverage and improve gemcitabine delivery to a human xenograft tumor. This dual wave approach provided effective tumor cell killing compared to free drug or liposome-encapsulated drug, thereby demonstrating the utility of an engineered approach to stromal drug resistance.

Introduction

Human pancreatic ductal adenocarcinoma (PDAC) is the fourth leading cause of cancer-related death in the United States, with a median survival of <6 months.[1] Since PDAC is typically diagnosed at a late stage, many PDAC cases cannot be considered for surgery because of metastases and local spread to the superior mesenteric blood vessels at the time of diagnosis.[2, 3] While chemotherapy is often the only option, even this form of treatment is characterized by poor efficacy and severe side effects in PDAC patients. While most cultured PDAC cells are relatively sensitive to chemotherapeutic agents such as gemcitabine (GEM), Taxol, and 5-FU, clinical treatment is often unsuccessful because of the dense stromal barrier, which is a histological hallmark of PDAC as compared to other cancer diseases.[4] The desmoplastic stroma is comprised of a dense extracellular matrix, as well as a variety of non-cancerous cells, including the presence of pericytes that blocks vascular fenestrations and prevents vascular access of cancer drugs and other therapeutic agents 0.4 This includes interference in the delivery of drug-laden nanocarriers in animal PDAC models.[5-8] Pericyte coverage of more than 70% of the tumor vasculature significantly differentiates PDAC from other cancer types that exhibit a less dense stroma, e.g., glioblastoma or renal carcinoma in which the pericyte coverage is limited to 10~20% of the blood vessels.[4-6] Mammary and colon carcinoma fall somewhere in between.[4-6] Thus, the development of efficacious and safe chemotherapy for PDAC is a big challenge.

A number of strategies have been entertained to improve the efficacy of delivery of chemotherapy and decreasing drug side effects in PDAC. These efforts have included improvement of the pharmacokinetic profile, tumor-specific targeting and attempts to overcome the resistance of the stromal barrier.[9-12] One promising approach is to take advantage of the ability of nanocarriers to encapsulate and deliver chemotherapeutic agents to improve the stability and cytotoxic killing of PDAC cells. For instance, free GEM, which is a first-line chemotherapeutic agent for PDAC, has a very short half-life in vivo and can be rapidly decomposed by a cytidine deaminase (CDA) degradation in the circulation and at the tumor site.[13] Use of nano carrier, such as unilamellar pegylated liposome, has been shown to increase GEM plasma half-life and intratumoral drug concentration to the extent that a 10 times lower drug dose could be used for tumor inhibition in mice, without signs of toxicity.[11] An additional exciting advance with the introduction of nanocarriers is the potential to target the stromal chemoresistance pathway that interferes in tumor vascular access. For penetration of anticancer drugs, either in their free or nanocarrier format, is an important factor limiting drug efficacy and bioavailability at the PDAC site.[14] Tumor angiogenesis is controlled by a number of growth factor pathways, including the important role of the transforming growth factor beta (TGF-β) pathway in promoting pericyte coverage.[15] TGF-β stabilizes capillary-like structures during neo-angiogenesis and is also responsible for the differentiation of mesenchymal cells into pericytes (PCs) that cover endothelial cells (ECs), leading to the formation of intact blood vessels.[16, 17] Thus, TGF-β signaling inhibition presents one of the promising targets to affect change in the vascular access of cancer drugs and nanocarriers to tumor sites.[7, 18] Vascular access can also be improved by reducing the collagen content of the vasculature and stroma throughout the tumor interstitium.[19]

The program is discussed above now allows us to propose an engineered approach to PDAC drug delivery through the use of nanocarriers that provide protected encapsulation as well as improving vascular access through targeting of stromal elements. By combining these principles, we propose a two-wave therapeutic procedure in which the first step is to gain vascular access by a mesoporous silica nanoparticle (MSNP) nanocarrier that inhibits the TGF-β pathways by delivering a small molecule inhibitor (LY364947), also referred to as "TGFβi", followed by subsequent delivery of a liposome that has been optimized for efficient GEM encapsulation and delivery. In this communication, we provide proof-of-principle testing to demonstrate that it is possible to enhance GEM delivery to a human pancreatic xenograft in a nude mice model. We demonstrate the development of a MSNP carrier that can be used for supramolecular attachment of TGFβi, including the ability of this carrier to interfere in PCs recruitment to ECs in vitro and to a human xenograft PDAC tumor in vivo. We demonstrate that this carrier can effectively enhance vascular access of a $2^{nd}$ wave of GEM-loaded liposomes to the same tumor in vivo. We demonstrate that GEM loading in this liposome can be dramatically increased by creating an ammonium sulfate gradient inside the liposome which through GEM protonation could increase its transport from the incubation medium. We went on to demonstrate increased therapeutic efficacy and reduced side effects of this dual wave platform in relation to free GEM.

Results

Development of an Efficient TGFβi Carrier by Supramolecular Attachment to MSNP

The highly coordinated action of various growth factors, including heterotypic PCs interaction with ECs, leads to the formation and stabilization of tumor blood vessels.[20] In this complex regulation, TGF-β, a well-known vasculature modulator, regulates various processes leading to vessel maturation, inhibition of ECs proliferation and migration, induction of PCs differentiation, and maintaining the integrity of the microvasculature[20-22] Use of medicinal chemical synthesis and screening, the extensive knowledge of TGF-β signal transduction pathway has led to the development of a group of compounds that can interfere in signaling by the TGF-β receptor-I, such as SB505124, LY580276, LY550410, and LY364947. LY364947, a nitrogen heterocyclic compound (FIG. 1A), is a potent inhibitor of the receptor-associated SMAD kinase in vitro and in vivo test.[23-25] The electronegative nitrogen atoms in LY364947 introduce the opportunity to use supramolecular or electrostatic chemistry for attachment to a functionalized nanocarrier surface. Such an opportunity presented itself for our multifunctional MSNP platform that has previously been developed for protected and efficient systemic delivery of a variety of cargoes to cancer cells and xenograft tumors in mice.[26-32] This includes the development of a 50 nm MSNP core that is coated with a polyethyleneimine-polyethylene glycol (PEI-PEG) copolymer, which presents free amine groups that could be H-bonded to the nitrogen group on the inhibitor (FIG. 1A). Another advantage of this carrier is that the PEI-PEG coating is stably attached, provides monodispersion of MSNP in blood and decreases update by the reticuloendothelial system, so as to allow a long circulatory half-life and effective delivery of drugs and/or siRNA to breast and cervical tumor sites.[28, 31] To assess the potential effectiveness of the copolymer-coated MSNP to deliver LY364947, we used fixed amount of particle (i.e. 500 µg) for incubation with incremental amounts (50 to 400 µg) of the kinase inhibitor at 25° C. over a 24 h time period. After thoroughly washing in distilled water, the loading capacity was quantitatively determined by using the LY364947 OD value of 269 nm. This demonstrated a maximum drug loading capacity of ~74% (inhibitor/particle, w/w), which reflects the abundance of H-binding donors and acceptors on PEI and the inhibitor, respectively (FIG. 1 B). Moreover, the soft structure of PEI facilitates conformational changes that allow strong hydrogen bonding and incorporation of the drug on the particle surface (FIG. 1B). This leads to a slight increase in the hydrodynamic particle size from 120 nm to 130 nm at the maximum loading capacity for the inhibitor. While the non-drug bonded MSNP exhibited a zeta potential value of +45 mV in water, binding of the drug inhibitor decreased this value to +30 mV (FIG. 1B). FIG. 1C demonstrates that the drug-bound particles are stably suspended in water, saline (plus 2% serum) and cell culture medium for 72 h. A subsequent release study showed that the TGFβi could be released from the MSNP in a time-dependent manner by lowering of the pH of the solution to 5.5 (FIG. 1D). Approximately 40% weight percentage TGFβi could be released within 24 h.

TGFβi-Loaded MSNP Disrupts PC Interactions with EC In Vitro and In Vivo

Figure 2:
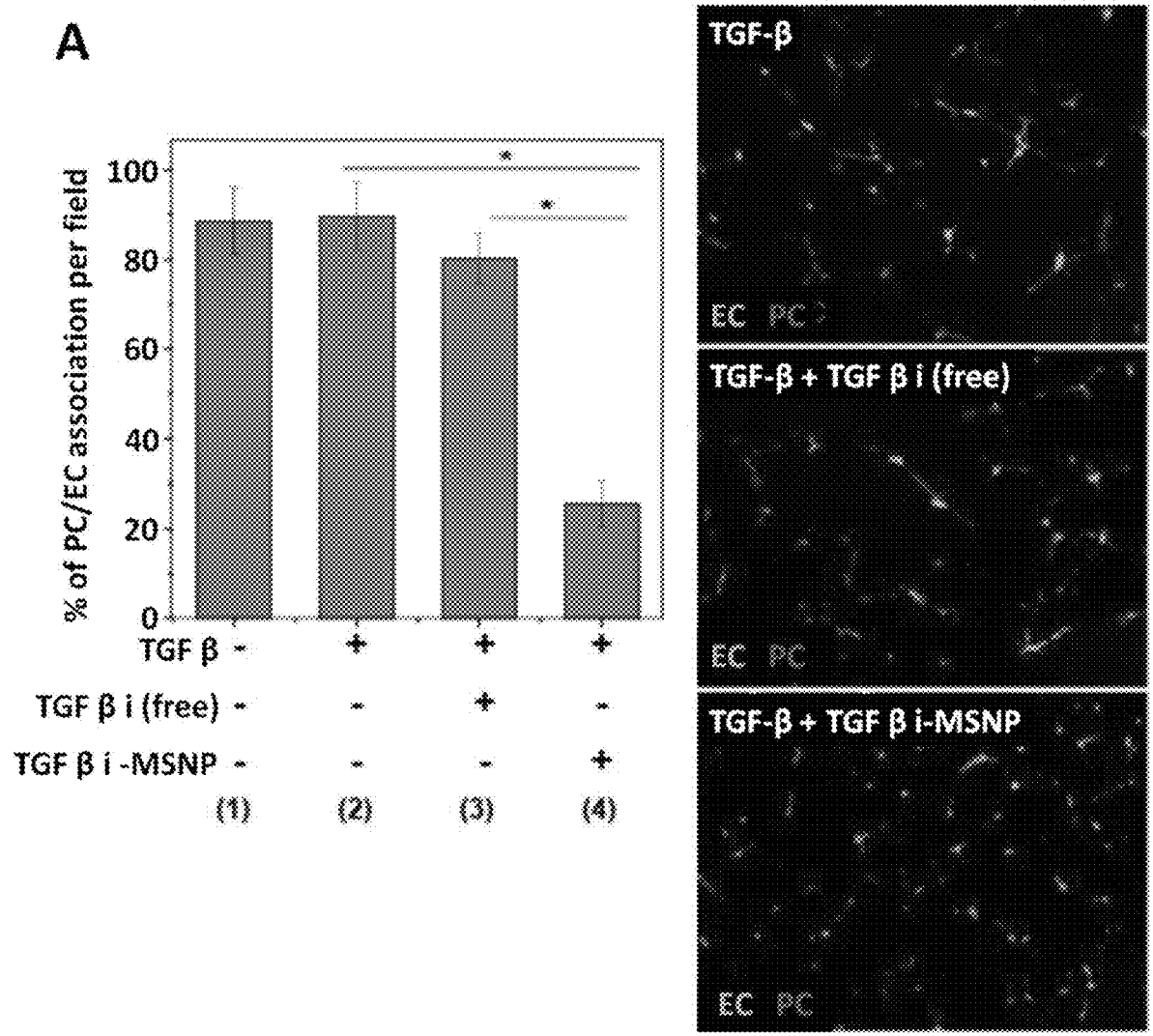
FIG. 2 shows TGFβi-loaded MSNP disrupts PC interactions with EC in vitro. (A) HDME cells (104 cells/mL) and HSM cells (5×103 cells/mL) were first stained by CellTracker™ Green CMFDA (Invitrogen, Grand Island, NY) and CellTracker™ Red CMTPX (Invitrogen, Grand Island, NY) according the manufacture's instruction 24 h before experiment. After live cell staining, ECs were treated with 2 ng/mL of TGF-β for 3 h and PCs were treated with free TGF-β or TGFβi-MSNP at inhibitor dose of 1 μM for 3 h. Subsequently, both cell types were co-cultured in Matrigel-coated 6-well plates for further incubation of 16 h at 37° C. PC/EC adhesions were quantitatively determined from five fields of three independent samples with the fluorescent microscope (Zeiss, Germany). *, P<0.05. (B) Use of immunofluorescence assay to determine the level of Smad2 phosphorylation. PCs were seeded in 8-well chamber slides. 16 h post cell seeding, PCs were treated with 2 ng/mL TGF-β for 3 h. Subsequently, the cells were treated with TGFβi-laden MSNP at the inhibitor dose of 1 M for 1-24 h. For comparison, free TGFβi was used to treat the cells at same dose. The treated cells were fixed, permeabilized, and incubated with primary antibody of anti-pSmad2 at 4° C. for 16 h. After PBS washing, the samples were further incubated with FITC-conjugated secondary antibody. The nucleus was stained by Hoechst 33342. The slides were visualized under a fluorescence microscope. (C) The signal intensity of the green channel, reflecting activated Smad2 (pSmad2), was calculated by Image J software (version 1.37c, NIH). *, P<0.05.

To investigate the effects of TGFβi on the co-migration of cultured human vascular smooth muscle cells (used as a surrogate PC) with human microvascular EC, we used a Matrigel assay[33] to compare the effect of TGFβi-loaded MSNP with the free inhibitor (FIG. 2). ECs and PCs were stained with CellTracker™ Green and CellTracker™ Red, respectively. FIG. 2A demonstrates that the percentage of PC/EC association was significantly inhibited if the TGFβi was delivered by MSNP as compared to the inhibitory effect of free inhibitor at 1 µM. Representative fluorescent images of the cellular co-migration are shown on the right hand side of the figure. Upon binding to type I/II TGF-β receptors, the growth factor induces the phosphorylation of the C-terminal SXS motif of the-associated kinases, Smad2 and Smad3[34] Looking at Smad2 phosphorylation in PCs, we used an immunochemical technique that discerns anti-pSmad2 by a secondary FITC-conjugated antibody under a confocal microscope (FIG. 2B).[35] This demonstrated efficient and sustained inhibition of Smad2 phosphorylation for up to 24 h in PCs treated with TGFβi-MSNP compared to cells exposed to free inhibitor, which only suppressed pSmad2 for 6 h (FIG. 2). Quantitative assessment of the green fluorescence intensity by Image J software confirmed a statistically significant and sustained inhibition of Smad2 phosphorylation by TGFβi-MSNP (FIG. 2C).

Figure 3:
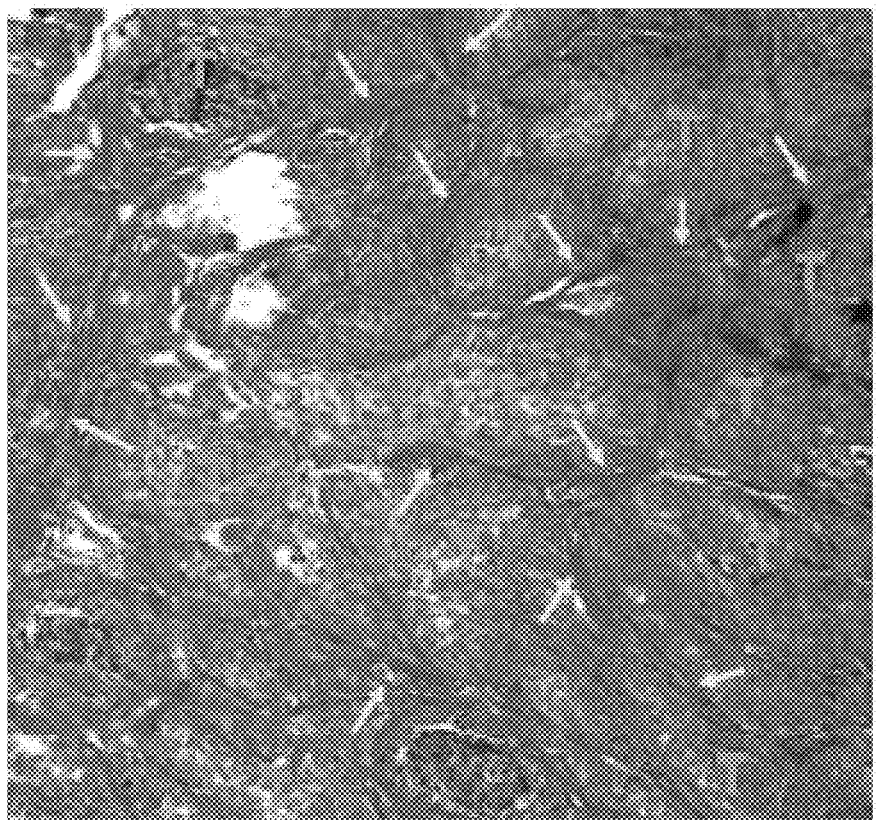
FIG. 3 shows TGFβi-loaded MSNP disrupts PC interactions with EC in BxPC3 xenograft. (A) The tumor section was visualized by a Masson's trichrome staining, which showed a dense stroma including the heavy collagen deposition in blue in BxPC3 xenograft. "T" indicates tumor cells. Arrows point out stroma. (B) Tumor-bearing animals (tumor size of 0.8~1.0 cm in diameter) were divided into two groups and received i.v. injection of TGFβi-MSNP at inhibitor dose of 1 mg/kg (MSNP dose of 2 mg/kg). Saline and i.v. injection of free inhibitor at same dose were used as control. Tumor tissues were quickly collected 1-2 h post injection and OCT embedded for frozen section and dual color immunohistochemistry staining. The procedure of the staining was provided in the method section. This dual color staining that labels EC maker CD31 in green (FITC) and PC maker NG2 in red (Alexa fluor 594) were used to compare the effect of tumor blood vessel integrity and quantify the extent of PC/EC association. Zoom-in images were provided at higher magnification to show the extent of PC/EC association in each group. PC covered EC were quantified in three random fields in each group. *, $P<0.05$.
Figure 4:
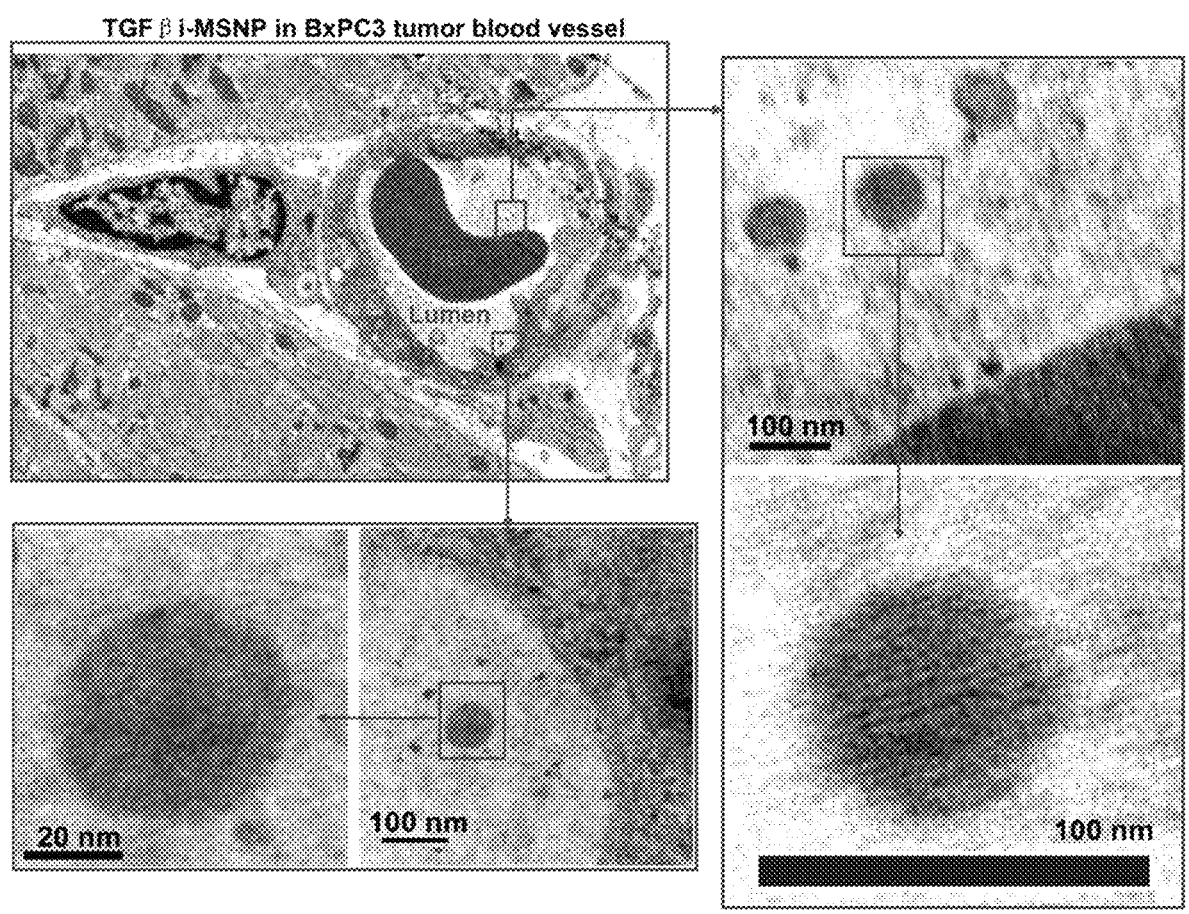
FIG. 4 shows TEM ultrastructural analysis to elucidate the MSNP mediated TGFβi delivery in BxPC3 xenograft. Electron microscopy to determine the ultrastructure in BxPC3 tumor following administration to TGFβi-MSNP for 2 h. RBC denotes red blood cell. Electron microscopy was powerful enough to capture the porous structure of TGFβi-MSNP inside the tumor tissue, an ultrastructural feature that has not previously been accomplished. Additional TEM images are displayed in FIG. 9.
Figure 9:
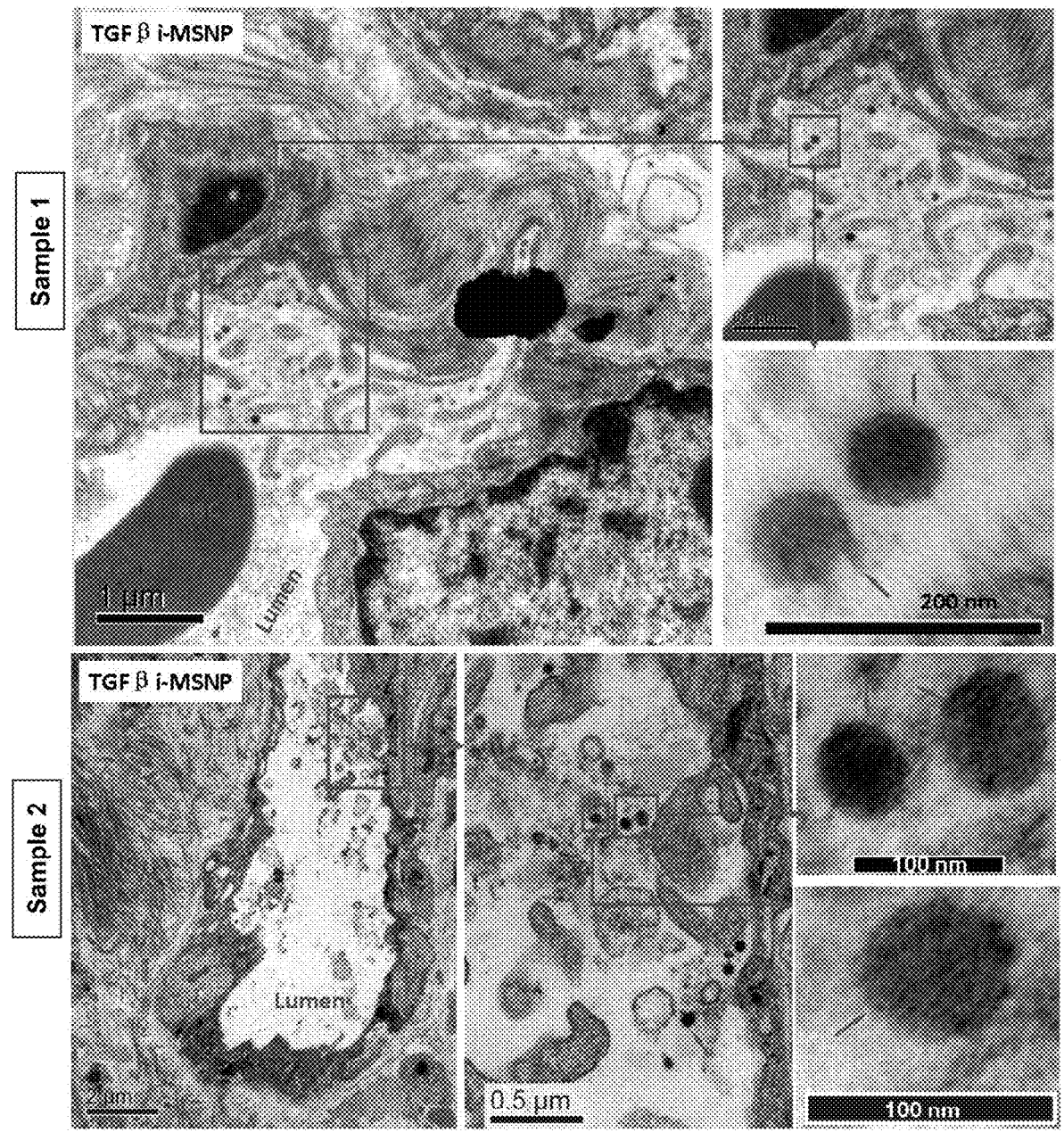
FIG. 9 shows an electron microscopic image of a BxPC3 tumor section from an animal injected i.v. with TGFβi-MSNP. The images taken at different resolutions show that the drug carrier (arrows) could be observed as intact, monodisperse particles in the tumor blood vessel. High-resolution TEM images could resolve the porous structure of the MSNP. RBC: red blood cell. C: Collagen.

In order to determine whether TGFβi delivery to a PDAC tumor site will have the same effect on PC co-localization with ECs in the tumor, we established BxPC3 xenografts in nude mice, because it has previously been shown that this human PDAC model gives rise to an aberrant and dense infiltrative stroma in which tumor blood vessels are embedded.[36] The presence of a dense stroma was confirmed by Masson's trichrome staining, which shows heavy collagen deposition in the BxPC3 xenograft (FIG. 3A). To achieve effective TGFβi delivery by our MSNP carrier we relied on its effective biodistribution properties and a relatively long circulatory half-life as a result of limited RES uptake due to the PEG coating.[37] TGFβi-MSNP was injected intravenously at inhibitor dose of 1 mg/kg (equivalent to a MSNP dose of 2 mg/kg) in nude mice expressing tumors ranging from 0.8~1.0 cm in diameter. Tail vein injections of saline or the free inhibitor (at same dose) were used as controls. To demonstrate the impact on PC/EC co-localization, dual-color immunohistochemistry was used for detecting CD31 staining in ECs with a green fluorescent dye (FITC), and NG2 in PCs with a red fluorescence marker (Alexa fluor 594) (FIG. 3).[7, 33] These results showed that TGFβi-MSNP injection could significantly disrupt the composite (yellow) fluorescence staining resulting from PC overlap with ECs (FIG. 3B). Little separation of the green and red fluorescence distribution was seen in saline treated animals, while injection of the free inhibitor resulted in a slight but non-significant reduction of the composite fluorescence staining (FIG. 3B). The likelihood that TGFβi was being delivered to the tumor vascular bed is suggested by the ultrastructural resolution of monodisperse mesoporous particles in small blood vessels, as recorded by electron microscopy (FIG. 4). More TEM images are shown below. In FIG. 9. Since the H-bonding of the drug to the polymer surface is pH sensitive, it is possible that acidification at the tumor site may contribute to the release of TGFβi.[38] This could also explain the absence of any other vascular abnormalities following TGFβi-MSNP injection in other organs where PCs reside (such as the brain, which will be described later).

Collectively, above data provide proof-of-principal testing of TGFβi bound MSNP as a potential nanocarrier that can be used to engineer PDAC stromal barrier for the ease of nano drug delivery.

Figure 5:
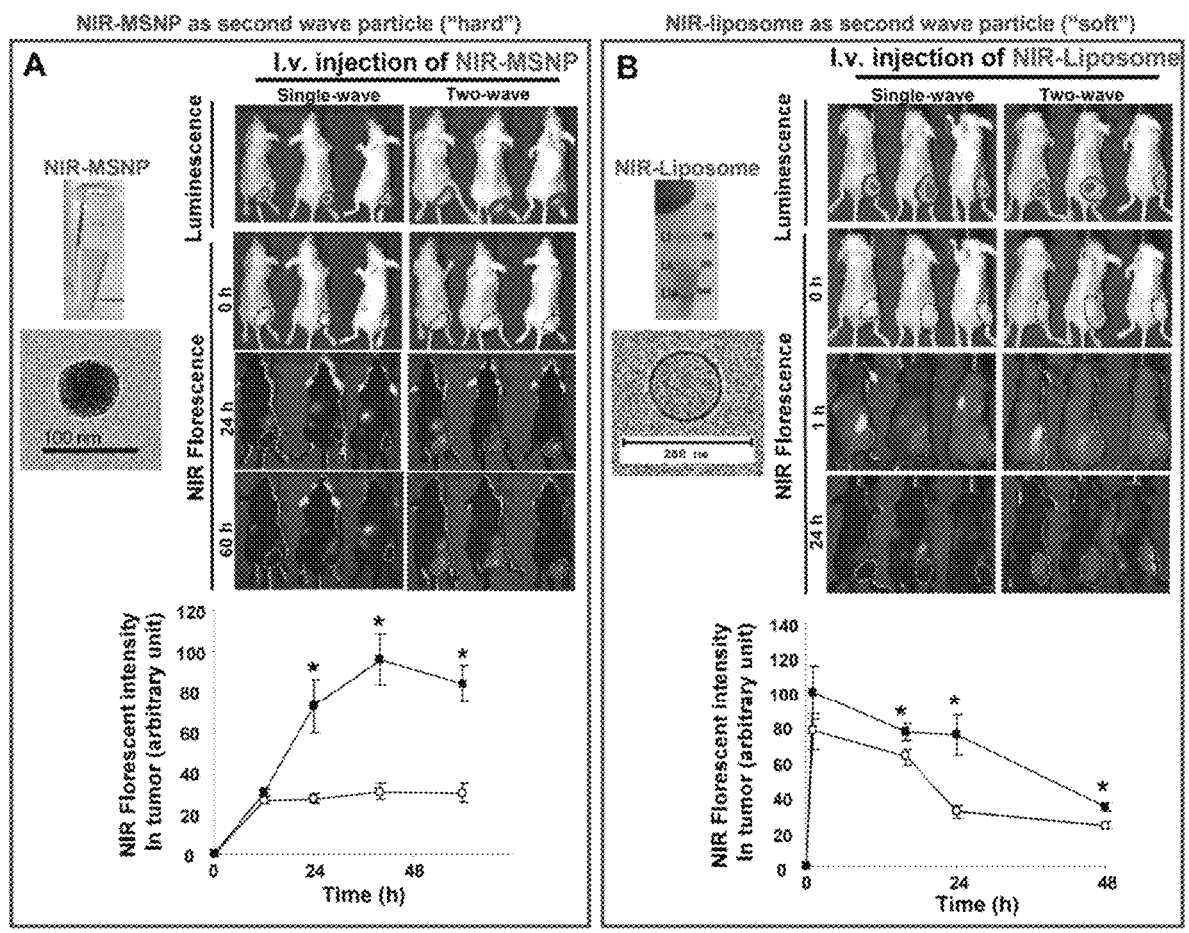
FIG. 5 shows TGFβi-loaded MSNP improves PDAC access of i.v. injected "hard" and "soft" nanoparticles in BxPC3 xenografts (A-B) An IVIS optical imaging system (Xenogen) was used to study the biodistribution of NIR dye labeled particles in the BxPC3 tumor-bearing mice. To visualize the luciferase expression in the cancer site, anesthetized mice received intraperitoneal injection of 75 mg/kg d-Luciferin, followed 8-10 min later by obtaining the bioluminescence images. Reference fluorescence images were captured before treatment. The tumor-bearing animals were first treated by i.v. injection of TGFβi-MSNP (inhibitor: 1 mg/kg) followed by i.v. injection of 50 mg/kg NIR-labeled PEI-PEG-MSNP or NIR-liposome with 1~2 h interval. The in vivo biodistribution was compared with the mice received i.v. injection of 50 mg/kg NIR dye labeled particles alone. Full panel of NIR images at different time points were shown, e.g.

TGFβi-Loaded MSNP Improves PDAC Access of i.v. Injected "Hard" and "Soft" Nanoparticles in BxPC3 Xenografts Since PCs regulate capillary blood flow as well as vascular access, the next question became whether TGFβi-MSNP could improve the egress of nanocarriers at the BxPC3 xenograft site.[39] We tested this possibility through the use of "hard" (100 nm PEI-PEG coated MSNP) and "soft" (130 nm liposome) nanocarriers in an imaginable biodistribution experiment in nude mice. These $2^{nd}$ wave particles were designed with near-infrared (NIR) tags to provide high photon penetration in animal tissues, as described previously by us.[28, 31] TEM or cryoEM images of the particles are provided in FIGS. 5A and 5B. Detailed characterization is provided in FIG. 11. To visualize the tumor growth in mice, BxPC-3 cells were stably transfected with a luciferase vector and used for obtaining bioluminescence images in the mice following intraperitoneal (i.p.) injection of d-Luciferin (FIGS. 5A and 5B, first row). Initial reference images showed very low NIR background in the tumor-bearing animals (FIGS. 5A and 5B, second row). Subsequently, the tumor-bearing animals were i.v. injected with TGFβi-MSNP (containing 1 mg/kg of the inhibitor), followed after 1~2 h interval, by i.v. injection of 50 mg/kg NIR-labeled MSNPs or liposomes. This biodistribution was compared to mice receiving i.v. injection of 50 mg/kg NIR-labeled particles in the absence of prior treatment with TGFβi-MSNP. NIR fluorescence images were captured at different time points as shown in the $3^{rd}$ and $4^{th}$ rows in FIGS. 5A and 5B. The full panel of NIR images appears in FIG. 11. In the absence of prior TGFβi-MSNP treatment, the images indicate that the labeled MSNPs were rapidly taken up in the spleen and kidney within 24 h (FIG. 5A, first column). While PEI-PEG coated MSNP has been sequentially optimized for systematic administration and passive retention in cervical and breast cancer xenografts[28, 31], there was limited egress in stroma-rich BxPC3 xenografts in nude mice (FIG. 5A, first column). While we still observed particle retention in the RES of mice injected with TGFβi-

Figure 12:
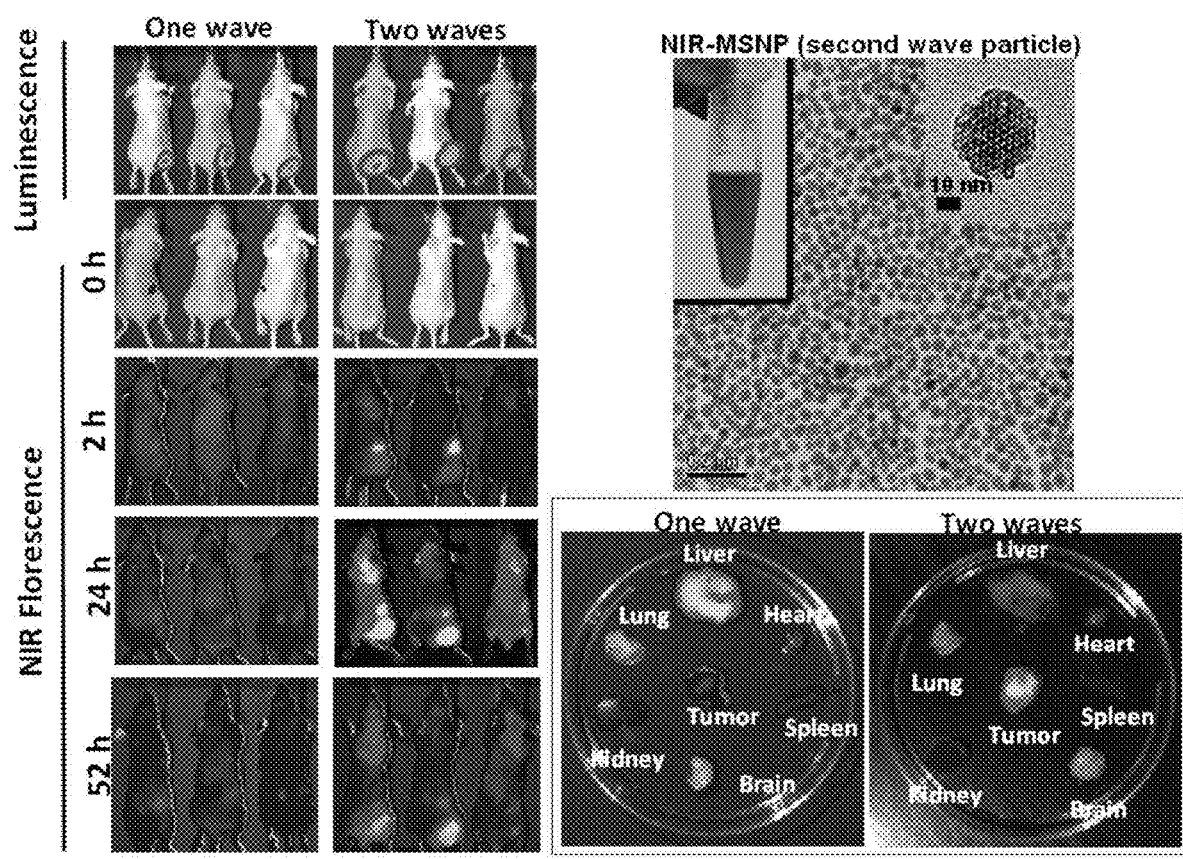
FIG. 12 shows the biodistribution of i.v. injected NIR dye-labeled 50 nm amine-modified and PEGylated MSNP to the BxPC3-luc tumor xenograft model in nude mice with or without TGFβi-MSNP.

MSNP, these animals showed prominent particle retention at the xenograft sites by 24 h, suggesting a strong particle retention effect (FIG. 5A, second column). Following the software analysis of the NIR fluorescence intensities at different time points as shown in the lower panel of FIGS. 5A, prior TGFβi-MSNP administration resulted in a significant increase in the fluorescence intensity by 40 h, whereupon the signal was sustained for at least 60 h. Very little change in fluorescence intensity was observed in the tumor tissue receiving NIR-MSNP alone. Similar enhanced retention of a 50 nm amine-modified, PEGylated MSNP at the xenograft site was observed following $1^{st}$ wave TGFβi-MSNP administration as shown in FIG. 12.

Figure 13:
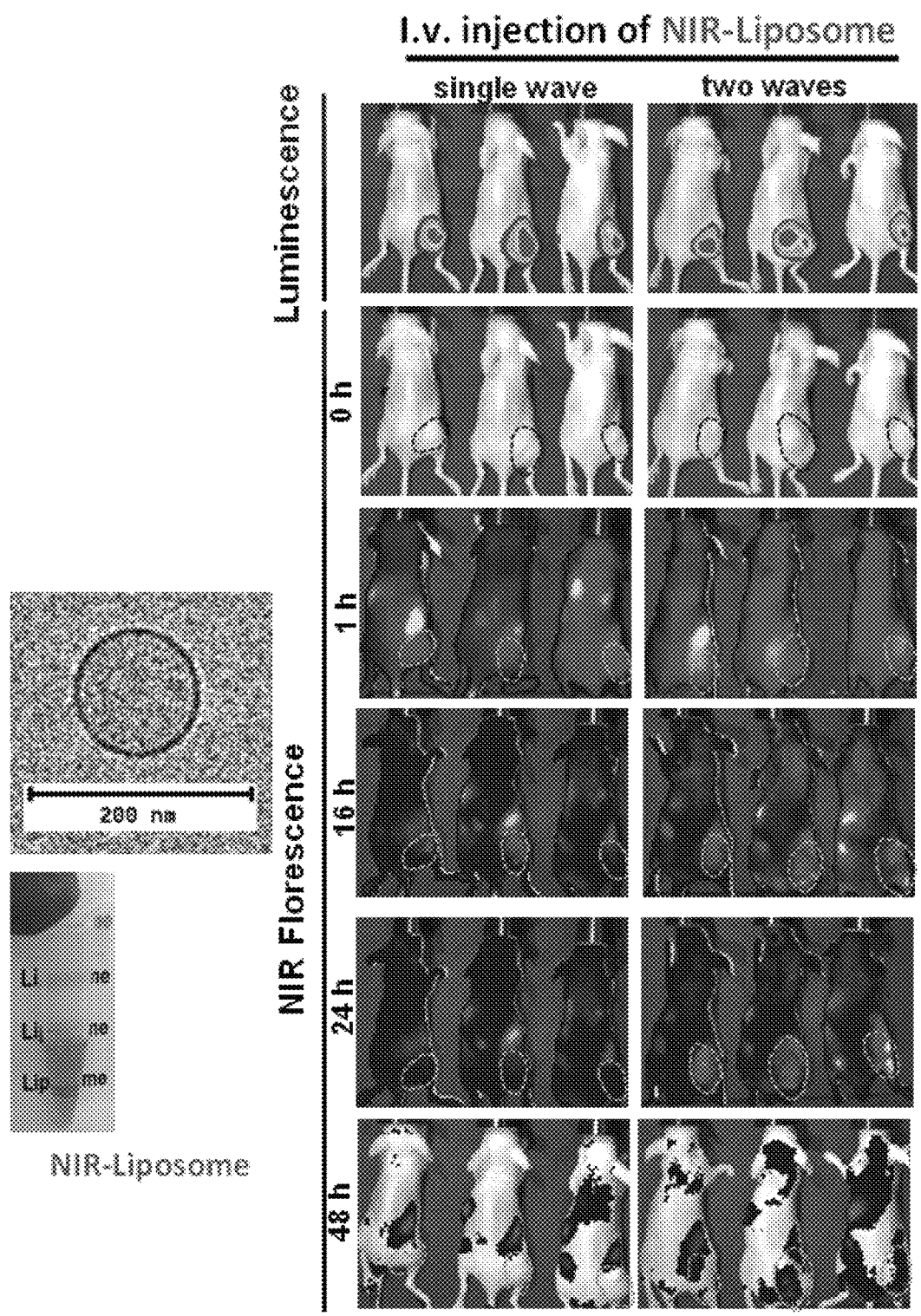
FIG. 13 shows a full panel of NIR images to show the biodistribution of 2nd wave NIR-liposomes at all time points for the experiment described FIG. 5B.

In parallel experiments, the effect of TGFβi-MSNP was also studied to visualize the retention of a liposomal particle (DPPC:Cholesterol:DSPE-PEG=7:2:1) at the BxPC3 xenograft site. To develop a NIR-labeled liposome, Dylight 680-DMPE (<0.1%, w/w) was incorporated into the lipid mixture. Compared to the biodistribution of the i.v. injected liposome alone (FIG. 5B, first column), there was a significant increase in fluorescence intensity at tumor site in the mice that were injected with TGFβi-MSNP (FIG. 5B, second column). Interestingly, the liposome accumulated with more rapid kinetics than the MSNP and could be observed in the xenograft 1 h post i.v. injection. The images also demonstrate that the liposomes disappeared faster than the silica nanoparticles, suggesting that the liposomes are rapidly metabolized in vivo (FIG. 5B and FIG. 13). Similar to MSNPs, semiquantitative imaging analysis showed that TGFβi-MSNP significantly increases liposome retention at the tumor site compared to injecting the liposomes alone (lower panel of FIG. 5B).

The mice receiving the NIR-labeled MSNPs were sacrificed at 60 h post injection, and ex vivo fluorescence images were obtained for the tumor tissue as well as major organs (FIG. 5C, upper panel). Consistent with the live animal imaging results, prior TGFβi-MSNP treatment was associated with increased fluorescence intensity in tumor tissue compared to animals receiving the $2^{nd}$ wave treatment alone. Both animal groups showed abundant particle distribution to the liver, spleen, lung, and the kidney. Following ex vivo imaging, the collected organs were weighed and used for Si elemental analysis by inductively coupled plasma optical emission spectrometry (ICP-OES). This allowed quantitative analysis of the particle distribution, expressed as a percentage (%) of the total mass of administered particles. While ~7% of the particles could be seen to biodistribute to the tumor tissue at 60 h in animals treated with TGFβi-MSNP, it is at least 10 times higher than the particle content of the BxPC3 tumor site in animals receiving the NIR-MSNP alone (FIG. 5C, lower panel). As a result of the shorter retention time of liposomes, we repeated the experiments in FIG. 5B with a new batch of animals in which the tumor tissue and organs were harvested at 24 h for ex vivo imaging. Consistent with the live imaging results, prior treatment with TGFβi-MSNP significantly increased fluorescence intensity at the tumor tissue compared to animals injected with liposomes alone. Both groups showed abundant distribution to liver, spleen, lung and kidney (FIG. 5D, upper panel). Calculation of fluorescence intensity using our established protocol,[31] prior treatment with TGFβi-MSNP resulted in the retention of ~7% of the administered liposomes as compared to ~1.8% of the injected dose in control tumors. This amount, as shown in the use of two-wave treatment approach, is approximately 4 folds higher than the animals injected with liposomes alone (FIG. 5D, lower panel).

Figure 6:
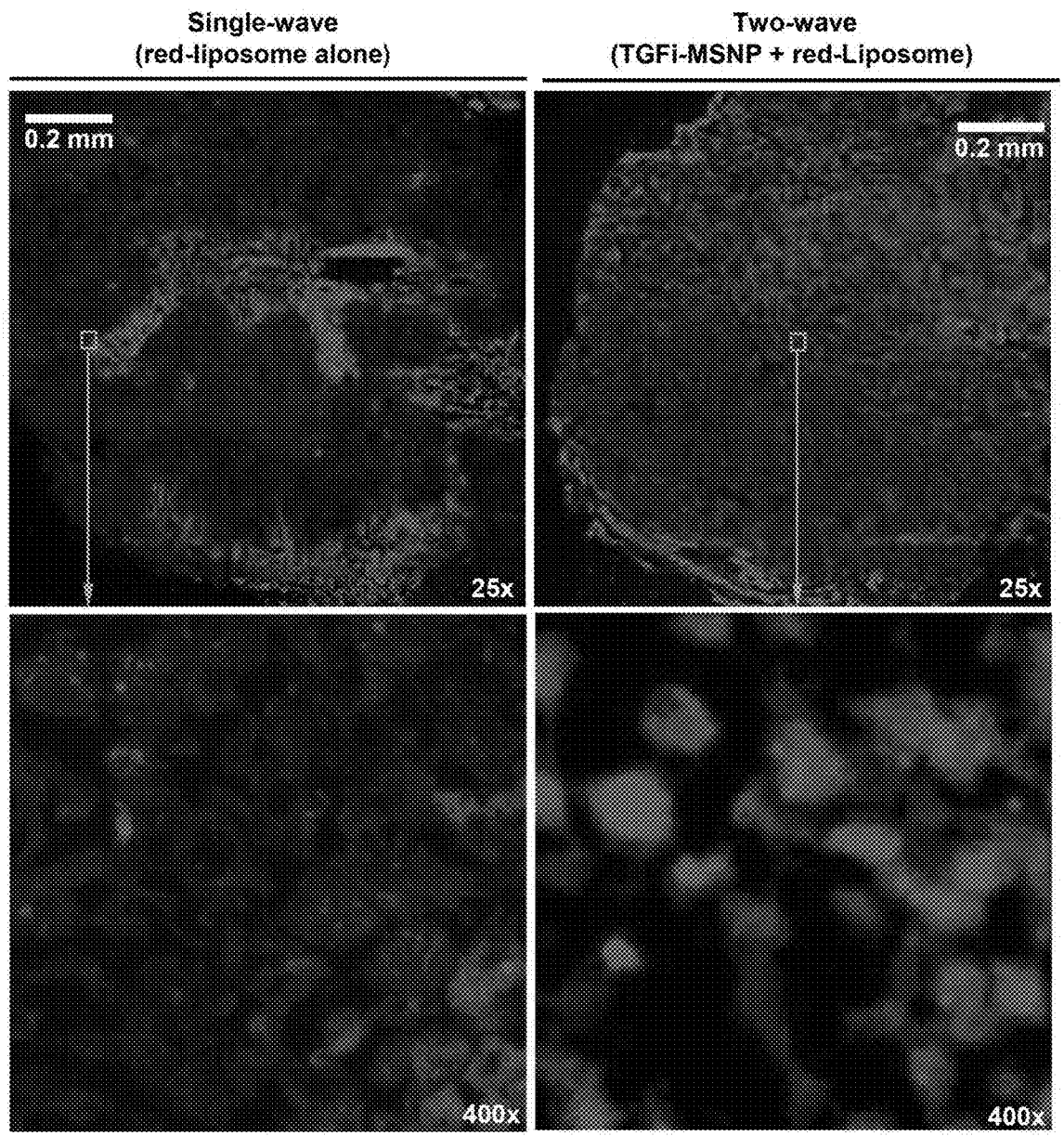
FIG. 6 shows fluorescent images of tumor tissue sections to show TGFβi-MSNP improve the extent of liposome intratumoral distribution in BxPC3 xenografts. (A) In order to determine whether two-wave therapy alters the intratumoral biodistribution of i.v. injected texas red labeled liposomes, these were i.v. injected into BxPC3 tumor-bearing mice in the absence or presence of prior TGFβi-MSNP injection. BxPC3 tumor-bearing mice received intravenous administration of TGFβi-MSNP (inhibitor dose: 1 mg/kg; MSNP dose: 2 mg/kg) followed by red labeled liposome with 1-2 h interval. Tumor tissues were collected 5 h post injection of the 2nd wave red labeled liposome. Frozen histological sectioning of the OCT embedded tumor tissues in each group was performed by the UCLA Division of Laboratory Animal Medicine (DLAM) diagnostic laboratory services. Slides were visualized under a fluorescence microscope (Zeiss, Germany). (B) Tumor tissue sections to show the tumor localization of the liposome in relation to the ECs and PCs detected by CD31 and NG2 biomarkers using immunofluorescent staining. Part of tumor sections in each group were incubated with a CD31 primary antibody and visualized by FITC-conjugated secondary antibody. The same section was further incubated with a NG2 primary antibody and visualized by pacific blue-conjugated secondary antibody. The red fluorescence of labeled liposome was also captured for the same slide view, and merged images were prepared to show intratumoral distribution of the liposome in relation to the blood vessels and their PCs coverage. High magnification images, labeled as "i"-"iii" in tumor received liposome alone and "iv"-"vi" in tumor received two-wave treatment, were provided.

TGFβi-MSNP Improve the Extent of Liposome Intratumoral Distribution in BxPC3 Xenografts In order to determine whether two-wave therapy alters the intratumoral biodistribution of texas red labeled liposomes, these were i.v. injected into BxPC3 tumor-bearing mice in the absence or presence of prior TGFβi-MSNP injection. Visual inspection of the fluorescence distribution under low magnification demonstrated a heterogeneous intratumoral distribution if the liposomes were injected alone (FIG. 6A, left upper panel). Most of the fluorescence intensity localized in the tumor perimeter. High magnification imaging further demonstrated that the labeled liposomes could be visualized as fluorescent intracellular dots that appear in the cytosol and perinuclear regions (FIG. 6A, left lower panel). This is in keeping with the cellular internalization of liposomes, some of which could be taken up in acidifying endosomal compartments in the tumor cells.[10] In contrast, there was a dramatic change in the intratumoral distribution of the liposomes following the $1^{st}$ wave delivery of TGFβi-MSNP (FIG. 6A, right upper panel). Additional immunohistochemical staining for CD31 with a FITC-conjugated antibody and NG2 with a pacific blue-conjugated antibody allowed us to determine liposomal localization in relation to ECs and PCs, respectively (FIG. 6B). As compared to single wave delivery of liposomes alone, two-wave treatment resulted in more abundant and homogenous liposome distribution in the xenograft tissue. Moreover, merging of blue and green fluorescent images demonstrated the disassociation in ECs and PCs during two-wave treatment (FIG. 6B, regions "vi", "v", and "vi") as compared to the co-localization of these cells (FIG. 6B, regions "i", "ii", and "iii") in animals injected with liposomes only. All considered, these data demonstrate that TGFβi-MSNP pre-treatment allows vascular access and widespread intratumoral distribution of engineered nanoparticles. This prompted the question of whether two-wave therapy can be used to improve the efficacy of GEM-laden liposomes in PDAC tumor-bearing mice.

Two-Wave Treatment Improves the Efficacy of Gemcitabine Treatment of BxPC3 Tumors To demonstrate the possible effect of TGFβi-MSNP for treatment efficacy of BxPC3 xenografts, we decided to use the same liposomal carrier depicted in FIG. 5B for encapsulate the delivery of GEM. In order to improve its loading capacity, we created an $(NH_4)_2SO_4$ salt gradient in the liposome,[40] which through protonation of the drug could increase GEM transport from the incubation medium as a function of ammonium sulfate concentration, extent of salt removal, the effect of temperature, drug loading time, and amount of free GEM, etc (FIG. 10).[11, 40-42] This allowed us to achieve GEM loading capacity of 19.8% w/w, which stands in contrast to a conventional loading in which showed a loading capacity of 10.3% w/w. Full details about the liposome design, detailed physicochemical characterization, optimization of drug loading, stability, cellular uptake, and ability to protect the drug against CDA inactivation are described in FIG. 10.

Figure 7:
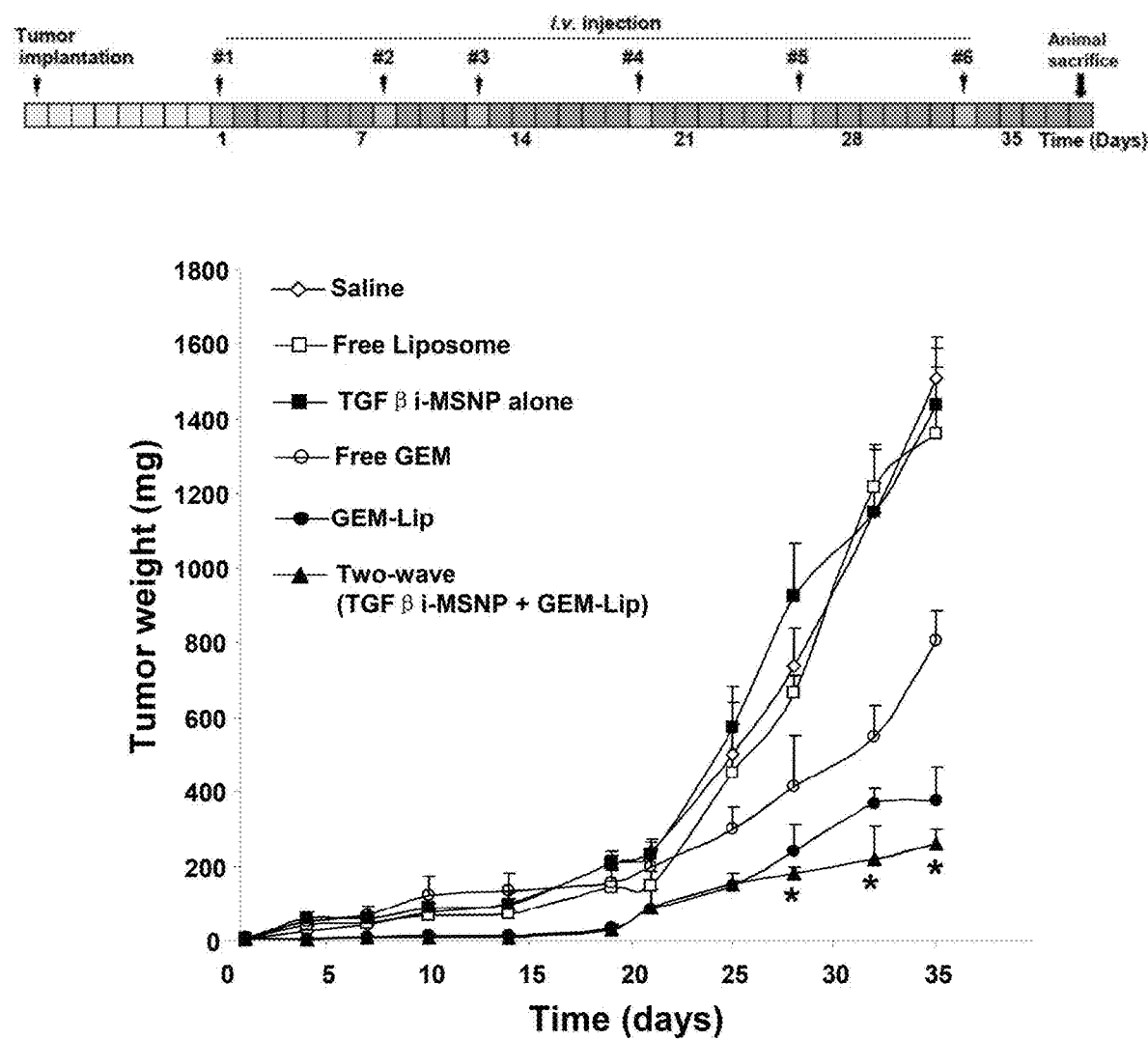
FIG. 7 shows tumor growth inhibition and assessment of treatments on animal weight and kidney histology in BxPC3-bearing nude mice. (A) The animal treatments are described in the method section. BxPC3 cells were subcutaneously injected into mice 7 days before treatments (gray boxes). These animals received six i.v. injections (red boxes) every 3-6 days (green boxes) for 38 days as shown. The tumor inhibition effect of two-wave treatment was compared to saline, GEM-Lip alone, free GEM, empty liposome, and TGFβi-MSNP. Tumor size was accurately measured 1-2 times per week. Tumor weight was calculated according to the formula Tumor weight (mg)=(length in mm)×(width in mm)2/2. *$P<0.05$, compared to GEM-Lip group. (B) The animal weights were recorded at indicate time points and expressed for the experimental duration. *$P<0.05$, compared to saline; #$P<0.05$, compared to GEM-Lip. (C) Histological analyses of kidney sections were performed by UCLA DLAM diagnostic laboratory services. The sections were stained with hematoxylin/eosin (H&E) and examined by light microscopy. Representative images are shown. Higher magnification images were provided to shown the swelling and edema occur in Bowman's space, a morphological abnormality of GEM-induced renal toxicity. White arrows point to normal Bowman's space in glomerulus, and the black arrows point to the swelling and edema occur in Bowman's space.

In the animal efficacy experiment, xenograft-bearing nude mice were i.v. injected with 101 mg/kg of the liposomes (GEM dose: 20 mg/kg) 1-2 h after the i.v. injection of TGFβi-MSNP (TGFβi dose of 1 mg/kg), every 3-6 days for 38 days (FIG. 7A). The controls included animals injected with saline, free GEM, empty liposomes, TGFβi-MSNP alone, and GEM-liposomes alone. Since our previous studies have shown that empty MSNP lacks anticancer activity,[28, 31] we did not include this as a negative control in our animal experiments. When comparing the effect on tumor size, the GEM liposome showed a significantly higher rate of tumor shrinkage than the free drug (FIG. 7A). The use of two-wave treatment beyond 25 days, demonstrated an additional and significantly higher rate of tumor inhibition compared to the use of the GEM-liposome alone. This delay in observing the effect of prior TGFβi-MSNP treatment could be due to the effect of tumor stage, with the stromal effects and vascular access becoming a problem beyond 25 days. No tumor inhibition was found with saline treatment, TGFβi-MSNP alone or the use of empty liposomes (FIG. 7A).

Two-Wave Therapy Reduces the Systemic Toxicity of GEM

The safety of nanocarrier delivery system is of key importance in the assessment of this therapeutic platform. This includes the inherent safety of the carrier as well as the possible benefits that may accrue due to drug encapsulation. Safety assessment was performed by monitoring total body weight, blood chemistry, and histological examination of major organs. Compared to saline-treated BxPC3 tumor-bearing mice, no significant body weight changes were observed during the administration of empty liposomes, GEM-liposomes, or TGFβi-MSNP plus GEM-liposomes. In contrast, animals receiving free GEM administration showed a reduced weight gain (FIG. 7B). While none of the animals showed a significant elevation of biomarkers that denote major organ dysfunction, free GEM resulted in intermediate nephrotoxicity,[43] which manifested as glomerular swelling and edema of Bowman's space in the kidney glomerulus. However, this histological change did not occur in other groups and histological examination of the liver and spleen did not show any gross pathology in any of the experimental groups.

Discussion

In this study, we used an engineered approach wherein TGFβi-MSNP treatment was used to initially target the tumor stroma to decrease PC coverage of EC, followed by the delivery of GEM-laden liposomes that were effectively distributed throughout the tumor tissue, resulting in enhanced killing of the cancer cells after a window of 25 days following treatment. In order to achieve optimal in vivo efficacy, both particle waves were optimally designed to prolong circulation time in the blood, reduce RES uptake, and carry an effective drug payload to the cancer site. Thus, the co-polymer coated MSNP could deliver a high load of a TGFβi, which was supramolecularly attached to PEI, and through slow release could interfere in PCs adherence to the tumor vasculature at the xenograft site. This allowed nanocarrier egress through the vascular fenestrations, with the ability to enhance encapsulated GEM delivery to the tumor site. The $2^{nd}$ wave of delivery was achieved by an optimally designed liposome characterized by PEG surface display as well as the ability to import and retain the protonated GEM at a ~20% w/w loading capacity. Release of the encapsulated GEM throughout the xenograft tumor was associated with increased cancer cells and less renal toxicity compared to the free drug. All considered, these data demonstrate that two-wave nanotherapeutics can be used to target the effect of the stroma in PDAC drug delivery, while also providing protected delivery of GEM to the tumor site. This allows further testing of this platform in orthotopic human pancreatic cancer models in immunocompromised animals as well as consideration for phase I human trials based on the two-wave treatment concept.

Figure 8:
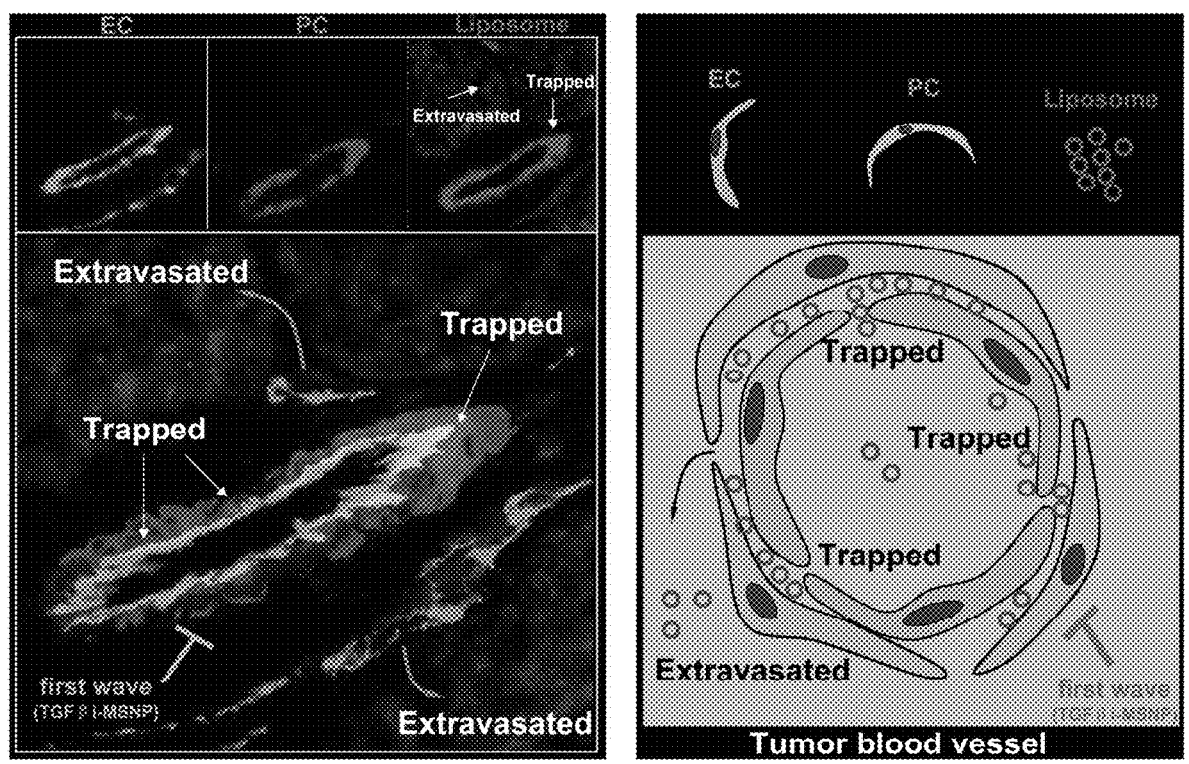
FIG. 8 shows the display of a dysplastic stroma that includes PC coverage of vascular fenestrations is an important consideration to improve the tumor access of drug laden nanoparticle. Use of tumor tissue histology to show that the PDAC tumor elicits a dense stromal barrier, which includes effective PC coverage of tumor blood vessel fenestrations, to the extent that blocks vascular access of i.v. injected red labeled liposome at BxPC3 tumor site. PCs were labeled in blue using a NG2 marker. ECs were labeled in green using a CD31 marker. One can see that liposome successfully extravagated from tumor fenestration in absence of PCs, however, many liposomes were trapped in tumor blood vessel in which the ECs were efficiently covered by PCs. The PC barrier can be visually shown by the sandwich-like blue-red-green arrangement (that indicates PCs-liposomes-ECs) in the tumor fenestration. To improve liposome access at tumor fenestration, we have designed a two-wave treatment strategy with the intention of removing the this effective PC coverage during the 1st wave therapy using TGFβi loaded MSNP, followed by a 2rd wave therapy in which a high dose of cancer drug GEM is delivered by liposome. A scheme, on the right hand side, was provided to conceptualize this two-wave approach for PDAC treatment.

Utilizing our multifunctional MSNP platform to conduct proof-of-principle studies in various human cancer models, we have observed a wide range of challenges imposed by micro-heterogeneity in the tumor environment that goes beyond the concept of an enhanced permeability and retention effect. While undoubtedly vascular abnormalities such as large fenestrations could contribute to nanocarrier egress at the cancer site, there are a number of tumor-specific biological impediments to vascular access. In the case of PDAC, the display of a dysplastic stroma that includes PC coverage of vascular fenestrations is an important consideration (see FIG. 8). Thus, it is important to consider this impediment in the design of nanocarriers for drug delivery, including the consideration of an engineered approach towards specific barriers, which can be targeted by independent waves of therapy that ultimately provide effective of killing and elimination of the cancer tissue. However, while several creative ideas have emerged to attempt multistage nanotherapeutics[44,45] or combination therapy[7, 14, 46, 47] with the view to improve systemic drug delivery through increased blood vessel permeability, tumor penetration or reducing the effect of drug inactivation enzymes, most of the research efforts concentrated on cancer cell killing with few efforts being directed to the cancer microenvironment.[31] In fact, the tumor microenvironment is a very complex system that differs from the normal tissue environment and significantly influences the efficacy of nano delivery systems. This includes the contribution from a variety of components in the tumor microenvironment, i.e., biophysicochemical factors (hypoxia, acidosis, high interstitial fluid pressure), heterogeneous cellular components other than cancer cells (endothelial cells and pericytes, cancer-associated fibroblasts, and inflammatory cells), and non-cellular components (extracellular matrix, matrix metalloproteinase, soluble growth factors and their receptors, and integrins).[31] Thus, one or more of these heterogeneous components could be the target(s) of an engineered approach. One example is the use of macrolide-modified gold nanorods that were designed to target and activate antitumor potential of macrophages.[48] This research demonstrated that the nanorods preferentially accumulate in tumor-associated macrophages, leading to a significantly enhanced killing potential of breast cancer cells.[48] The importance of manipulating the tumor microenvironment is further illustrated by our study in which the dense stromal barrier could be impacted by delivery of a small molecule inhibitor, thereby enhancing encapsulated drug delivery by a $2^{nd}$ wave nanocarrier. While we have demonstrated similar, but lesser stromal effects in a drug resistant human breast cancer xenograft, the accompanying microvascular heterogeneity was still responsible for preventing total disappearance of the tumor.[31] For PDAC, this problem is much more accentuated, thereby differentiating this from cancer types with a less prominent stroma, therefore allowing a prominent EPR effect.[7, 49]

The idea of targeting the PDAC stroma in clinical studies has been addressed by using of PEGylated hyaluronidase PH20 (PEGPH20), which targets hyaluronan, a tumor matrix component, which is responsible for a high interstitial fluid pressure (IFP) that interfere in penetration.[50] Results from an ongoing clinical trial has demonstrated that the combination of GEM with PEGPH20 treatment can improve the stromal barrier, allowing chemotherapeutic agents drugs to freely permeate the cancer site.[51, 52] This differs from our animal study in which we did not observe a significant change in the collagen content, probably due to the relatively short duration of treatment. In a recent phase III clinical trial in previously untreated PDAC patients with metastatic disease, it has been demonstrated that the combination of Abraxane® (paclitaxel/albumin complex) with GEM could induce a statistically significant improvement in overall survival compared to patients receiving drug alone (median of 8.5 vs. 6.7 months).[53] In the animal study, it was demonstrated that paclitaxel is capable of defeating the desmoplastic stroma, and increasing the GEM content 2.8-fold in the tumor as a result of the reducing CDA enzyme levels.[46, 54] Therefore, it will be interesting to test in future whether combined delivery of GEM and paclitaxel by a nanocarrier could be used as an even more effective 2nd wave of treatment.

The TGF-β superfamily plays an important role in cancer biology.[24] This includes a role in tumor neo-angiogenesis in which the interaction of PCs with ECs play a role in formation of intact blood vessels.[17] The effects of inhibiting the TGF-β signaling pathway has been demonstrated in multiple in vitro and in vivo models, i.e. tumor xenograft models, a retinal vascular model, and a 3D PC/EC co-culture model.[7, 18, 22, 55] Collectively, these studies indicate that TGF-β maintains the integrity and function of the microvasculature while interference in this pathway often leads to dissociation of EC from PC and impaired EC barrier function.[7, 18, 22, 55] Our results also confirm a previous study showing that low dose intraperitoneal injection of TGFβi promotes vascular access and accumulation of nanoparticles and macromolecules in BxPC3 subcutaneous xenograft model and OCUM-2MLN orthotopic gastric cancer model.[7, 18] In addition, TGF-β negatively regulates local tumor immune responses and one can envisage that TGFβi-MSNP may promote the function of tumor antigen specific CD8$^+$ T cells in the local immunosuppressive tumor microenvironment.[56,576]

Finally, we want to address the loading capacity of drugs in the nanocarrier. Good drug loading is important for efficacious cancer cell killing as well as the potential to decrease systemic toxicity by lowering the amount of the nanomaterial that needs to be injected. We were able to optimize the effects of the LY364947 delivering particle by using supramolecular attachment of its electronegative nitrogen residues to the hydrogen atoms in PEI, with the ability to achieve a 74% (w/w) loading capacity. Not only have we been able to achieve a nanocarrier that can be used for cancer applications, as demonstrated in this communication, but also for the treatment of tissue inflammation, pulmonary fibrosis and arthritis. In the case of a liposomal carrier, a high loading capacity (~20%) for GEM was achieved by creating an ammonium sulfate gradient in the liposome. This allowed intra-liposomal retention of the drug, which is protonated after diffusion through the liposomal membrane.[40] It has also been shown that the encapsulated GEM is stabilized as a gel-like precipitate inside the liposome (FIG. 10).[40]

In conclusion, by addressing a specific aspect of the biology of PDAC, we could develop an engineered approach in a human xenograft model wherein we could improve vascular access past the stromal barrier as well as delivery of chemotherapeutic agent. We propose that this approach is much more rational than the conventional passive and active delivery approach of chemotherapeutic agents by nanocarriers. However, we do not exclude the possibility that the addition of targeting ligands to our nanocarriers could further enhance their efficacy.

Studies are carried out with the submicron structures described in Example II (drug(s)-laden lipid bilayer coated MSNP), using the same procedures described in this Example I. For example, near infrared labeled particles are synthesized for in vivo biodistribution studies in tumor xenograft bearing nude mice, and in vivo efficacy tests are carried out. It is expected that the in vivo efficacy can be at least as effective as for the subunit structures described in present Example I.

Materials and Methods

Materials and Experimental Details

The materials and experimental methods are described in detail elsewhere herein.

Synthesis of PEI-PEG Coated Mesoporous Silica Nanoparticles and NIR Labeling

The synthesis of the 50 nm MSNP core was carried out as previously described by us, using a sol-gel chemistry procedure.[28] The particle surface was further modified using electrostatic attachment of a 1.8 kD PEI polymer, which was subsequently used for covalent attachment of 5 kD PEG. To perform PEI coating, 10 mg of MSNP was suspended in 1 mL of 2.5 mg/mL PEI 1.8 kD ethanolic solution. The solution was sonicated and stirred for 30 min. The particles were further washed in ethanol to remove excess PEI and trace amount of surfactant. The PEI-coated particle was subsequently transferred into 1.5 mL of DMF, mixed with 50 mg of activated poly(ethylene glycol) methyl ether (m-PEG, MW 5 kD), and stirred for 24 h. The nanoparticles were washed with DMF and ethanol and resuspended in water.[28, 31] The NIR fluorescent dye DyLight 680 NHS ester was used for particle labeling. 10 mg particles were suspended in 1 mL of DMF and mixed with 0.1 mg of Dylight 680. The reaction took place under an inert atmosphere during stirring at room temperature for 12 h. The particles were centrifuged and washed with deionized water.[28]

Assessment of TGFβi Loading Capacity and Binding Stability

Various volumes (10 µL, 20 µL, 40 µL, 80 L) of 5 mg/mL LY364947 DMSO solutions were suspended in 1 mL of 0.5 mg/mL MSNP aqueous suspension. The mixture solutions were stirred at 25° C. for 24 h, and washed 3 times with deionized water. After centrifugation at 15,000 rpm for 30 min, the supernatants were collected to obtain OD value of LY364947 at 269 nm (Me, Molecular Devices, USA). The loading capacity was calculated as follows: Loading capacity (%, w/w)=[(Total minus non-encapsulated weight of LY364947)/(weight of MSNPs)]×100%. In order to determine the stability of LY364947 attachment, the drug release was studied in deionized water, saline containing 2% fetal calf serum or DMEM supplemented with 10% FCS for time periods ranging from 0-72 h at 37° C. Following samples centrifugation at 15,000 rpm for 30 min, the release percentage was calculated according to the following equation: Release percentage (%)=[(the weight of LY364947 in the supernatants)/(the total weight of attached LY364947 at the starting point)]×100%.

Cell Lines and Cell Culture

Human microvascular endothelial cell (HDME, used as ECs model) was purchased from ScienCell Research Laboratories (Carlsbad, CA). The ECs were cultured in endothelial cell medium (ECM, Carlsbad, CA) containing 5% FBS, 1% endothelial cell growth supplement (ScienCell, Carlsbad, CA), 100 U/mL penicillin, 100 µg/mL streptomycin. Human smooth muscle (HSM, a pericyte-like cell type and used as PCs model[33]) was purchased from American Type Culture Collection (ATCC). The PCs were cultured in ATCC-formulated F-12K medium containing 0.05 mg/mL ascorbic acid, 0.01 mg/mL insulin, 0.01 mg/mL transferring, 10 ng/mL sodium selenite, 0.03 mg/mL endothelial cell growth supplement, 10 mM 4-(2-hydroxyethyl)-1-piperazineethanesulfonic acid (HEPES), 10 mM 2-[(2-Hydroxy-1,1-bis(hydroxymethyl)ethyl)amino]ethanesulfonic acid (TES), and 10% FBS. BxPC-3 cells were purchased from ATCC and cultured in Dulbecco's modified eagle medium (DMEM) (Carlsbad, CA) containing 10% FBS, 100 U/mL penicillin, 100 µg/mL streptomycin, and 2 mM L-glutamine.

Matrigel Assay

To study the effect of TGFβi-MSNP on PC/EC interaction, the Matrigel assay was performed using a modified method in the literature.[33] In order to distinguish the PCs and ECs in the Matrigel assay, HDME cells ($10^4$ cells/mL) and HSM cells ($5 \times 10^3$ cells/mL) were first stained by CellTracker™ Green CMFDA (Invitrogen, Grand Island, NY) and CellTracker™ Red CMTPX (Invitrogen, Grand Island, NY) according to the manufacture's instruction 24 h before experiment. After live cell staining, ECs were treated with 2 ng/mL of TGF-β for 3 h and PCs were treated with free TGF-β or TGFβi-MSNP at inhibitor dose of 1 µM for 3 h. Subsequently, both cell types were co-cultured in Matrigel-coated 6-well plates for further incubation of 16 h at 37° C. PC/EC adhesions were quantitatively determined from five fields of three independent samples with the fluorescent microscope (Zeiss, Germany).

Smad2 Activation Assay

Smad2 activation was determined using an immunofluorescent staining in 8-well chamber slides in which $4 \times 10^4$ PCs were cultured in each well containing 0.4 mL culture medium. 16 h post cell seeding, PCs were treated with 2 ng/mL TGF-β for 3 h. Subsequently, the cells were treated with TGFβi-laden MSNP at the inhibitor dose of 1 M for 1-24 h. For comparison, free TGFβi was used to treat the cells at identical dose. Subsequently, PCs cells grown on chamber slides were fixed, permeabilized, and stained for pSmad2 with a standard immunocytochemistry protocol. pSmad2 staining was performed by using a 1:500 dilution of primary anti-pSmad2 antibody (Abcam, Cambridge, MA) for 16 h at 4° C. This was followed by a 1:500 diluted FITC-conjugated secondary antibody (Santa Cruz, USA) for 1 h at room temperature. The nuclei were stained with Hoechst 33342. Slides were visualized under a confocal microscope (Leica Confocal 1P/FCS). The signal intensity of green channel, revealing activated Smad2, was calculated by Image J software (version 1.37c, NIH).

Establishment of BxPC3 Tumor Xenograft Model

Athymic BALB/c nu/nu female mice (6 weeks) were purchased from the Charles River Laboratory and maintained under pathogen-free conditions. All animal experiments were performed using protocols approved by the UCLA Animal Research Committee. For tumor visualization in mice using optical imaging, permanent luciferase transfection using lentivirus was performed in BxPC3 cells. To grow tumor xenograft, BxPC3-luc cell suspension (0.1 mL, $5 \times 10^6$ cells/mL) was injected subcutaneously into nude mice. For efficacy experiment, the mice were used for various treatments 7 days post tumor implantation. To perform imaging experiment, the tumor bearing animals were used 3-4 weeks after tumor implantation of the tumor size of 0.8-1 cm in diameter.

Bio-Distribution

In order to determine the effect of the $1^{st}$ wave particle on improving the distribution of systemically administrated $2^{rd}$ nanoparticle in BxPC3 tumor, the imaging studies were performed. To visualize the tumor growth, BxPC3-luc were used for obtaining bioluminescence images in the mice following intraperitoneal (i.p.) injection of D-Luciferin at 75 mg/kg. Eight to ten minutes after injection, bioluminescence images were acquired using an IIS Imaging System (Xenogen, Toronto, ON, Canada). The mice were first intravenously administrated with TGFβi-laden MSNP at an inhibitor dose of 1 mg/kg, which is equivalent to a MSNP dose of 2 mg/kg. To visualize the $2^{rd}$ wave particle in vivo, the NIR-MSNP or NIR-liposome were used. One to two hour after TGFβi-laden MSNP injection, the mice were intravenously administrated with 50 mg/kg of NIR dye-labeled particles. The fluorescence images were taken at indicated time points. This treatment was compared to the mice received i.v. injection of NIR dye-labeled MSNP or liposome alone at 50 mg/kg. The tumor tissue together with major organs (heart, lung, spleen, liver, kidney, brain and cardiac muscle) were collected and used for ex vivo image.

Transmission Electron Microscopy of BxPC3 Tumor Received TGFβi-Laden MSNP Treatment BxPC3 tumor-bearing mice (tumor size: 0.8-1 cm in diameter) were intravenously treated with TGFβi-laden MSNP at inhibitor dose of 1 mg/kg (MSNP dose: 2 mg/kg). The tumor biopsies were rapidly collected 2 h post injection, washed in PBS and immediately fixed with 2.5% glutaraldehyde in PBS at room temperature for 2 h and stored at 4° C. for overnight. Further sample preparation and sectioning were performed by Electron Microscopy Services Center in Brain Research Institute at UCLA. Briefly, after secondary fixation in 1% $OsO_4$ in PBS, the samples were dehydrated in a graded ethanol series, treated with propylene oxide, and embedded in resin. Approximately 60-70 nm thick sections were cut on a Leica ultramicrotome and picked up on Formvar-coated copper grids. The sections were examined in a CM120 electron microscope (Philips).

Co-Staining of the Markers of ECs and PCs in Tumor Section

The tumor tissues were rapidly embedded by OCT reagent before sectioning to provide 4 m thick slices. The slices were washed three times in PBS and fixed. For ECs staining, the sections were first incubated with rat-anti-mouse CD31 monoclonal antibody (1:500) at 4° C. overnight. After removal of the primary antibody and washing in PBS for three times, FITC-conjugated goat-anti-rat IgG (1:500) was added and incubated at room temperature for 1 h. For PCs staining, the same section was further incubated with primary antibody of NG2 (1:500) at 4° C. overnight and followed by Alexa594- or pacific blue-conjugated secondary antibody (1:1000) at room temperature for 1 h. All the incubations were performed in dark. The slides were visualized under a fluorescence microscope. The PC coverage was counted from three randomly selected fields.

Nude Mouse Studies to Determine the Efficacy of Two-Wave Treatment on Tumor Shrinkage One week after tumor implantation, the BxPC-3 tumor-bearing mice were randomly divided into six groups. These groups were used for comparing the effects of saline, free liposome, TGFβi-MSNP alone, free GEM, GEM-Lip alone, and two-wave treatment, respectively. Each animal in two-wave group received i.v. injection of TGFβi-MSNP at inhibitor dose of 1 mg/kg (MSNP dose: 2 mg/kg) followed by a liposome dose of 101 mg/kg (GEM dose: 20 mg/kg) with 1-2 h interval, during each injection, 6 injections in a 38 days time period (FIG. 6A). The free GEM and GEM loaded liposome groups received the same drug dose in the absence of TGFβi-MSNP pre-treatment. The groups treated with saline, empty liposome, and TGFβi-MSNP, were used as control. The body weight and tumor size were accurately recorded one to two times per week. Tumor weight was calculated according to the formula Tumor weight (mg)=(length in mm)×(width in mm)$^2$/2.

REFERENCES FOR EXAMPLE IA

1. Hezel, A. F.; Kimmelman, A. C.; Stanger, B. Z.; Bardeesy, N.; DePinho, R. A., Genetics and biology of pancreatic ductal adenocarcinoma. *Genes & Development* 2006, 20, (10), 1218-1249.
2. Wray, C. J.; Ahmad, S. A.; Matthews, J. B.; Lowy, A. M., Surgery for Pancreatic Cancer: Recent Controversies and Current Practice. *Gastroenterology* 2005, 128, (6), 1626-1641.
3. Kleeff, J.; Reiser, C.; Hinz, U.; Bachmann, J.; Debus, J.; Jaeger, D.; Friess, H.; Buchler, M. W., Surgery for Recurrent Pancreatic Ductal Adenocarcinoma. *Annals of Surgery* 2007, 245, 566-572.
4. Erkan, M.; Hausmann, S.; Michalski, C. W.; Fingerle, A. A.; Dobritz, M.; Kleeff, J.; Friess, H., The role of stroma in pancreatic cancer: diagnostic and therapeutic implications. *Nat Rev Gastroenterol Hepatol* 2012, 9, (8), 454-467.
5. Morikawa, S.; Baluk, P.; Kaidoh, T.; Haskell, A.; Jain, R. K.; McDonald, D. M., Abnormalities in Pericytes on Blood Vessels and Endothelial Sprouts in Tumors. *The American journal of pathology* 2002, 160, (3), 985-1000.
6. Armulik, A.; Abramsson, A.; Betsholtz, C., Endothelial/Pericyte Interactions. *Circulation Research* 2005, 97, (6), 512-523.
7. Kano, M. R.; Bae, Y.; Iwata, C.; Morishita, Y.; Yashiro, M.; Oka, M.; Fujii, T.; Komuro, A.; Kiyono, K.; Kaminishi, M.; Hirakawa, K.; Ouchi, Y.; Nishiyama, N.; Kataoka, K.; Miyazono, K., Improvement of cancer-targeting therapy, using nanocarriers for intractable solid tumors by inhibition of TGF-β signaling. *Proceedings of the National Academy of Sciences* 2007, 104, (9), 3460-3465.
8. Zhang, L.; Nishihara, H.; Kano, M. R., Pericyte-Coverage of Human Tumor Vasculature and Nanoparticle Permeability. *Biological and Pharmaceutical Bulletin* 2012, 35, (5), 761-766.
9. Patra, C. R.; Bhattacharya, R.; Wang, E.; Katarya, A.; Lau, J. S.; Dutta, S.; Muders, M.; Wang, S.; Buhrow, S. A.; Safgren, S. L.; Yaszemski, M. J.; Reid, J. M.; Ames, M. M.; Mukherjee, P.; Mukhopadhyay, D., Targeted Delivery of Gemcitabine to Pancreatic Adenocarcinoma Using Cetuximab as a Targeting Agent. *Cancer Research* 2008, 68, (6), 1970-1978.
10. Straubinger, R. M.; Hong, K.; Friend, D. S.; Papahadjopoulos, D., Endocytosis of liposomes and intracellular fate of encapsulated molecules: Encounter with a low pH compartment after internalization in coated vesicles. *Cell* 1983, 32, (4), 1069-1079.
11. Celano, M.; Calvagno, M.; Bulotta, S.; Paolino, D.; Arturi, F.; Rotiroti, D.; Filetti, S.; Fresta, M.; Russo, D., Cytotoxic effects of Gemcitabine-loaded liposomes in human anaplastic thyroid carcinoma cells. *BMC Cancer* 2004, 4, (1), 63.
12. Erkan, M., Understanding the stroma of pancreatic cancer: co-evolution of the microenvironment with epithelial carcinogenesis. *The Journal of Pathology* 2013, n/a-n/a.
13. Baker, J. A. R.; Wickremsinhe, E. R.; Li, C. H.; Oluyedun, O. A.; Dantzig, A. H.; Hall, S. D.; Qian, Y.-w.; Ring, B. J.; Wrighton, S. A.; Guo, Y., Pharmacogenomics of Gemcitabine Metabolism: Functional Analysis of Genetic Variants in Cytidine Deaminase and Deoxycytidine Kinase. *Drug Metabolism and Disposition* 2013, 41, (3), 541-545.
14. Sugahara, K. N.; Teesalu, T.; Karmali, P. P.; Kotamraju, V. R.; Agemy, L.; Greenwald, D. R.; Ruoslahti, E., Coadministration of a Tumor-Penetrating Peptide Enhances the Efficacy of Cancer Drugs. *Science* 2010, 328, (5981), 1031-1035.
15. Goel, S.; Duda, D. G.; Xu, L.; Munn, L. L.; Boucher, Y.; Fukumura, D.; Jain, R. K., Normalization of the Vasculature for Treatment of Cancer and Other Diseases. *Physiological Reviews* 2011, 91, (3), 1071-1121.
16. Winkler, E. A.; Bell, R. D.; Zlokovic, B. V., Central nervous system pericytes in health and disease. *Nat Neurosci* 2011, 14, (11), 1398-1405.
17. Darland, D. C.; D'Amore, P. A., TGFβ is required for the formation of capillary-like structures in three-dimensional cocultures of 10T1/2 and endothelial cells. *Angiogenesis* 2001, 4, (1), 11-20.
18. Cabral H; MatsumotoY; MizunoK; ChenQ; MurakamiM; KimuraM; TeradaY; Kano, M. R.; MiyazonoK; UesakaM; NishiyamaN; KataokaK, Accumulation of sub-100 nm polymeric micelles in poorly permeable tumours depends on size. *Nat Nano* 2011, 6, (12), 815-823.
19. Lammerts, E.; Roswall, P.; Sundberg, C.; Gotwals, P. J.; Koteliansky, V. E.; Reed, R. K.; Heldin, N.-E.; Rubin, K., Interference with TGF-β1 and -β3 in tumor stroma lowers tumor interstitial fluid pressure independently of growth in experimental carcinoma. *International Journal of Cancer* 2002, 102, (5), 453-462.
20. ten Dijke, P.; Arthur, H. M., Extracellular control of TGF[beta] signalling in vascular development and disease. *Nat Rev Mol Cell Biol* 2007, 8, (11), 857-869.
21. Antonelli-Orlidge, A.; Saunders, K. B.; Smith, S. R.; D'Amore, P. A., An activated form of transforming growth factor beta is produced by cocultures of endothelial cells and pericytes. *Proceedings of the National Academy of Sciences* 1989, 86, (12), 4544-4548.
22. Walshe, T. E.; Saint-Geniez, M.; Maharaj, A. S. R.; Sekiyama, E.; Maldonado, A. E.; D'Amore, P. A., TGF-beta Is Required for Vascular Barrier Function, Endothelial Survival and Homeostasis of the Adult Microvasculature. *PLoS ONE* 2009, 4, (4), e5149.
23. Kano, M. R.; Komuta, Y.; Iwata, C.; Oka, M.; Shirai, Y.-t.; Morishita, Y.; Ouchi, Y.; Kataoka, K.; Miyazono, K., Comparison of the effects of the kinase inhibitors imatinib, sorafenib, and transforming growth factor-β receptor inhibitor on extravasation of nanoparticles from neovasculature. *Cancer Science* 2009, 100, (1), 173-180.
24. Yingling, J. M.; Blanchard, K. L.; Sawyer, J. S., Development of TGF-[beta] signalling inhibitors for cancer therapy. *Nat Rev Drug Discov* 2004, 3, (12), 1011-1022.
25. Vogt, J.; Traynor, R.; Sapkota, G. P., The specificities of small molecule inhibitors of the TGF-beta and BMP pathways. *Cellular Signalling* 2011, 23, (11), 1831-1842.
26. Meng, H.; Liong, M.; Xia, T.; Li, Z.; Ji, Z.; Zink, J. I.; Nel, A. E., Engineered Design of Mesoporous Silica Nanoparticles to Deliver Doxorubicin and P-Glycoprotein siRNA to Overcome Drug Resistance in a Cancer Cell Line. *ACS Nano* 2010, 4, (8), 4539-4550.
27. Meng, H.; Xue, M.; Xia, T.; Zhao, Y.-L.; Tamanoi, F.; Stoddart, J. F.; Zink, J. I.; Nel, A. E., Autonomous in Vitro Anticancer Drug Release from Mesoporous Silica Nanoparticles by pH-Sensitive Nanovalves. *Journal of the American Chemical Society* 2010, 132 12690-12697.
28. Meng, H.; Xue, M.; Xia, T.; Ji, Z.; Tarn, D. Y.; Zink, J. I.; Nel, A. E., Use of Size and a Copolymer Design Feature To Improve the Biodistribution and the Enhanced Permeability and Retention Effect of Doxorubicin-Loaded Mesoporous Silica Nanoparticles in a Murine Xenograft Tumor Model. *ACS Nano* 2011, 5, 4131-4144.
29. Meng, H.; Yang, S.; Li, Z.; Xia, T.; Chen, J.; Ji, Z.; Zhang, H.; Wang, X.; Lin, S.; Huang, C.; Zhou, Z. H.; Zink, J. I.; Nel, A. E., Aspect Ratio Determines the Quantity of Mesoporous Silica Nanoparticle Uptake by a Small GTPase-Dependent Macropinocytosis Mechanism. *ACS Nano* 2011, 5 4434-4447.
30. Meng, H.; Xue, M.; Zink, J. I.; Nel, A. E., Development of Pharmaceutically Adapted Mesoporous Silica Nanoparticles Platform. *The Journal of Physical Chemistry Letters* 2012, 3, (3), 358-359.
31. Meng, H.; Mai, W. X.; Zhang, H.; Xue, M.; Xia, T.; Lin, S.; Wang, X.; Zhao, Y.; Ji, Z.; Zink, J. I.; Nel, A. E., Codelivery of an Optimal Drug/siRNA Combination Using Mesoporous Silica Nanoparticles To Overcome Drug Resistance in Breast Cancer in Vitro and in Vivo. *ACS Nano* 2013, 7, (2), 994-1005.
32. Mai, W. X.; Meng, H., Mesoporous silica nanoparticles: A multifunctional nano therapeutic system. *Integrative Biology* 2013, 5, (1), 19-28.
33. Song, N.; Huang, Y.; Shi, H.; Yuan, S.; Ding, Y.; Song, X.; Fu, Y.; Luo, Y., Overexpression of Platelet-Derived Growth Factor-BB Increases Tumor Pericyte Content via Stromal-Derived Factor-1ɸ/CXCR4 Axis. *Cancer Research* 2009, 69, (15), 6057-6064.
34. Varelas, X.; Samavarchi-Tehrani, P.; Narimatsu, M.; Weiss, A.; Cockburn, K.; Larsen, B. G.; Rossant, J.; Wrana, J. L., The Crumbs Complex Couples Cell Density Sensing to Hippo-Dependent Control of the TGF-β-SMAD Pathway. *Developmental Cell* 2010, 19, (6), 831-844.
35. Chen, J.; Shearer, G. C.; Chen, Q.; Healy, C. L.; Beyer, A. J.; Nareddy, V. B.; Gerdes, A. M.; Harris, W. S.; O'Connell, T. D.; Wang, D., Omega-3 Fatty Acids Prevent Pressure Overload-Induced Cardiac Fibrosis Through Activation of Cyclic GMP/Protein Kinase G Signaling in Cardiac Fibroblasts. *Circulation* 2011, 123, (6), 584-593.
36. Farace, P.; Merigo, F.; Fiorini, S.; Nicolato, E.; Tambalo, S.; Daducci, A.; Degrassi, A.; Sbarbati, A.; Rubello, D.; Marzola, P., DCE-MRI using small-molecular and albumin-binding contrast agents in experimental carcinomas with different stromal content. *European Journal of Radiology* 2011, 78, (1), 52-59.
37. Ferrari, M., Cancer nanotechnology: opportunities and challenges. *Nat Rev Cancer* 2005, 5, (3), 161-171.
38. Estrella, V.; Chen, T.; Lloyd, M.; Wojtkowiak, J.; Cornnell, H. H.; Ibrahim-Hashim, A.; Bailey, K.; Balagurunathan, Y.; Rothberg, J. M.; Sloane, B. F.; Johnson, J.; Gatenby, R. A.; Gillies, R. J., Acidity Generated by the Tumor Microenvironment Drives Local Invasion. *Cancer Research* 2013, 73, (5), 1524-1535.
39. Fakhrejahani, E.; Toi, M., Tumor Angiogenesis: Pericytes and Maturation Are Not to Be Ignored. *Journal of Oncology* 2012, Article ID 261750.
40. Federico, C.; Morittu, V.; Britti, D.; Trapasso, E.; Cosco, D., Gemcitabine-loaded liposomes: rationale, potentialities and future perspectives. *International Journal of Nanomedicine* 2012, 2012, 5423-5436.
41. Haran, G.; Cohen, R.; Bar, L. K.; Barenholz, Y., Transmembrane ammonium sulfate gradients in liposomes produce efficient and stable entrapment of amphipathic weak bases. *Biochimica et Biophysica Acta (BBA)—Biomembranes* 1993, 1151, (2), 201-215.
42. Castelli, F.; Raudino, A.; Fresta, M., A mechanistic study of the permeation kinetics through biomembrane models: Gemcitabine-phospholipid bilayer interaction. *Journal of Colloid and Interface Science* 2005, 285, (1), 110-117.
43. Glezerman, I.; Kris, M.; Miller, V.; Seshan, S.; Flombaum, C., Gemcitabine nephrotoxicity and hemolytic uremic syndrome: report of 29 cases from a single institution. *Clin Nephrol* 2009, 71, 130-139.
44. von Maltzahn, G.; Park, J.-H.; Lin, K. Y.; Singh, N.; Schw??ppe, C.; Mesters, R.; Berdel, W. E.; Ruoslahti, E.; Sailor, M. J.; Bhatia, S. N., Nanoparticles that communicate in vivo to amplify tumour targeting. *Nat Mater* 2011, 10, (7), 545-552.
45. Watson, K. D.; Lai, C.-Y.; Qin, S.; Kruse, D. E.; Lin, Y.-C.; Seo, J. W.; Cardiff, R. D.; Mahakian, L. M.; Beegle, J.; Ingham, E. S.; Curry, F.-R.; Reed, R. K.; Ferrara, K. W., Ultrasound Increases Nanoparticle Delivery by Reducing Intratumoral Pressure and Increasing Transport in Epithelial and Epithelial-Mesenchymal Transition Tumors. *Cancer Research* 2012, 72, (6), 1485-1493.
46. Frese, K. K.; Neesse, A.; Cook, N.; Bapiro, T. E.; Lolkema, M. P.; Jodrell, D. I.; Tuveson, D. A., nab-Paclitaxel Potentiates Gemcitabine Activity by Reducing Cytidine Deaminase Levels in a Mouse Model of Pancreatic Cancer. *Cancer Discovery* 2012, 2, (3), 260-269.
47. Liu, J.; Liao, S.; Diop-Frimpong, B.; Chen, W.; Goel, S.; Naxerova, K.; Ancukiewicz, M.; Boucher, Y.; Jain, R. K.; Xu, L., TGF-β blockade improves the distribution and efficacy of therapeutics in breast carcinoma by normalizing the tumor stroma. *Proceedings of the National Academy of Sciences* 2012, 109, (41), 16618-16623.
48. Dreaden, E. C.; Mwakwari, S. C.; Austin, L. A.; Kieffer, M. J.; Oyelere, A. K.; El-Sayed, M. A., Small Molecule-Gold Nanorod Conjugates Selectively Target and Induce Macrophage Cytotoxicity towards Breast Cancer Cells. *Small* 2012, 8, (18), 2819-2822.
49. Fang, J.; Nakamura, H.; Maeda, H., The EPR effect: Unique features of tumor blood vessels for drug delivery, factors involved, and limitations and augmentation of the effect. *Advanced Drug Delivery Reviews* 2011, 63, (3), 136-151.
50. Jacobetz, M. A.; Chan, D. S.; Neesse, A.; Bapiro, T. E.; Cook, N.; Frese, K. K.; Feig, C.; Nakagawa, T.; Caldwell, M. E.; Zecchini, H. I.; Lolkema, M. P.; Jiang, P.; Kultti, A.; Thompson, C. B.; Maneval, D. C.; Jodrell, D. I.; Frost, G. I.; Shepard, H. M.; Skepper, J. N.; Tuveson, D. A., Hyaluronan impairs vascular function and drug delivery in a mouse model of pancreatic cancer. *Gut* 2012.
51. Provenzano, P. P.; Cuevas, C.; Chang, A. E.; Goel, V. K.; Von Hoff, D. D.; Hingorani, S. R., Enzymatic Targeting of the Stroma Ablates Physical Barriers to Treatment of Pancreatic Ductal Adenocarcinoma. *Cancer Cell* 2012, 21, (3), 418-429.
52. http://www.halozyme.com/files/2011EORTCPEGPH20.pdf
53. http://ir.celgene.com/phoenix.zhtml?c=111960&p=irol-newsArticle&ID=1776848&highlight=.
54. Von Hoff, D. D.; Ramanathan, R. K.; Borad, M. J.; Laheru, D. A.; Smith, L. S.; Wood, T. E.; Korn, R. L.; Desai, N.; Trieu, V.; Iglesias, J. L.; Zhang, H.; Soon-Shiong, P.; Shi, T.; Rajeshkumar, N. V.; Maitra, A.; Hidalgo, M., Gemcitabine Plus nab-Paclitaxel Is an Active Regimen in Patients With Advanced Pancreatic Cancer: A Phase I/II Trial. *Journal of Clinical Oncology* 2011, 29, (34), 4548-4554.
55. Darland, D. C.; D'Amore, P. A., TGF-beta is required for the formation of capillary-like structures in three-dimensional cocultures of 10T1/2 and endothelial cells. *Angiogenesis* 2001, 4, (1), 11-20.
56. Quatromoni, J.; Wang, Y.; Vo, D.; Morris, L.; Jazirehi, A.; McBride, W.; Chatila, T.; Koya, R.; Economou, J., T cell receptor (TCR)-transgenic CD8 lymphocytes rendered insensitive to transforming growth factor beta (TGFbeta) signaling mediate superior tumor regression in an animal model of adoptive cell therapy. *Journal of Translational Medicine* 2012, 10, (1), 127.
57. Zhang, Q.; Yang, X.; Pins, M.; Javonovic, B.; Kuzel, T.; Kim, S.-J.; Parijs, L. V.; Greenberg, N. M.; Liu, V.; Guo, Y.; Lee, C., Adoptive Transfer of Tumor-Reactive Transforming Growth Factor-beta Insensitive CD8+ T Cells: Eradication of Autologous Mouse Prostate Cancer. *Cancer Research* 2005, 65, (5), 1761-1769.

B. Electron Microscopy Image of Tumor Tissue of Mice Injected with Tgfβi-MSNP

An electron microscopic image of a BxPC3 tumor section from an animal injected i.v. with TGFβi-MSNP is shown in FIG. 9.

C. Design, Synthesis, Drug Loading and Characterization of Gemcitabine-Loaded Liposomes Materials:
All the phospholipids products were purchased from Avanti Polar Lipids, either powder form or chloroform solution without further purification. Gemcitabine (GEM) was purchased from Sigma Aldrich. The liposomal mini-extruder, holder/heating block, and different size PC Membranes (0.4 and 0.1 μm) were purchased from Avanti Polar Lipids.
Optimization of GEM Loading in the Liposome Platform by Creating a Trans-Liposomal-Membrane Ammonium Sulfate Gradient.
The liposomal composition is shown in Table 1. Liposomes were prepared through a thin film-rehydration procedure. GEM was encapsulated using an equilibrium exchange method for liposomal trapping (BMC Cancer 2004, 4, 63). Inclusion of ammonium sulfate inside the liposome generates a transmembrane gradient, which is responsible for protonation of the amphipathic GEM molecules which can freely diffuse through the liposome bilayer. However, after their protonation the GEM molecules become hydrophilic, which prevents their escape from the liposome. The drug becomes stabilized as gel-like drug precipitate [i.e. (GEM-NH3)2SO4] inside the liposomes. FIG. 10A provides a flow chart showing the major steps of GEM loading, and in order to obtain optimal drug loading, each step had to be systematically investigated through to find the best possible liposome formulation, ammonium sulfate concentration, extent of salt removal, drug loading time, temperature, and amount of free GEM, etc (FIG. 10B).

TABLE 1

Formulation of different liposome for GEM loading.
Formulation

| | |
|---|---|
| #1 | DOPC |
| #2 | DPPC |
| #3 | DOPC:Cholesterol:DSPE-PEG2K = 7:2:1 |
| #4 | DOPC:Cholesterol:DSPE-PEG2K = 6:3:1 |
| #5 | DPPC:Cholesterol:DSPE-PEG2K = 7:2:1 |
| #6 | DPPC:Cholesterol:DSPE-PEG2K = 6:3:1 |

Briefly, the lipid mixture for each formulation (#1-#6) was dissolved in a round-bottomed flask, using chloroform as solvent (concentration: 2.5~10 mg/mL). Different liposomal compositions are listed in Table 1. Based on the preliminary tests in which liposome size and polydispersity indices were compared, a decision was made to use formulation #5 (DPPC:Cholesterol:DSPE-PEG2K=7:2:1) to perform further optimization of loading because of the homogeneity of the liposome. Then lipid films were made by evaporation for ~1 h, using a rotary evaporator connected to a vacuum system at room temperature. These films were placed in a chemical hood overnight to remove trace amounts of organic solvent impurities. The lipid films can be stored at −80° C. under inert atmosphere (i.e. argon, nitrogen) for at least 2 months. We also produced fluorescent liposomes by co-dissolving 0.1% w/w fluorescein-DHPE (i.e. texas red) with the lipids. For rehydration, lipid films were incubated with indicated concentrations of ammonium sulfate solution (ranging from 0-360 mM) at 60° C. for 1 h, with vigorous stirring. In order to make homogeneous unilamellar liposomes, the multi-lamellar particles were repeatedly extruded, first at a 400 nm pore size (3 times), then at a 100 nm pore size 11 times, while being kept at 60° C. on a heating block. In order to remove the non-trapped ammonium sulfate, ultra-speed centrifugation at 100,000 rpm or repeated dialysis against isotonic glucose solution was performed. The resulting mono-disperse, unilamellar vesicles were suspended in an isotonic solution of GEM hydrochloride at different free GEM concentrations (0.2-5 mg/mL). These suspensions were kept at different temperatures (4-80° C.) for 1-24 and the free drug was removed by dialysis. In order to determine the drug loading capacity, the encapsulated GEM was quantified by UV absorption at 270 nm using a microplate reader (Molecular Device). The elemental phosphorus (P) was quantified by ICP-OES (ICPE-9000, Shimadzu). Drug loading capacity (%) was determined as (amount of GEM)/(amount of liposome)×100%. The size of the drug-laden liposomes was characterized by dynamic light scattering at a liposome concentration of 100 μg/mL (ZetaPALS, Brookhaven Instruments Co.). The zeta potential of the liposome was measured by a ZetaPALS (Brookhaven Instruments Co.). The morphology of drug-laden liposome was visualized by cyroEM (TF20, FET).

After systematic variation of all the parameters, optimal GEM encapsulation could be achieved with:
- A salt concentration: 120 nM
- Dialysis: 3 dialysis cycles (6 mL against 1000 mL, 6 h/cycle)
- Free GEM concentration: 1 mg/mL
- Incubation temperature: 60° C.
- Incubation time: 10 h Through the use of optimal parameters, we could achieve a GEM loading capacity of ~20% (w/w). Use of the optimal set of parameters (outlined in green in FIG. 10A) allowed us to construct liposomes with a primary particle size of ~137 nm, as shown by cyroEM image (FIG. 10C). The hydrodynamic size in saline was 137 nm, with a $\zeta$ potential of ~1.7 mV (FIG. 10D). Stability testing demonstrated that GEM is stably retained for at least 21 days at 4° C., with <5.9% premature release.

Subsequent performance of confocal microscopy utilizing red fluorescent-labeled liposomes at 25 µg/mL, demonstrated a high rate of cellular uptake in the human pancreatic cancer cell line, BxPC3, after a 6 h incubation period (FIG. 10E, left panel). To demonstrate the in vitro killing capability of the drug-laden liposomes, we used the MTS assay to compare the rate of BxPC3 cell death with incremental GEM concentrations (FIG. 10E, right panel). Free GEM at the equivalent free drug concentration was included as control. GEM delivery by the liposome clearly linked to an increased rate of cytotoxicity compared to the free drug. Liposomal drug encapsulation improves the IC50~5 fold compared to free drug at 48 h.

We also assess the ability of the liposome to protect GEM against the effect of on cytidine deaminase (CDA), which plays a key role in drug inactivation (circulatory half-life of <8 minutes) in the clinic. Briefly, free GEM or GEM-laden liposomes were mixed with CDA enzyme at a concentration of 100 ng/mL in the incubation medium for 1 h at 37° C. The incubation media were then added to BxPC3 cells, which were cultured in 96 wells plate for 72 h. IC50 values were determined by the MTS assay for each group. The results were compared to the IC50 values for GEM or GEM-liposomes, not incubated with CDA. Noteworthy, the effective in vitro killing of the GEM-liposome was accompanied by protection of the drug against CDA (FIG. 10F). By contrast, free GEM was not protected against the effect of CDA.

Figure 10:
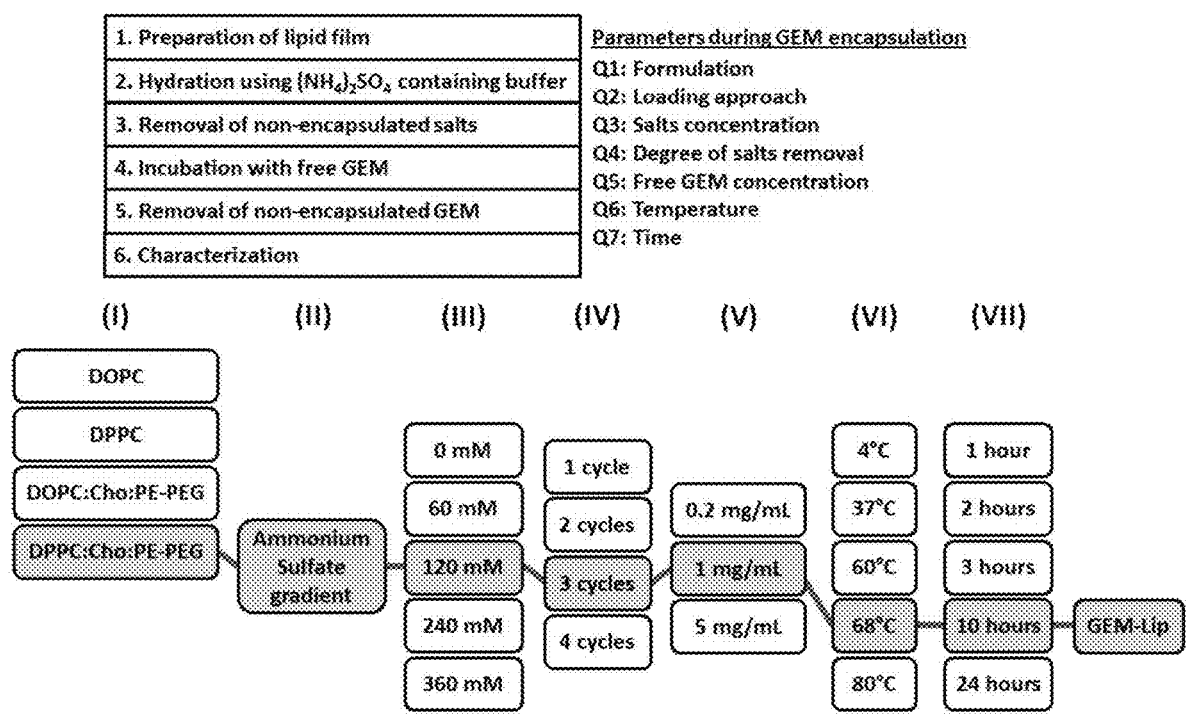
FIG. 10 shows optimization of GEM loading in the liposome platform by creating a trans-liposomal-membrane ammonium sulfate gradient. (A) Upper panel: A scheme to show the major steps in the (NH4)2SO4 mediated GEM loading. Lower panel: By adjusting the parameters during liposome synthesis and drug loading, a highly efficient loading protocol was established for each indicated formulation. The results showed that the DPPC:Cholesterol:DSPE-PEG2K (7:2:1) liposome (formulation #5) can be used for GEM loading using a (NH4)2SO4 mediated loading approach. In order to obtain high drug loading capacity, a list of parameters [(I) liposome formulation, (II) loading approach, (III) salt concentration, (IV) extent of salt removal, (V) extent of loading under various non-encapsulated GEM concentration, (VI) incubation temperature and (VII) incubation time] were systemically explored to develop the optimal loading conditions. (C) CyroEM image shows the primary size and unilamellar structure of GEM-laden liposome in saline. The thickness of lipid bilayer was determined to be 9 nm based on a quantitative analysis using Image J software. (D) A hydrodynamic particle size and (potential in saline were measured. The synthesis optimization yielded a unilamilar liposome nanoparticle with a slightly negative zeta potential, hydrodynamic diameter of 137 nm in saline of a DPI index of 0.004. (E) Left: Cellular uptake of red-labeled liposomes in BxPC3 cells. Confocal microscopy was used to study the cellular uptake of liposome in BxPC3 cells. Cells were exposed to 25 µg/mL labeled particles for 6 h. Cell nuclear were stained by Hochest dye. After cell membrane staining with 5 µg/mL green-fluorescent wheat germ agglutinin (WGA 488), cells were visualized using a confocal 1P/FCS inverted microscope. Right: MTS assay was conducted for the GEM-loaded liposome delivered to these cells at incremental GEM doses over a 48 h period in BxPC3 cells. No cytotoxicity was found using empty liposome (not shown). The controls were cells treated with PBS or empty particles. The experiment was reproduced two times. (F) Demonstration of protective effect of liposomal encapsulation on CDA-mediated GEM inactivation.

D. Full Panel of NIR Images to Cover all the Time Points in Mice Injected with Second Wave NIR-MNSP as Shown in FIG. 5A are shown in FIG. 10

E. Demonstration of the Effects of TGFβi-MSNP Treatment on Improving the Intratumoral Distribution of a "Hard Particle" in BxPC3 Xenografts In order further confirm the effect of TGFβi-MSNP treatment on improving biodistribution of "hard particles", 50 nm amine-modified, PEGylated MSNP with a Dylight680 NIR tag were tested in xenograft tumors. The same experiment was performed as described in FIG. 5A. Briefly, the BxPC3-luc tumor-bearing animals were pre-treated by i.v. injection of TGFβi-MSNP (inhibitor: 1 mg/kg; particle: 2 mg/kg) followed by i.v. injection of 50 mg/kg of the 50 nm MSNP after a time lag of 1-2 h. The in vivo biodistribution was compared with the mice receiving i.v. injection of the same amount of the 2nd wave particle alone. Consistent with the results in FIG. 5, the NIR fluorescent images showed that, compared to the treatment using the 2nd wave treatment alone, there was a significant increase at tumor site in the mice prior treated with TGFβi-MSNP (FIG. 12).

Figure 11:
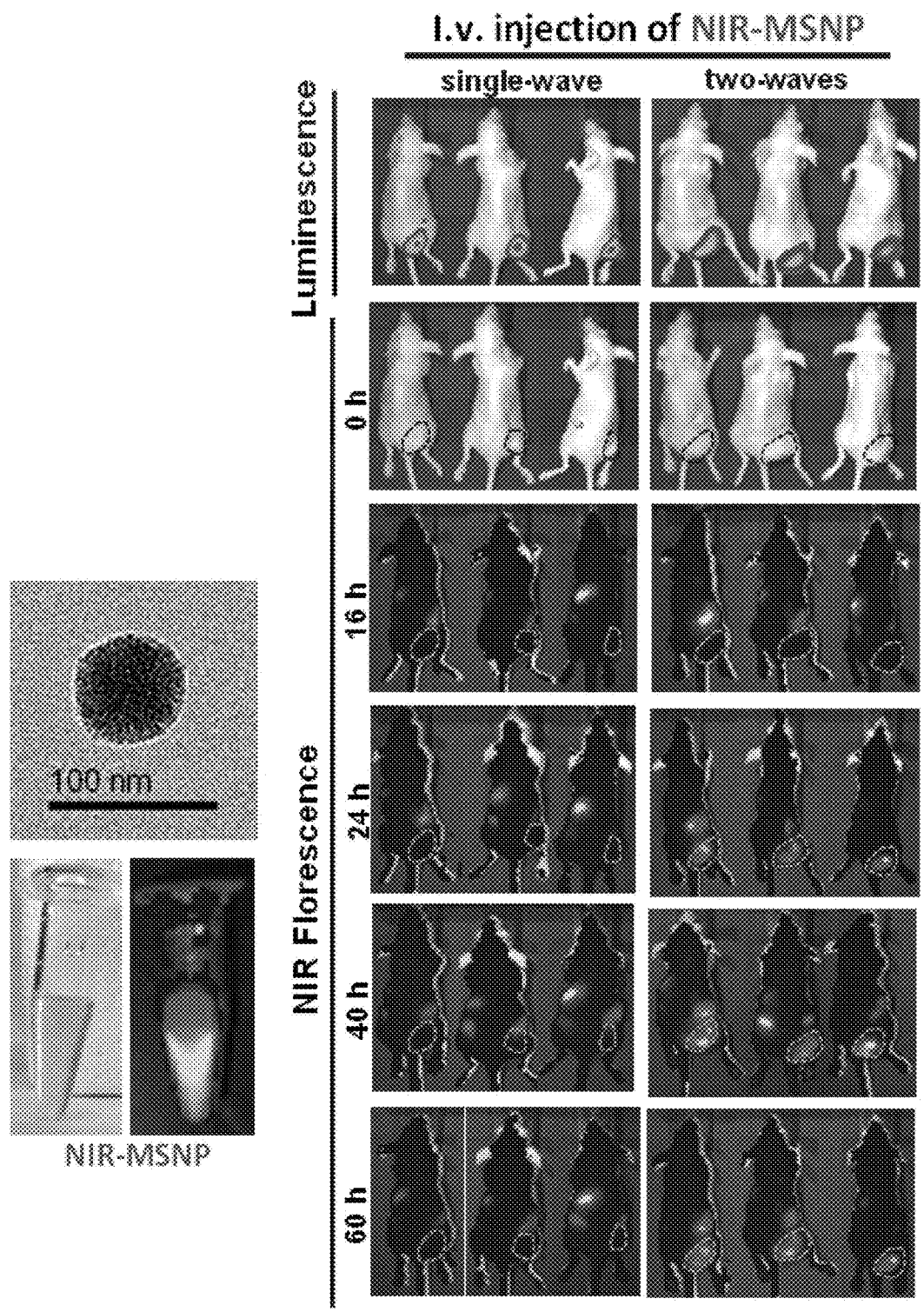
in FIG. 11. The NIR fluorescent intensities were analyzed at different time points by software and shown in the lower panel of (A) and (B). *, $P<0.05$. (C-D) For PEI-PEG-MSNP, 60 h after injection, the animals were sacrificed and tumor tissues as well as major organs (heart, lung, spleen, liver, kidney, brain, and muscle) were collected for ex vivo imaging. ICP-OES was used to quantify the Si abundance in the major target organs using our established procedure.28 As a result of the shorter retention time of liposomes, we repeated the experiments in (B) with a new batch of animals in which the tumor tissue and organs were harvested at 24 h for ex vivo imaging. The tumor tissue together with major organs were collected and used for ex vivo imaging. Around 100 mg of tumor, spleen, liver, and kidney was accurately weighed out, washed, and homogenated, and the fluorescence intensities per unitary amount of each organ were measured by a microplate reader (M5e, Molecular Devices). The biodistribution of each particle type was expressed as percent of total load of each nanoparticle distributing to the individual organs. This percent is determined according to the formula [(particle quantity per unit mass tissue×tumor or organ weight)/(total injected particle)]×100%. *, $P<0.05$, two-wave compared to use of particle alone.

F. Full Panel of NIR Images to Show the Biodistribution of Second Wave NIR-Liposomes at all Time Points for the Experiment Described in FIG. 5B is shown in FIG. 11

TABLE 2

| Parameters groups | Saline | Free Liposome | TGFβi-MSNP alone | Free GEM | GEM-Lip | Two waves |
|---|---|---|---|---|---|---|
| CO2 (mEq/L) | 24.4 ± 0.6 | 26.8 ± 1.3 | 23.2 ± 1.5 | 20.5 ± 2.8 | 21.4 ± 0.6 | 21.8 ± 2.7 |
| CHOL (mg/dL) | 78.0 ± 15.1 | 65.0 ± 2.6 | 73.0 ± 2 | 58.7 ± 4.0 | 43.0 ± 31.8 | 68.3 ± 11.8 |
| PHOS (U/L) | 5.4 ± 0.7 | 5.7 ± 0.9 | 4.8 ± 0.8 | 6.1 ± 1.0 | 6.2 ± 0.8 | 3.8 ± 0.7 |
| AST (mg/dL) | 156.9 ± 138.9 | 164.7 ± 66.0 | 150.9 ± 79.3 | 221.8 ± 177.7 | 111.7 ± 93.7 | 275.4 ± 59.2 |
| DBILI (mg/dL) | 0.5 ± 0.3 | 0.5 ± 0.1 | 0.5 ± 0.2 | 0.7 ± 0.5 | 0.7 ± 0.2 | 0.6 ± 0.2 |
| TBILI (mg/dL) | 0.6 ± 0.2 | 0.4 ± 0.1 | 0.4 ± 0.1 | 0.5 ± 0.2 | 0.4 ± 0.1 | 0.5 ± 0.2 |
| BUN (mg/dL) | 25.0 ± 1.7 | 26.7 ± 3.0 | 33.7 ± 3.5 | 38.0 ± 11.3 | 32.7 ± 9.5 | 27.5 ± 2.3 |
| CK (U/L) | 362.5 ± 187.4 | 550.0 ± 134.5 | 647.0 ± 489.2 | 512.0 ± 39.6 | 550.0 ± 84.8 | 743.0 ± 165.1 |
| CREAT (mg/dL) | 0.1 ± 0.0 | 0.2 ± 0.0 | 0.2 ± 0.0 | 0.2 ± 0.0 | 0.1 ± 0.1 | 0.2 ± 0.1 |
| GGT (U/L) | 5.7 ± 0.5 | 5.0 ± 1 | 4.7 ± 1.2 | 5.3 ± 1.155 | 6.7 ± 0.577 | 6.5 ± 0.577 |
| GLU (mg/dL) | 101.0 ± 14.8 | 129.7 ± 81.4 | 174.0 ± 36.5 | 128.3 ± 16.9 | 129.0 ± 32.6 | 153.3 ± 12.8 |
| TP (g/dL) | 4.8 ± 0.2 | 5.0 ± 0.2 | 5.1 ± 0.5 | 5.1 ± 0.2 | 5.3 ± 0.6 | 5.8 ± 0.4 |
| ALB (g/dL) | 2.9 ± 0.1 | 3.0 ± 0.2 | 3.0 ± 0.2 | 3.2 ± 0.1 | 3.2 ± 0.2 | 3.5 ± 0.1 |
| ALP (U/L) | 29.3 ± 13.6 | 43.9 ± 9.9 | 47.6 ± 8.2 | 55.8 ± 9.8 | 51.9 ± 27.2 | 77.3 ± 8.1 |
| CA (mg/dL) | 9.5 ± 0.2 | 9.9 ± 0.4 | 8.8 ± 1.3 | 9.4 ± 0.3 | 9.2 ± 0.5 | 9.7 ± 0.4 |
| ALT (U/L) | 19.6 ± 11.8 | 34.0 ± 7.5 | 25.9 ± 6.8 | 42.5 ± 33.8 | 26.5 ± 3.3 | 44.0 ± 18.5 |
| BUN_CR (mg/dL) | 466.7 ± 378.6 | 190.1 ± 68.0 | 178.9 ± 63.8 | 190.7 ± 16.0 | 281.9 ± 164.2 | 142.5 ± 45.4 |

Blood was collected from the sacrificed animals and the sera separated by centrifuging the whole blood at 5,000 rpm for 15 min. The biochemical parameters were assayed by the UCLA Division of Laboratory Animal Medicine (DLAM) diagnostic laboratory services. These parameters include bicarbonate (CO2), cholesterol (CHOL), inorganic phosphorus (PHOS), aspartate aminotransferase (AST), direct serum bilirubin (DBILI), total bilirubin (TBILI), blood urea nitrogen (BUN), creatine kinase (CK), creatinine (CREAT), gamma glutamyl transferase (GGT), glucose (GLU), total protein (TP), albumin (ALB), alkaline phosphatase (ALP), calcium (CA), alanine aminotransferase (ALT), and BUN-to-creatinine ratio (BUN-CR). The biochemical analysis did not show any significant changes among different treatments.

H. Materials and Methods

Materials.

N-(2-Aminoethyl)-3-aminopropyltrimethoxysilane (NAPTS) was purchased from Gelest (Morrisville, PA).

Cetyl trimethylammonium bromide (CTAB, 95%), tetraorthoethylsilicate (TEOS, 98%), 3-(trihydroxysilyl) propyl methylphosphonate (42% in $H_2O$), Pluronic F127, polyethyleneimine (PEI, 1.2 kD), 4-(dimethylamino)pyridine (99%), N,N'-disuccinimidyl carbonate (95%), poly(ethylene glycol) methyl ether (m-PEG, MW 5 kD), phthalic anhydride (99%), transforming growth factor-β1 (TGF-β) and gemcitabine hydrochloride (purity: >98%) were purchased from Sigma Aldrich (St. Louis, MO). Amine-reactive near-infrared Fluor Dylight 680 NHS ester was purchased from Thermo Scientific (Rockford, IL). D-Luciferin was purchased from Xenogen (Alameda, CA). Cell Tracker™ Red CMTPX, Cell Tracker™ Green CMFDA (5-Chloromethylfluorescein Diacetate), DPBS solution, L-glutamine, penicillin, streptomycin, and DMEM culture medium were obtained from Invitrogen. Fetal bovine serum (FBS) was purchased from Atlanta Biologicals. Anti-Smad2 (phospho S467) antibody was purchased from Abcam. Anti-CD31 antibody and Matrigel™-Basement Membrane Matrix was purchased from BD Bioscience. Transforming growth factor type I receptors kinas inhibitor (TGFβi, LY364947) was purchased from EMD Millipore. Phospholipids and cholesterol were purchased from Avanti Polar Lipids (Alabaster, Alabama). All reagents were used without further purification.

Physicochemical Characterization.

Samples were characterized for morphology, size distribution and surface charge. The morphologies and primary sizes of MSNP particle were characterized using a transmission electron microscope (JEOL JEM 2010, JEOL USA, Inc., Peabody, MA). The morphologies of liposome were characterized using cyroEM (TF20, FET). Hydrodynamic size and zeta potential in solution were measured by Zeta-Sizer Nano (Malvern Instruments Ltd., Worcestershire, UK). All of the measurements were performed with the samples suspended in filtered water or saline at 100 μg/mL nanoparticle concentration.

Establishment of BxPC3-Luc Cells.

Permanent luciferase transfection using lentivirus was performed by UCLA vector core facility. Briefly, $1.5 \times 10^4$ BxPC3 cells immersed in 40 μL complete DMEM were transduced with 10 μL of lentivirus solution (Cignal Finder Lenti Pathway Reporter Qiagen/SA Biosciences; $1.4 \times 10^7$ TU/mL) using 96 well tissue culture plates. Centrifugal inoculation was performed at 1,200 g for 60 minutes. The viral containing media was removed after 16 h and the cultures replenished with fresh DMEM media. Cells were allowed to proliferate to a population size of $1.2 \times 10^6$ cells. Limiting dilution was used to select individual cell that express the highest luciferase. The highest luciferase expressing clone (refers as BxPC3-luc) out of 10 single clones was used for further experiments.

ICP-OES Analysis:

The collected tumor and organs were used for Si elemental analysis using ICP-OES. Briefly, each tissue was accurately weighed and soaked in concentrated 1 mL $HNO_3$ and 0.5 mL 30% $H_2O_2$ for overnight. This yellow color digestion solution was heated at 80° C. for 1 h in the subsequent day. Dropwise addition of $H_2O_2$ solution was used to drive off nitrogen oxide vapor until the digestion lipid turns colorless. 2% $HNO_3$ was used to dilute the sample into 10 mL volume and the resulting sample was analyzed by ICP-OES.

Blood Biochemistry and Histology to Assess Possible Toxicity

Following the animal experiments described above, the mice were sacrificed on the $38^{th}$ day and serum was collected by centrifuging the whole blood at 5,000 rpm for 15 min. The biochemical parameters were assayed by UCLA Division of Laboratory Animal Medicine (DLAM) diagnostic laboratory services.

Appropriate size sections of the tumor, liver, kidney, and spleen were fixed in 10% formalin and then embedded into paraffin. Tissue sections of 4 m thickness were mounted on glass slides by the UCLA Division of Laboratory Animal Medicine (DLAM) diagnostic laboratory services. The sections were stained with hematoxylin-eosin (H&E) and examined by light microscopy.

Example II

A. Introduction

An MSNP coated with a phospholipid bilayer is described which can provide a GEM loading capacity of ~40% (drug/particle, w/w). The MSNP core is synthesized by a modified surfactant-templated sol-gel method in aqueous solution at relatively low temperature. Moreover, to coat this NP with an intact lipid bilayer, a lipid membrane was dehydrated with a GEM-containing MSNP suspension, using controlled energy input (e.g. sonication). This led to rapid coating and sealing of the MSNPs, encapsulating a high w/w content GEM in one step.

Since pancreatic cancer can in many cases be resistant to individual chemotherapeutic agents, including GEM, via acquired or de novo mechanisms, there is a need to consider drugs that provide a synergistic effect with GEM, e.g., when co-administered with GEM. In this regard, a recent successful clinical trial has allowed Abraxane® (paclitaxel/albumin complex) to be combined with GEM in untreated pancreatic patients with metastatic disease. This combination has resulted in a statistically significant improvement in overall survival compared to patients receiving GEM alone. Without wishing to be bound by theory, paclitaxel is believed to be capable of increasing the intratumoral GEM content by reducing the activity of cytidine deaminase (CDA), a key enzyme that metabolically inactivates GEM and reduces its circulatory half-life to minutes. Since the hydrophobic paclitaxel molecules can be co-dissolved in a lipophilic organic solution, the presence of a lipid coat on MSNP allows co-packaging of paclitaxel in a phospholipid bilayer coating on GEM-laden particles.

Reports by Celano et al. in 2004 and Cosco et al. in 2009 discuss using a liposome for GEM delivery (see BMC Cancer 2004, 4:63; Cancer Chemother Pharmacol, 2009, 64:1009-1020, each of which is incorporated by reference in its entirety). In the 2004 study, the authors describe a GEM loading capacity 0.3% (w/w, drug/particle). In the 2009 year study, the authors describe GEM loading capacity of 1.3% (w/w, drug/particle). Reports by Brinker et al. discuss porous silica nanoparticle-supported lipid bilayers, also known as "protocells" for drug delivery (Nat. Materials 2011, 10, 389, which is incorporated by reference in its entirety).

In some embodiments, a low temperature sol-gel chemistry procedure is used to obtain highly uniform (e.g., monodisperse) and colloidally stable MSNPs. MSNPs prepared via a low temperature sol-gel method can exhibit improved size control than those prepared by, for example, an aerosol-assisted self-assembly method. Particles prepared by an aerosol-assisted self-assembly method may exhibit a wide size distribution, and may not be uniformly bio-available, e.g., at tumor sites. In contrast, the monodisperse and size-controlled MSNPs prepared by a sol-gel method may show greater potential for in vivo use.

In some embodiments, a submicron structure (such as an MSNP coated with a phospholipid bilayer) can provide simultaneous delivery of a drug, and: an agent which stabilizes the drug against metabolic degradation; an agent which facilitates the delivery of the drug to a target cell, tissue, organ or tumor; an agent which acts synergistically with the drug; one or more additional therapeutic agents; or a combination thereof. In some embodiments, a GEM-laden MSNP provides for simultaneous delivery of paclitaxel in a single carrier, i.e., a submicron structure which includes both GEM (e.g., within the pores) and paclitaxel (e.g., associated with the phospholipid bilayer). Including more than one therapeutic agent in a single particle allows precise control over the doses and dosage ratios of the therapeutic agents delivered to the site of release (e.g., a tumor cell).

B. Synthesis Procedure of Lipid-Coated MSNP and Drug Loading

B1. Synthesis of MSNP Via Sol-Gel Chemistry

Chemicals:

The chemicals were obtained from Sigma Aldrich and used without further purification.

Small Batch MSNP Synthesis:

5 mL cetyltrimethylammonium chloride (CTAC) (25%) was mixed with 15 mL $H_2O$, and stirred for 15 min at 75° C. (350 rpm). Added 0.8 mL 10% TEA water solution, mixed at 75° C. for 15 min (350 rpm). Added dropwise 1 mL tetraethyl orthosilicate (TEOS) as silica precursor, at a rate of 30 drops per minute. The mixture was stirred continuously at 350 rpm at 80° C. for 1 h. A white nanoparticle suspension gradually developed, with a primary size of about 60 nm to about 70 nm.

Scaled Up MSNP Synthesis:

25 mL CTAC (25%) was mixed with 75 mL $H_2O$, at 95° C. in a 200 mL conical flask. 4 mL 10% TEA, was added, the mixture was stirred at 95° C. for 30 min. A pump was used to deliver 7.5 mL TEOS at 1 ml/min to the flask. The reaction was allowed to proceed at 95° C. for 20 min. TEM analysis showed the primary particle size of ~70 nm.

B2. Washing to Remove Surfactant

Prepared washing buffer containing methanol and HCl at 500:19 (v/v). Added 50 mL acidic washing buffer into scaled up synthesis system (~100 mL). Stirred at 350 rpm at room temperature for overnight. Spun down particles at 15,000 rpm for 10 min (1.5 mL tube) or 10,000 rpm for 30 min (50 mL tube). Used probe-sonicator to re-suspend the particles using fresh methanol. Washed the particles for at least 3 times. Frequent DLS analysis was carried out to confirm the absence of particle aggregation/contamination. TEM was used to confirm the particle morphology before use. IR or cytotoxicity assay was used to confirm whether the detergent was thoroughly removed.

B3. Drug Loading 10 mg MSNP was suspended in 20 mg GEM ethanol/water (7:3, v/v). The mixture was shaken for at least 24 hour at room temperature. The drug-laden particles were collected by centrifugation (prior to pore sealing) and immediately used for lipid coating. Particles were not washed between drug loading and lipid coating.

B4. Phospholipid Bilalyer Coating of GEM-Laden MSNP

The lipid membrane was dehydrated using GEM-containing MSNP suspension with controlled energy input (e.g. sonication), leading to lipid-coated and pore-sealed MSNPs that contained high GEM content in one step. Lipid membrane: Lipid mixture was dissolved in a round-bottomed flask, using chloroform as solvent (concentration: 2.5~10 mg/mL). Different liposomal compositions can be selected based on drug, targeting purpose, and other considerations. Paclitaxel can be co-dissolved in the organic solution. Lipid films were made by evaporation for ~1 h, using a rotary evaporator connected to a vacuum system at room temperature. These films were placed in a chemical hood for at least 2 hours to remove trace amounts of organic solvent impurities. The lipid films can be stored at −80° C. under an inert atmosphere for at least 2 months. Fluorescently labeled lipid film can be made by co-dissolving 0.1% w/w fluorescein-DHPE (i.e. Texas red) with the lipids. For rehydration, lipid films were incubated with the GEM-laden MSNP aqueous solution at 40° C. for 20 min, with continuous water-bath sonication. The mixture was spun at 1500 rpm for 5 min and the supernatant collected, which contain lipid-coated MSNP, free GEM, and free liposome. A centrifugal filter unit with 10,000 MW cutting off size was used to remove any unencapsulated GEM.

Sample characterization: The samples were fully characterized for morphology using TEM and cryoEM, size and zeta potential, surface area, loading capacity and release profile, and Si/P elemental ratio using ICP-OES.

C. In Vitro Demonstration to Show the Effects of GEM/Paclitaxel Loaded Lipid-Coated MSNP in Pancreatic Cancer Cells.

C1. Determination of Morphology and GEM Loading Capacity in MSNP

Figure 14:
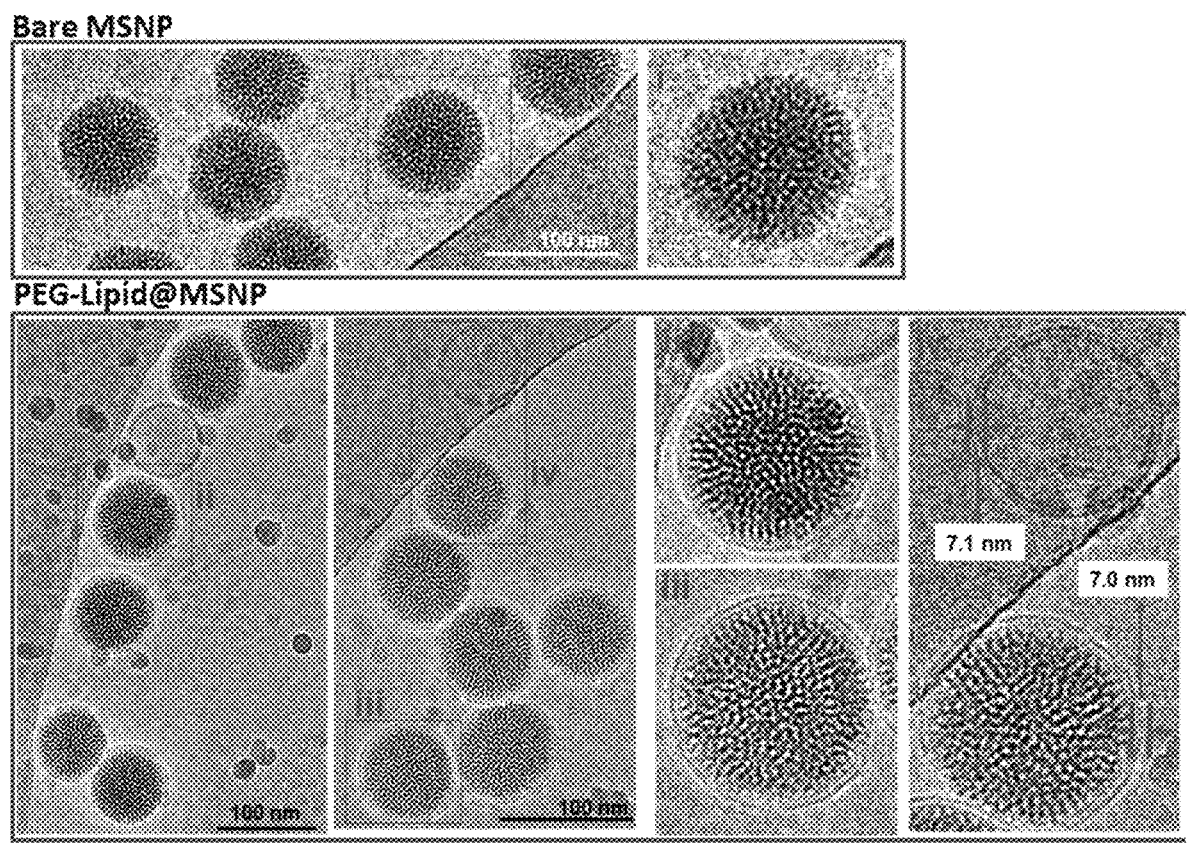
FIG. 14 shows cryoEM images of lipid coated MSNP.

CryoEM images of lipid coated MSNP are shown in FIG. 14, which shows a cryoEM image (TF20, FET) of lipid-coated MSNP. The upper box shows the ~70 nm MSNP synthesized using the procedure in section D. The zoom-in image (region 1) shows an ordered mesoporous structure and primary particle size of ~60 nm. The lower panel shows an intact lipid coating on the silica surface. The zoom-in images (regions ii→iv) showed a lipid thickness of 7.0 nm on the silica surface, which is very close to the thickness of lipid bilayer in liposome (7.1 nm). The HPLC analysis and microplate reader analysis showed that the loading capacity of GEM in lipid coated MSNP was ~40% (w/w). This is an approximately 2-fold improvement compared to GEM-laden liposome.

Figure 15:
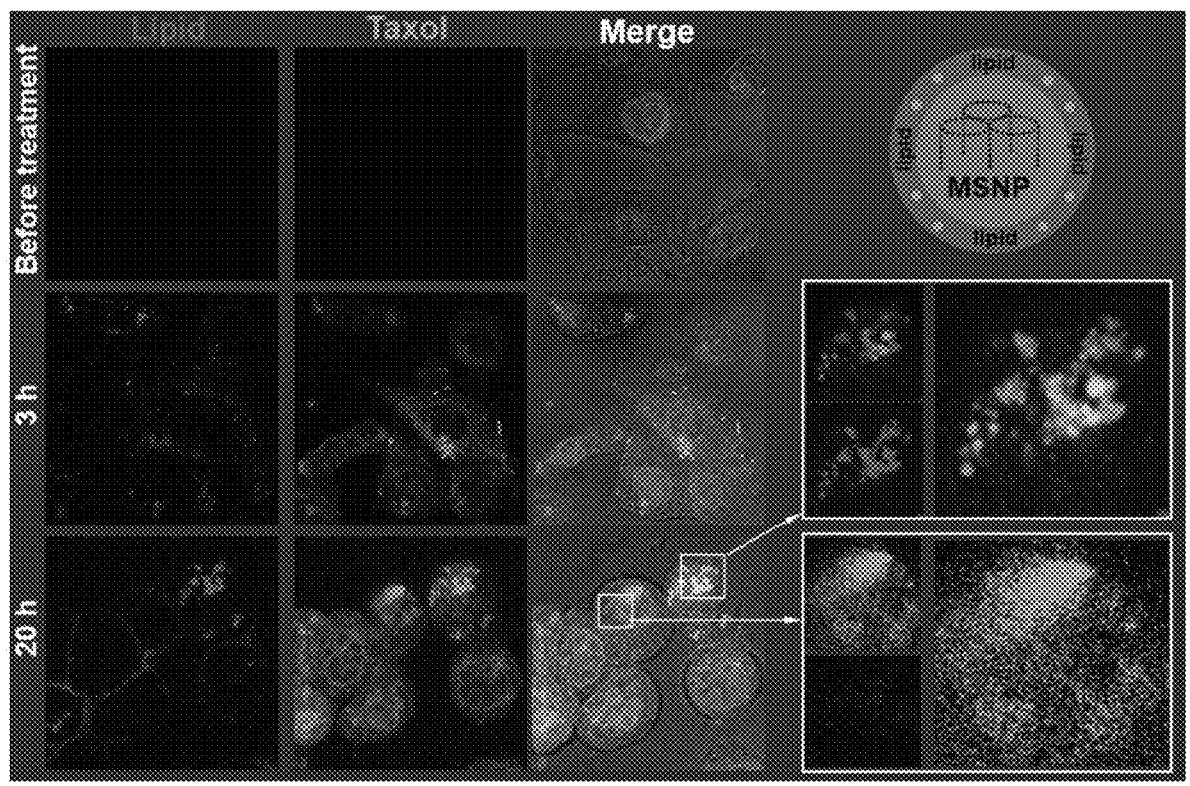
FIG. 15 shows confocal microscope images of Panel cells before and at time points after treatment with drug-loaded MSNP.

C2. Cellular Uptake of the Lipid Bilayer-Coated MSNP and its Ability to Provide Intracellular Delivery of Cancer Drugs in Panel Cells FIG. 15 demonstrates cellular uptake of the lipid bilayer-coated MSNP. Confocal microscopy was used to demonstrate the cellular uptake of FITC-labeled paclitaxel (in green) loaded DHPE (red)-labeled lipid-coated MSNP in Panc1 cells. Panc cells were treated with 40 μg/mL nanoparticles for the indicated time periods. The merged image at 3 hours showed the red-labeled lipid bilayer in association with green-labeled paclitaxel, which indicated that the particle successfully delivered paclitaxel into the cells, while the lipid coating remained intact. However, the merged images at 20 hours show amore dispersed pattern of intracellular paclitaxel distribution and lower level of co-localization, providing evidence of intracellular paclitaxel release from the MSNP's lipid coating where the hydrophobic drug was packaged. The nuclear were stained by Hoechst 33342 in blue.

C3. Paclitaxel-Laden Lipid Coated MSNP Down-Regulated the Expression of Cytidine Deaminase (CDA), a Key Enzyme in Metabolic Inactivation of GEM in Pancreatic Cancer Cells.

Figure 16:
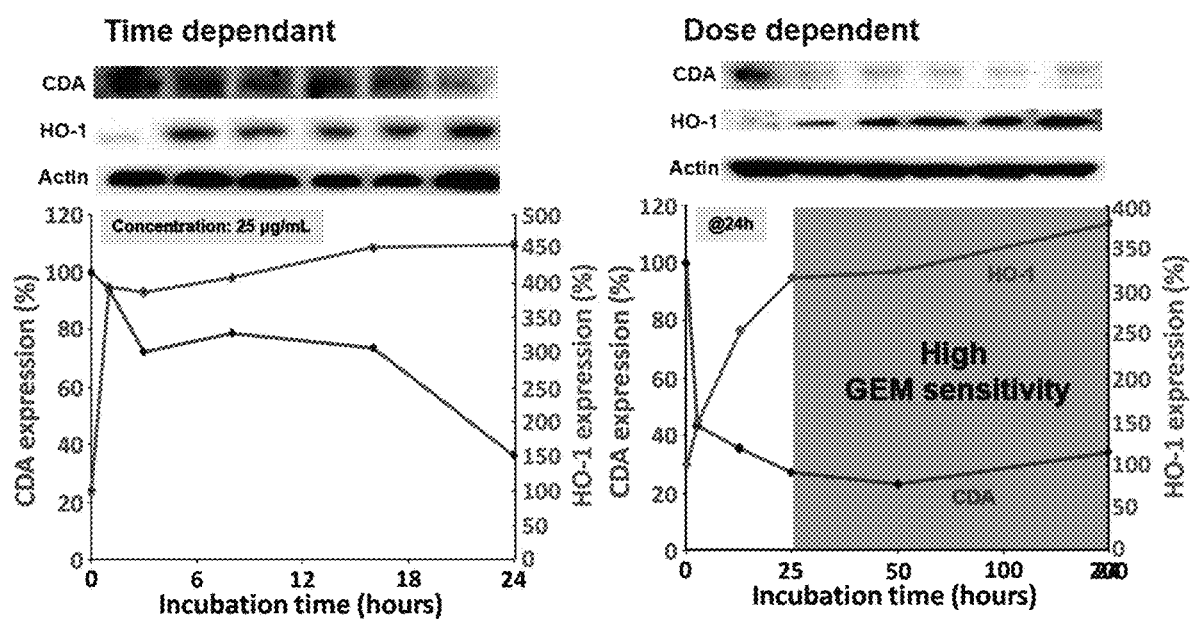
FIG. 16 shows results of time- and dose-dependent treatment of Panc1 cells with paclitaxel-laden lipid coated MSNP on expression levels of cytidine deaminase.

As illustrated in FIG. 16, Panc1 cells were treated with paclitaxel-laden lipid coated MSNP at 25 μg/mL for different lengths of time (0-24 hours), or for 24 hours using different particle concentrations (0-200 μg/mL). The expression of CDA and heme oxygenase-1 (HO-1, which is an oxidative stress protein induced in response to paclitaxel induced oxidative challenge) were determined by Western blotting. The data demonstrated that paclitaxel-laden lipid coated MSNP significantly lowered the CDA expression and induced HO-1 level in a dose- and time-dependent manner. The data showed that 24-hour incubation at particle concentration of 25 µg/mL could lead to the maximal effects in Panc1 cells.

We claim:

1. A drug delivery carrier comprising:
   a silica body having a plurality of pores suitable to receive a therapeutic agent therein, and having a surface;
   an intact lipid bilayer coating the surface and encapsulating the silica body and stably sealing the plurality of pores, wherein the encapsulating is performed without lipid phase exchange and without contacting a preformed liposome with the silica body;
   a first therapeutic agent within the pores of the silica body, wherein the first therapeutic agent comprises gemcitabine; and
   a second therapeutic agent disposed in the lipid bilayer, wherein the second therapeutic agent comprises paclitaxel.

2. The drug delivery carrier of claim 1, wherein the drug delivery carrier provides a predetermined dose and ratio of first therapeutic agent to second therapeutic agent.

3. The drug delivery carrier of claim 1, wherein the first therapeutic agent and the second therapeutic agent act synergistically.

4. The drug delivery carrier of claim 1, wherein the drug delivery carrier includes about 20% w/w or greater of gemcitabine molecules within the pores of the silica body.

5. The drug delivery carrier of claim 1, wherein the drug delivery carrier includes about 30% w/w or greater of gemcitabine molecules within the pores of the silica body.

6. The drug delivery carrier of claim 1, wherein the drug delivery carrier includes about 40% w/w or greater of gemcitabine molecules within the pores of the silica body.

7. The drug delivery carrier of claim 1, wherein the lipid bilayer is formed from a lipid film containing the second therapeutic agent.

8. The drug delivery carrier of claim 1, wherein the drug delivery carrier is configured to retain the first therapeutic agent within the silica body without substantial loss for at least 1 week prior to administration to a subject.

9. The drug delivery carrier of claim 1, wherein the drug delivery carrier is configured to retain the first therapeutic agent within the silica body with 10% or less loss for at least 1 week prior to administration to a subject.

10. The drug delivery carrier of claim 1, wherein the drug delivery carrier is a member of a monodisperse population of drug delivery carriers.

11. The drug delivery carrier of claim 1, wherein the drug delivery carrier is a submicron structure with a maximum dimension of between 20 nm and 300 nm.

12. The drug delivery carrier of claim 1, wherein the drug delivery carrier has a submicron structure with a maximum dimension of between 50 nm and 200 nm.

13. The drug delivery carrier of claim 1, wherein the lipid bilayer comprises a phospholipid bilayer.

14. The drug delivery carrier of claim 13, wherein the phospholipid bilayer comprises 2-dioleoyl-3-trimethylammonium-propane (DOTAP), 1,2-dioleoyl-sn-glycero-3-phospho-L-serine (DOPS),1,2-dioleoyl-sn-glycero-3-phosphocholine (DOPC), or any combination thereof.

15. A composition comprising a plurality of drug delivery carriers, each drug delivery carrier comprising:
    a silica body having a plurality of pores suitable to receive a therapeutic agent therein, and having a surface;
    an intact lipid bilayer coating the surface and encapsulating the silica body and stably sealing the plurality of pores, wherein the encapsulating is performed without lipid phase exchange and without contacting a preformed liposome with the silica body;
    a first therapeutic agent within the pores of the silica body, wherein the first therapeutic agent comprises gemcitabine; and
    a second therapeutic agent disposed in the lipid bilayer, wherein the second therapeutic agent comprises paclitaxel.

16. The composition of claim 15, wherein the composition comprises a stable colloidal suspension.

17. The composition of claim 15, wherein the plurality of drug delivery carriers provides a predetermined dose and ratio of the first therapeutic agent to the second therapeutic agent.

18. The composition of claim 15, wherein the plurality of drug delivery carriers form a monodisperse population having a deviation in average diameter of 10% or less.

19. The composition of claim 15, wherein the composition is formulated for systemic administration to a subject for treating cancer.

20. The composition of claim 15, wherein the composition is formulated for intravenous, intra-arterial, intraperitoneal, intramuscular, or subcutaneous administration.

* * * * *